US010391152B2

(12) United States Patent
Jiang et al.

(10) Patent No.: US 10,391,152 B2
(45) Date of Patent: Aug. 27, 2019

(54) METHODS OF USING A FIXED DOSE OF A CLOTTING FACTOR

(71) Applicant: Bioverativ Therapeutics Inc., Waltham, MA (US)

(72) Inventors: Haiyan Jiang, Belmont, MA (US); Lei Diao, Somerville, MA (US); Shuanglian Li, Lexington, MA (US); Paula Cobb, Lincoln, MA (US)

(73) Assignee: Bioverativ Therapeutics Inc., Waltham, MA (US)

( * ) Notice: Subject to any disclaimer, the term of this patent is extended or adjusted under 35 U.S.C. 154(b) by 481 days.

(21) Appl. No.: 14/436,667

(22) PCT Filed: Oct. 18, 2013

(86) PCT No.: PCT/US2013/065772
§ 371 (c)(1),
(2) Date: Apr. 17, 2015

(87) PCT Pub. No.: WO2014/063108
PCT Pub. Date: Apr. 24, 2014

(65) Prior Publication Data
US 2016/0296607 A1    Oct. 13, 2016

Related U.S. Application Data

(60) Provisional application No. 61/715,746, filed on Oct. 18, 2012, provisional application No. 61/759,856, filed on Feb. 1, 2013, provisional application No. 61/760,000, filed on Feb. 1, 2013.

(51) Int. Cl.
*A61K 38/36* (2006.01)
*A61K 38/48* (2006.01)
*C12N 9/64* (2006.01)

(52) U.S. Cl.
CPC .......... *A61K 38/4846* (2013.01); *A61K 38/36* (2013.01); *C12N 9/644* (2013.01); *C12Y 304/21022* (2013.01); *C07K 2319/30* (2013.01)

(58) Field of Classification Search
None
See application file for complete search history.

(56) References Cited

U.S. PATENT DOCUMENTS

| | | |
|---|---|---|
| 4,757,006 A | 7/1988 | Toole, Jr. et al. |
| 4,868,112 A | 9/1989 | Toole, Jr. |
| 4,965,199 A | 10/1990 | Capon et al. |
| 4,994,371 A | 2/1991 | Davie et al. |
| 5,004,803 A | 4/1991 | Kaufman et al. |
| 5,112,950 A | 5/1992 | Meulien et al. |
| 5,171,844 A | 12/1992 | Van Ooyen et al. |
| 5,364,771 A | 11/1994 | Lollar et al. |
| 5,543,502 A | 8/1996 | Nordfang et al. |
| 5,595,886 A | 1/1997 | Chapman et al. |
| 5,610,278 A | 3/1997 | Nordfang et al. |
| 5,712,122 A | 1/1998 | Boime et al. |
| 5,789,203 A | 8/1998 | Chapman et al. |
| 5,846,951 A | 12/1998 | Gregoriadis |
| 5,859,204 A | 1/1999 | Lollar |
| 5,972,885 A | 10/1999 | Spira et al. |
| 6,048,720 A | 4/2000 | Dalborg et al. |
| 6,060,447 A | 5/2000 | Chapman et al. |
| 6,228,620 B1 | 5/2001 | Chapman et al. |
| 6,251,632 B1 | 6/2001 | Lillicrap et al. |
| 6,316,226 B1 | 11/2001 | Van Ooyen et al. |
| 6,346,513 B1 | 2/2002 | Van Ooyen et al. |
| 6,376,463 B1 | 4/2002 | Lollar |
| 6,458,563 B1 | 10/2002 | Lollar |
| 7,041,635 B2 | 5/2006 | Kim et al. |
| 7,199,223 B2 | 4/2007 | Bossard et al. |
| 7,348,004 B2 | 3/2008 | Peters et al. |
| 7,381,408 B2 | 6/2008 | Mezo et al. |
| 7,404,956 B2 | 7/2008 | Peters et al. |
| 7,632,921 B2 | 12/2009 | Pan et al. |
| 7,820,162 B2 | 10/2010 | Mezo et al. |
| 7,862,820 B2 | 1/2011 | Peters et al. |
| 8,329,182 B2 | 12/2012 | Peters et al. |
| 8,932,830 B2 | 1/2015 | Peters et al. |
| 9,050,318 B2 | 6/2015 | Dumont et al. |
| 9,233,145 B2 | 1/2016 | Pierce et al. |

(Continued)

FOREIGN PATENT DOCUMENTS

| | | |
|---|---|---|
| EP | 0154316 A2 | 9/1985 |
| EP | 0295597 A2 | 12/1988 |

(Continued)

OTHER PUBLICATIONS

Nishijima et al., Acad Emerg Med. Mar. 2010;17(3):244-51. doi: 10.1111/j.1553-2712.2010.00666.x.*
Bobrow R.S., J Am Board Fam Pract. Mar.-Apr. 2005;18(2):147-9.*
Van Hylckama Vlieg et al., Blood. Jun. 15, 2000;95(12):3678-82.*
Bjorkman S., Haemophilia. May 2003;9 Suppl 1:101-8; discussion 109-10. Review.*
Collins et al., J Thromb Haemost. Feb. 2010;8(2):269-75. doi: 10.1111/j.1538-7836.2009.03703.x. Epub Nov. 23, 2009.*

(Continued)

*Primary Examiner* — Michael Szperka
(74) *Attorney, Agent, or Firm* — Lathrop Gage LLP; James H. Velema, Esq.

(57) ABSTRACT

The present invention provides methods of administering a clotting factor by a fixed dosing regimen; methods of reducing, ameliorating, or preventing one or more symptoms of a bleeding disease or disorder; and a kit comprising a dotting factor useful for a fixed dosing regimen. While plasma-derived and recombinant clotting factor products allow hemophilia patients to live longer and healthier, hemophilia still remains one of the most costly and complex conditions to manage.

14 Claims, 8 Drawing Sheets
Specification includes a Sequence Listing.

(56) References Cited

U.S. PATENT DOCUMENTS

| | | | |
|---|---|---|---|
| 9,241,978 B2 | 1/2016 | Dumont et al. | |
| 9,629,903 B2 | 4/2017 | Pierce et al. | |
| 9,670,475 B2* | 6/2017 | Pierce | A61K 38/4846 |
| 9,675,676 B2 | 6/2017 | Pierce et al. | |
| 2003/0203845 A1* | 10/2003 | Knudsen | A61K 38/4846 |
| | | | 424/94.64 |
| 2005/0100990 A1 | 5/2005 | Saenko et al. | |
| 2007/0021494 A1 | 1/2007 | Taveras et al. | |
| 2008/0004206 A1 | 1/2008 | Rosen et al. | |
| 2008/0033413 A1 | 2/2008 | Inochkin et al. | |
| 2008/0153751 A1 | 6/2008 | Rosen et al. | |
| 2008/0161243 A1 | 7/2008 | Rosen et al. | |
| 2008/0194481 A1 | 8/2008 | Rosen et al. | |
| 2008/0261877 A1 | 10/2008 | Ballance et al. | |
| 2009/0058322 A1 | 3/2009 | Toma et al. | |
| 2009/0087411 A1 | 4/2009 | Fares et al. | |
| 2009/0163699 A1 | 6/2009 | Chamberlain et al. | |
| 2009/0264627 A1 | 10/2009 | Gillies et al. | |
| 2010/0292130 A1 | 11/2010 | Skerra et al. | |
| 2011/0159540 A1 | 6/2011 | Mezo et al. | |
| 2012/0178691 A1 | 7/2012 | Schellenberger et al. | |
| 2012/0225819 A1* | 9/2012 | Jezek | A61K 9/0019 |
| | | | 514/14.1 |
| 2013/0202595 A1 | 8/2013 | Pierce et al. | |
| 2015/0139947 A1 | 5/2015 | Peters et al. | |
| 2015/0252345 A1 | 9/2015 | Pierce et al. | |
| 2015/0266944 A1 | 9/2015 | Jiang et al. | |
| 2016/0166657 A1 | 6/2016 | Pierce et al. | |
| 2016/0199455 A1 | 7/2016 | Dumont et al. | |
| 2016/0257943 A1 | 9/2016 | Pierce et al. | |

FOREIGN PATENT DOCUMENTS

| | | |
|---|---|---|
| EP | 0401384 A1 | 12/1990 |
| EP | 2173890 B1 | 3/2011 |
| WO | WO-8704187 A1 | 7/1987 |
| WO | WO-8800831 A1 | 2/1988 |
| WO | WO-8803558 A1 | 5/1988 |
| WO | WO-8808035 A1 | 10/1988 |
| WO | WO-9109122 A1 | 6/1991 |
| WO | WO-9216221 A1 | 10/1992 |
| WO | WO-9320093 A1 | 10/1993 |
| WO | WO-9411503 A2 | 5/1994 |
| WO | WO-9534326 A1 | 12/1995 |
| WO | WO-0240544 A2 | 5/2002 |
| WO | WO-03020764 A2 | 3/2003 |
| WO | WO-2004101740 A2 | 11/2004 |
| WO | WO-2005001025 A2 | 1/2005 |
| WO | WO-2006074199 A1 | 7/2006 |
| WO | WO-2007021494 A2 | 2/2007 |
| WO | WO-2007149406 A2 | 12/2007 |
| WO | WO-2008033413 A2 | 3/2008 |
| WO | WO-2008118507 A2 | 10/2008 |
| WO | WO-2008155134 A1 | 12/2008 |
| WO | WO-2009051717 A2 | 4/2009 |
| WO | WO-2009058322 A1 | 5/2009 |
| WO | WO-2009130198 A2 | 10/2009 |
| WO | WO-2009137254 A2 | 11/2009 |
| WO | WO-2009140015 A2 | 11/2009 |
| WO | WO-2011069164 A2 | 6/2011 |
| WO | WO-2012006623 A1 | 1/2012 |
| WO | WO-2012006624 A2 | 1/2012 |
| WO | WO-2012006633 A1 | 1/2012 |
| WO | WO-2012006635 A1 | 1/2012 |
| WO | WO-2014063108 A1 | 4/2014 |

OTHER PUBLICATIONS

Rocca et al., Blood Transfus. Jan. 2011;9(1):60-9. doi: 10.2450/2010.0011-10. Epub Apr. 30, 2010.*

Armour, K.L., et al., "Recombinant Human IgG Molecules Lacking FcγReceptor I Binding and Monocyte Triggering Activities," European Journal of Immunology 29(8):2613-2624, Wiley-VCH, Germany (1999).

Bai, S ., et al., "A Guide to Rational Dosing of Monoclonal Antibodies," Clinical Pharmacokinetics 51(2):119-135, ADIS Press, Switzerland (2012).

Bai, Y., et al., "Recombinant granulocyte colony-stimulating factor-transferrin fusion protein as an oral myelopoietic agent," Proceedings of the National Academy of Sciences USA 102(20):7292-7296, National Academy of Sciences, United States (2005).

Bjorkman, S., et al., "Population Pharmacokinetics of Recombinant Factor VIII: The Relationships of Pharmacokinetics to Age and Body Weight," Blood 119(2):612-618, American Society of Hematology, United States (2012).

Blankenship, C.S., "To Manage Costs of Hemophilia, Patients Need More than Clotting Factor," Biotechnology Healthcare 5(4):37-40, MediMedia, United States (2008).

Bovenschen, N., et al., "LDL Receptor Cooperates with LDL Receptor-Related Protein in Regulating Plasma Levels of Coagulation Factor VIII in vivo," Blood 106(3):906-912, The American Society of Hematology, United States (2005).

Bovenschen, N., "LDL Receptor Polymorphisms Revisited," Blood 116(25);5439-5440, The American Society of Hematology, United States (2010).

Brandsma, M.E., et al., "Recombinant human transferrin: Beyond iron binding and transport," Biotechnology Advances 29(2):230-238, Elsevier, United States (2011).

Brutlag, D.L., et al., "Improved Sensitivity of Biological Sequence Database Searches," Computer Applications in the Biosciences 6(3):237-245, Oxford University Press, England (1990).

Burmeister, W.P., et al., "Crystal Structure of the Complex of Rat Neonatal Fc Receptor with Fc," Nature 372(6504):379-383, Nature Publishing Group, England (1994).

Cameron, C., et al., "The Canine Factor VIII cDNA and 5' Flanking Sequence," Thrombosis and Haemostasis 79(2):317-322, Schattauer, Germany (1998).

Cutler, J.A., et al., "The Identification and Classification of 41 novel Mutations in the Factor VIII Gene (F8C)," Human Mutation 19(3):274-278, Wiley-Liss, Inc., United States (2002).

Dennis, M.S., et al., "Albumin Binding as a General Strategy for Improving the Pharmacokinetics of Proteins," The Journal of Biological Chemistry 277(38):35035-35043, American Society for Biochemistry and Molecular Biology, United States (2002).

Dobeli, H., et al., "Role of the Carboxy-terminal Sequence on the Biological Activity of Human Immune Interferon (IFN-γ)," Journal of Biotechnology 7(3):199-216, Elsevier Science Publishers B.V., Netherlands (1988).

Eaton, D.L., et al., "Construction and Characterization of an Active Factor VIII Variant Lacking the Central One-Third of the Molecule," Biochemistry 25(26):8343-8347, American Chemical Society, United States (1986).

Fatouros, A., et al., "Recombinant Factor VIII SQ—Influence of Oxygen, Metal Ions, pH and Ionic Strength on its Stability in Aqueous Solution," International Journal of Pharmaceutics 155(1):121-131, Elsevier Science B.V., United Kingdom (1997).

Francis, G.E., "Protein Modification and Fusion Proteins," Focus on Growth Factors 3(2):4-10, Mediscript, United Kingdom (1992).

Friend, P.J., et al., "Phase I Study of an Engineered Aglycosylated Humanized CD3 Antibody in Renal Transplant Rejection," Transplantation 68(11):1632-1637, Lippincott Williams & Wilkins, Inc., United States (1999).

Gayle, R.B., III., et al., "Identification of Regions in Interleukin-1α Important for Activity," The Journal of Biological Chemistry 268(29):22105-22111, The American Society for Biochemistry and Molecular Biology, Inc., United States (1993).

GenBank, "*Homo sapiens* Transferrin (TF), mRNA," Accession No. NM_001063.3, version 3 first published on Sep. 3, 2009, available at http://www.ncbi.nlm.nih.gov/nuccore/NM_001063, last accessed on Sep. 24, 2014, 5 pages.

GenBank, "*Homo sapiens* Transferrin (TF), mRNA," Accession No. XM_002793.7, version 7 first published on May 13, 2002, available at https://www.ncbi.nlm.nih.gov/nuccore/XM_002793.7?report=genbank, last _accessed on Sep. 24, 2014, 2 pages.

(56) References Cited

OTHER PUBLICATIONS

GenBank, "*Homo sapiens* Transferrin (TF), mRNA," Accession No. XM_039847.1, version 1 first published on Jul. 16, 2001, last accessed at http://www.ncbi.nlm.nih.gov/nuccore/XM_039847.1?report=genbank, accessed on Sep. 24, 2014, 2 pages.
GenBank, "*Homo sapiens* Transferrin (TF), mRNA," Accession No. XM_039845.1, version 1 first published Jul. 16, 2001, available at https://www.ncbi.nlm.nih.gov/nuccore/XM_039845.1?report=genbank, last accessed on Sep. 24, 2014, 2 pages.
GenBank, "Human Transferrin mRNA, Complete cds," Accession No. M12530.1, version 1 first published on Jan. 14, 1995, last accessed at http://www.ncbi.nlm.nih.gov/nuccore/M1253014, accessed on Jan. 15, 2015, 2 pages.
GenBank, "Transferrin [human, liver, mRNA, 2347 nt]," Accession No. S95936.1, version 1 first published on May 7, 1993, available at http://www.ncbi.nlm.nih.gov/nuccore/S95936, last accessed on Sep. 24, 2014, 2 pages.
Gitschier, J., et al., "Characterization of the Human Factor VIII Gene," Nature 312(5992):326-330, Nature Publishing Group, England (1984).
Healey, J.F., et al., "The cDNA and Derived Amino Acid Sequence of Porcine Factor VIII," Blood 88(11):4209-4214, The American Society of Hematology, United States (1996).
Hoeben, R.C., et al., "Expression of Functional Factor VIII in Primary Human Skin Fibroblasts after Retrovirus-mediated Gene Transfer," The Journal of Biological Chemistry 265(13):7318-7323, The American Society for Biochemistry and Molecular Biology, United States (1990).
Holt, L.J., et al., "Anti-Serum Albumin Domain Antibodies for Extending the Half-Lives of Short Lived Drugs," Protein Engineering, Design & Selection 21(5):283-288, Oxford University Press, England (2008).
International Preliminary Report on Patentability for Application No. PCT/US2013/065772, The International Bureau of WIPO, Geneva, Switzerland, dated Apr. 21, 2015, 6 pages.
International Search Report and Written Opinion for Application No. PCT/US2013/065772, ISA/US, Alexandria, Virginia, United States, dated Jan. 17, 2014, 10 pages.
Khorsand, N., et al., "An Observational, Prospective, Two-cohort Comparison of a Fixed Versus Variable Dosing Strategy of Prothrombin Complex Concentrate to Counteract Vitamin K Antagonists in 240 Bleeding Emergencies," Haematologica 97(10):1501-1506, Ferrata Storti Foundation, Italy (2012).
Kim, B.J., et al., "Transferrin Fusion Technology: a Novel Approach to Prolonging Biological Half-Life of Insulinotropic Peptides," The Journal of Pharmacology and Experimental Therapeutics 334(3):682-692, American Society for Pharmacology and Experimental Therapeutics, United States (2010).
Kraulis, P.J., et al., "The Serum Albumin-Binding Domain of Streptococcal Protein G is a Three-Helical Bundle: a Heteronuclear NMR study," FEBS Letters 378(2):190-194, Elsevier Science B.V, Netherlands (1996).
Langner, K-D., et al., "Synthesis of Biologically Active Deletion Mutants of Human Factor VIII:C," Behring Institute Mitteilungen 82:16-25, Behringwerke AG, Germany (1988).
Lenting, P.J., et al., "Biochemistry of FVIII and Inhibitors: The Disappearing Act of Factor VIII," Haemophilia 16(102):6-15, Blackwell Publishing Ltd, England (2010).
Li, H., et al., "The role of the transferrin-transferrin-receptor system in drug delivery and targeting," Trends in Pharmacological Sciences 23(5):206-209, Elsevier Science Ltd., England (2002).
Linhult, M., et al., "Mutational Analysis of the Interaction Between Albumin-Binding Domain from Streptococcal Protein G and Human Serum Albumin," Protein Science 11(2):206-213, Cold Spring Harbor Laboratory Press, United States (2002).
Malik, F., et al., "Polyethylene Glycol (PEG)-modified Granulocyte-Macrophage Colony-stimulating Factor (GM-CSF) with Conserved Biological Activity," Experimental Hematology 20(8):1028-1035, International Society for Experimental Hematology, United States (1992).
Martinelli, N., et al., "Polymorphisms at LDLR Locus may be Associated with Coronary Artery Disease through Modulation of Coagulation Factor VIII Activity and Independently from Lipid Profile," Blood 116(25):5688-5697, The American Society of Hematology, United States (2010).
Mei, B., et al., "Expression of Human Coagulation Factor VIII in a Human Hybrid Cell Line, HKB11," Molecular Biotechnology 34(2):165-178, Humana Press Inc., United States (2006).
Mei, B., et al., "Rational Design of a Fully active, Long-Acting PEGylated Factor VIII for Hemophilia A Treatment," Blood 116(2):270-279, The American Society of Hematology, United States (2010).
Meulien, P., et al., "A New Recombinant Procoagulant Protein Derived from the cDNA Encoding Human Factor VIII," Protein Engineering 2(4):301-306, IRL Press Ltd., England (1988).
Muller, D. and Kontermann, R.E., "Recombinant Bispecific Antibodies for Cellular Cancer Immunotherapy," Current Opinion in Molecular Therapeutics 9(4):319-326, The Thomson Corporation, United States (2007).
Neumann, E., et al., "Gene Transfer into Mouse Lyoma Cells by Electroporation in High Electric Fields," The EMBO Journal 1(7):841-845, IRL Press Limited, England (1982).
Oganesyan, V., et al., "Structural Characterization of a Human Fc Fragment Engineered for Extended Serum Half-Life," Molecular Immunology 46(8-9):1750-1755, Elsevier Ltd., United Kingdom (2009).
Parker, C.J.R. and Hunter, J.M., "Relationship Between Volume of Distribution of Atracurium and Body Weight," British Journal of Anaesthesia 70(4):443-445, Oxford University Press, England (1993).
Ron, D., et al., "Expression of Biologically Active Recombinant Keratinocyte Growth Factor: Structure/Function Analysis of Amino-Terminal Truncation Mutants," The Journal of Biological Chemistry 268(4):2984-2988, American Society for Biochemistry and Molecular Biology, United States (1993).
Roovers, R.C., et al., "Efficient Inhibition of EGFR Signaling and of Tumour Growth by Antagonistic Anti-EGFR Nanobodies," Cancer Immunology, Immunotherapy 56(3):303-317, Springer Verlag, Germany (2007).
Roth, J. et al., "Expression of Polysialic Acid in Human Tumors and its Significance for Tumor Growth" in "Polysialic Acid: From Microbes to Man", Roth J., Rutishauser U., Troy F.A., eds., pp. 335-348, Birkhauser Verlag, Basel, Switzerland (1993).
Routledge, E.G., et al., "The Effect of Aglycosylation on the Immunogenicity of a Humanized Therapeutic CD3 Monoclonal Antibody," Transplantation 60(8):847-853, Lippincott Williams & Wilkins, United States (1995).
Sarver, N., et al., "Stable Expression of Recombinant Factor VIII Molecules Using a Bovine Papillomavirus Vector," DNA 6(6):553-564, Mary Ann Liebert, Inc., United States (1987).
Schlapschy, M., et al., "Fusion of a Recombinant Antibody Fragment with a Homo-amino-acid Polymer: Effects on Biophysical Properties and Prolonged Plasma Half-Life," Protein Engineering Design & Selection 20(6):273-284, Oxford University Press, England (2007).
Shapiro, A.D., et al., "Safety and Prolonged Biological Activity Following a Single Administration of a Recombinant Molecular Fusion of Native Human Coagulation Factor IX and the Fc Region of Immunoglobulin G (IgG) (rFIXFc) to Subjects with Hemophilia B," Haemophilia 16(Suppl. 4):30, Blackwell Publishing Ltd., England, Abstract 07FP07 (Jul. 2010).
Shapiro, A.D., "Recombinant factor IX-Fc fusion protein (rFIXFc) demonstrates safety and prolonged activity in a phase 1/2a study in hemophilia B patients," Blood 119(3):666-672, The American Society of Hematology, United States (2012).
Shields, R.L., et al., "High Resolution Mapping of the Binding Site on Human IgG1 for FcγRI, FcγRII, FcγRIII, and FcRn and Design of IgG1 Variants with Improved Binding to the FcγR," The Journal of Biological Chemistry 276(9):6591-6604, American Society for Biochemistry and Molecular Biology, United States (2001).
Sommermeyer, V.K., et al., "Klinisch Verwendete Hydroxyethylstarke: Physikalisch-Chemische Charakterisierung," Krankenhauspharmazie 8(8):271-278, Deutscher Apotheker Verlag, Birkenwaldstr, Germany (1987).

(56) References Cited

OTHER PUBLICATIONS

Story, C.M., et al., "A Major Histocompatibility Complex Class I-like Fc Receptor Cloned from Human Placenta: Possible Role in Transfer of Immunoglobulin G from Mother to Fetus," The Journal of Experimental Medicine 180(6):2377-2381, The Rockefeller University Press, United States (1994).

Wood, W.I., et al., "Expression of Active Human Factor VIII from Recombinant DNA Clones," Nature 312(5992):330-337, Nature Publishing Group, England (1984).

Sutjandra, L., et al., "Population Pharmacokinetic Meta-Analysis of Denosumab in Healthy Subjects and Postmenopausal Women with Osteopenia or Osteoporosis," Clinical Pharmacokinetics 50(12):793-807, ADIS Press, Switzerland (2011).

Toole, J.J., et al., "A Large Region (≈95 kDa) of Human Factor VIII is Dispensable for in vitro Procoagulant Activity," Proceedings of the National Academy of Sciences USA 83(16):5939-5942, National Academy of Sciences, United States (1986).

Toole, J.J., et al., "Molecular Cloning of a cDNA Encoding Human Antihaemophilic Factor," Nature 312(5992):342-347, Nature Publishing Group, England (1984).

Toutain, P.L. and Bousquet-Melou, A.,, "Volumes of Distribution," Journal of Veterinary Pharmacology and Therapeutics 27(6):441-453, Oxford, Blackwell Scientific, England (2004).

Trussel, S., et al., "New Strategy for the Extension of the Serum Half-Life of Antibody Fragments," Bioconjugate Chemistry 20(12):2286-2292, American Chemical Society, United States (2009).

Vaccaro, C., et al., "Engineering the Fc region of Immunoglobulin G to Modulate in vivo Antibody Levels," Nature Biotechnology 23(10):1283-1288, Nature America Publishing, United States (2005).

Vehar, G.A., et al., "Structure of Human Factor VIII," Nature 312(5992):337-342, Nature Publishing Group, England (1984).

Wakabayashi, H., et al., "Residues 110-126 in the A1 Domain of Factor VIII Contain a $Ca^{2+}$ Binding Site Required for Cofactor Activity," The Journal of Biological Chemistry 279(13):12677-12684, The American Society for Biochemistry and Molecular Biology, Inc., United States (2004).

Wang, Y., et al., "Receptor-Mediated Activation of a Proinsulin-Transferrin Fusion Protein in Hepatoma Cells," Journal of Controlled Release 155(3):386-392, Elsevier B.V., Netherlands (2011).

Ward, E.S. and Ghetie, V., "The Effector Functions of Immunoglobulins: Implications for Therapy," Therapeutic Immunology 2(2):77-94, Blackwell Science Ltd., England (1995).

Weidler, B., et al., "Pharmakokinetische Merkmale als Kriterien fur den klinischen Einsatz von Hydroxyethylstarke," Arzneimittel-Forschung 41(5):494-498, Editio Cantor, Germany (1991).

Wigler, M., et al., "Biochemical Transfer of Single-Copy Eucaryotic Genes Using Total Cellular DNA as Donor," Cell 14(3):725-731, Cell Press, United States (1978).

Morbidity and Mortality: 2012 Chart Book on Cardiovascular, Lung and Blood Disease, p. 5, National Heart, Lung, and Blood Institute, NIH.

Extended European Search Report for EP Application No. 13847770.8, European Patent Office, Munich, Germany, dated May 4, 2016, 4 pages.

\* cited by examiner

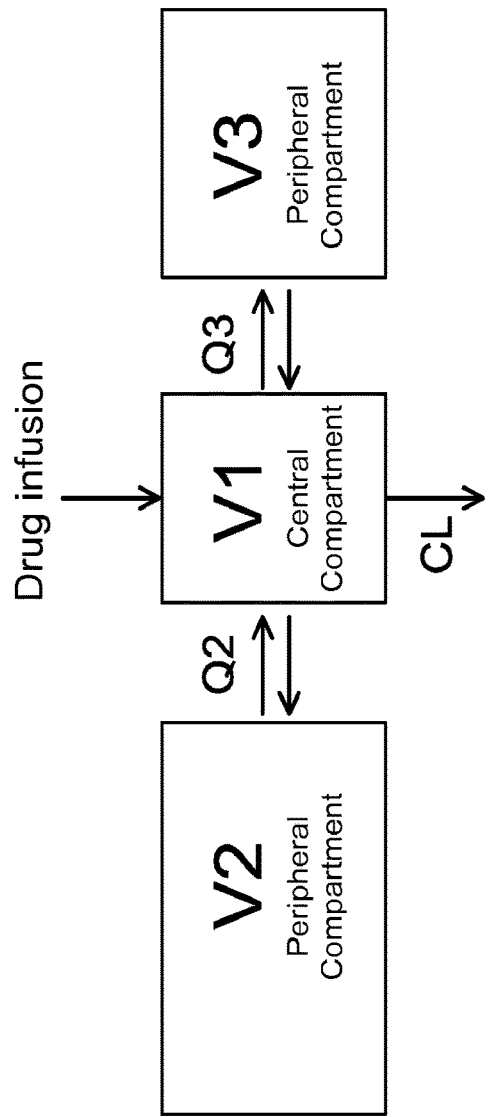
FIGURE 1. Three-compartment model for rFIXFc

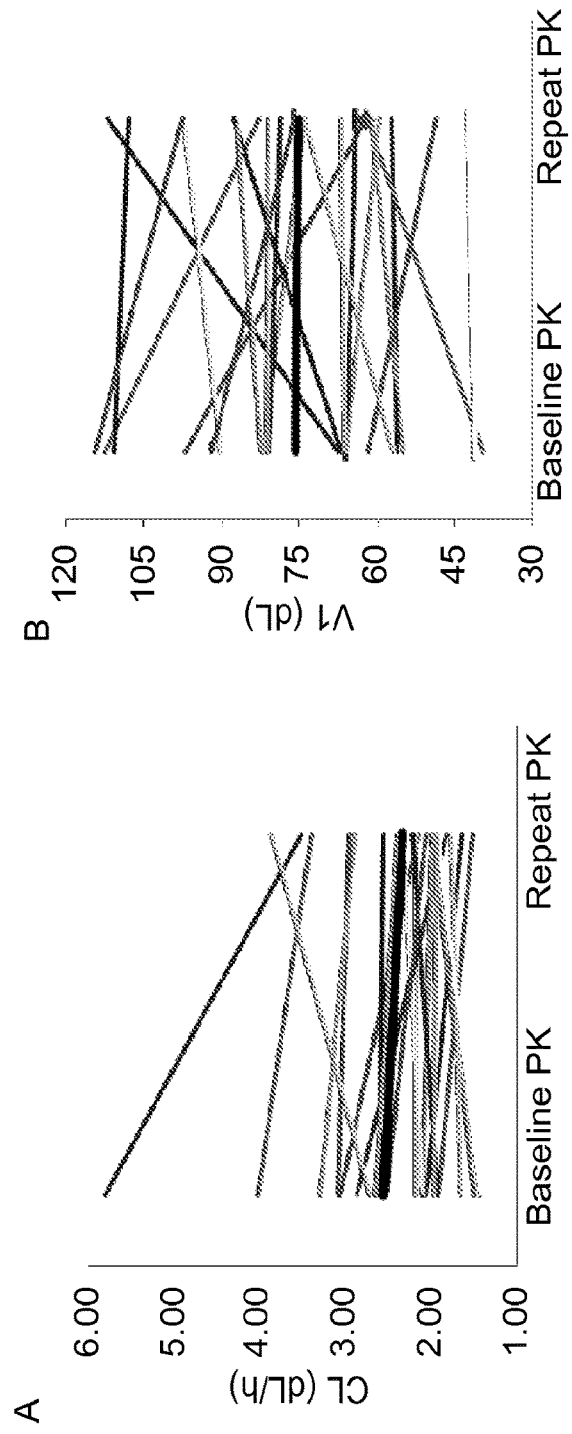
FIGURE 2. Clearance and V1 estimates of baseline (week 1) and repeat PK (week 26) profiles

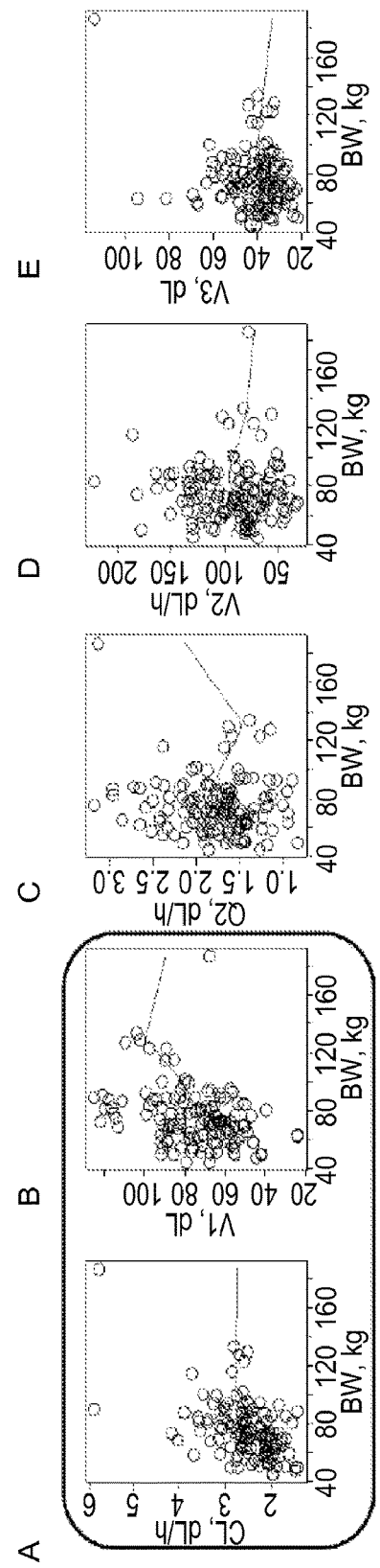
FIGURE 3. Individual PK parameters versus body weight (BW)

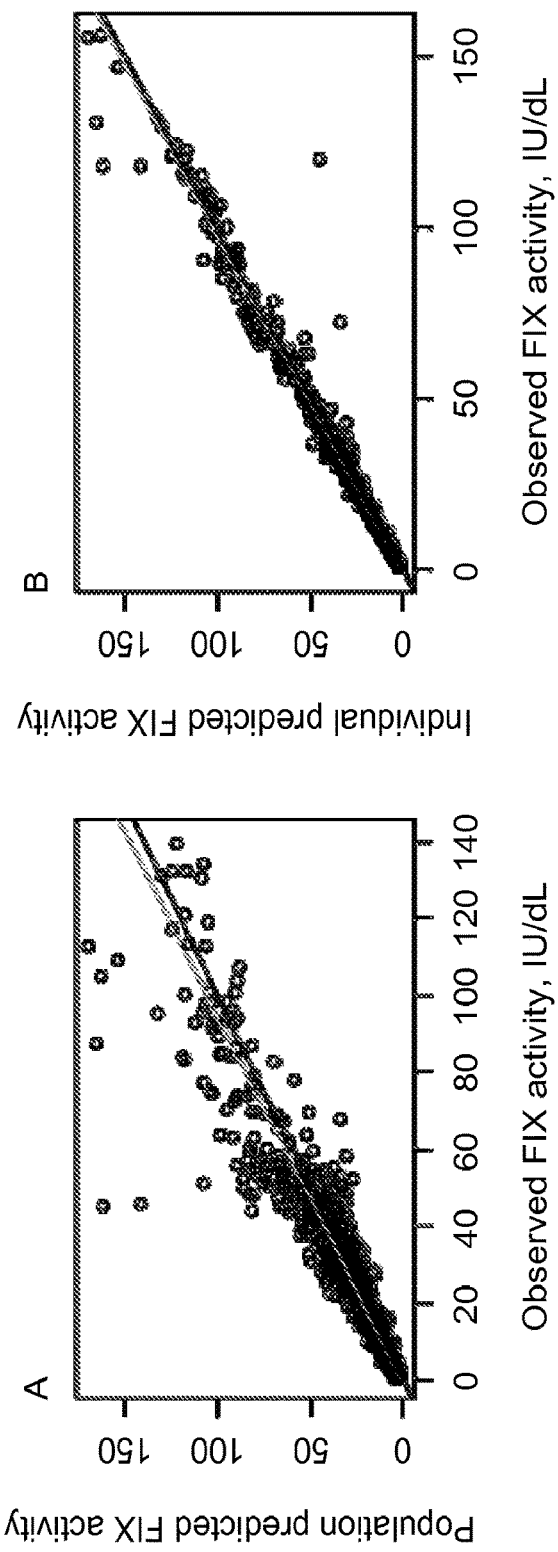
FIGURE 4. Goodness-of-fit plots of the population PK model

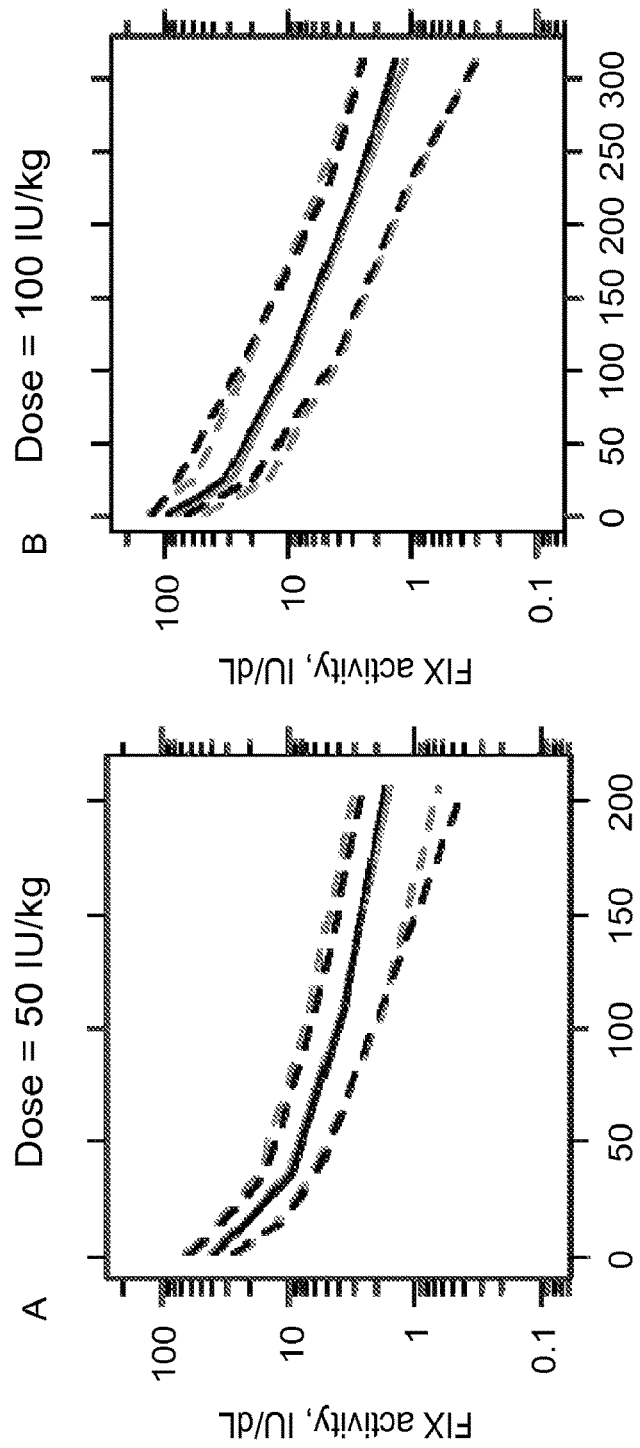
FIGURE 5. Visual Predictive Check (VPC) plots of the population PK model.

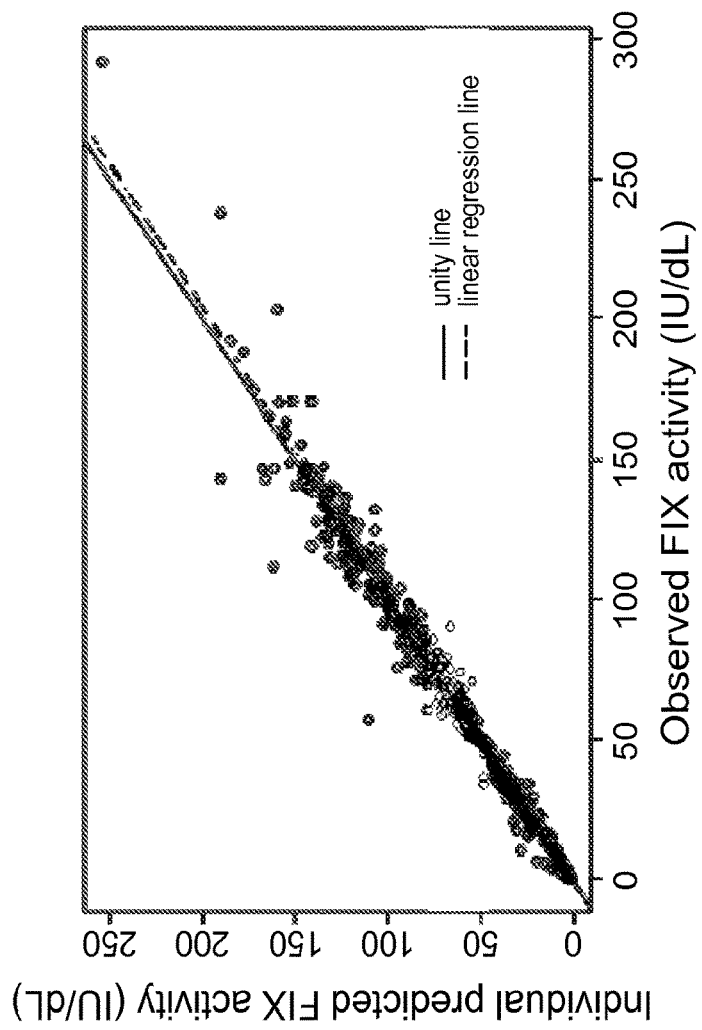
FIGURE 6. Validation of the population PK model with the trough/peak records.

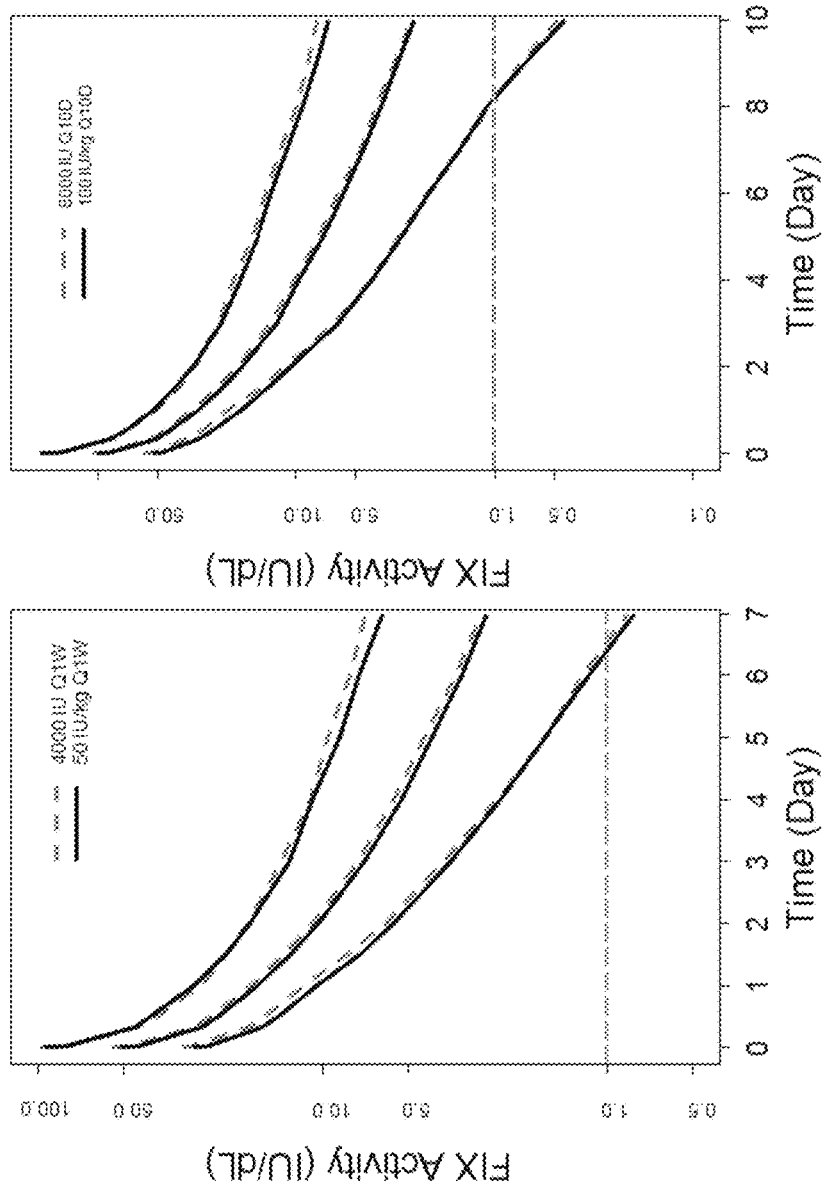
FIGURES 7A-7B. 97.5th, Median, and 2.5th Percentiles of Simulated FIX Activity-time Profiles at Steady State Following Fixed Dosing and BW-based Dosing FIGURE 8. Percentages of Population within the Target Therapeutic Range Following the Fixed Dosing or BW-based dosing approaches

| Performance evaluation metrics | | Once weekly | | Every 10 days | |
|---|---|---|---|---|---|
| | | 50 IU/kg | 4000 IU | 100 IU/kg | 8000 IU |
| Population with peak < 150% (%) | Low BW population | 100 | 100 | 98.5 | 73.3 |
| | Normal BW population | 100 | 100 | 90.6 | 86.8 |
| | High BW population | 98.7 | 100 | 52.4 | 96.9 |
| Population with trough ≥ 1% (%) | Low BW population | 94.3 | 99.1 | 89.5 | 96.5 |
| | Normal BW population | 95.4 | 95.5 | 89.0 | 90.5 |
| | High BW population | 95.9 | 83.2 | 88.8 | 70.5 |

METHODS OF USING A FIXED DOSE OF A CLOTTING FACTOR

REFERENCE TO SEQUENCE LISTING SUBMITTED ELECTRONICALLY VIA EFS-WEB

The content of the electronically submitted sequence listing (Name: 2159_400PC03_sequence.listing.ascii.txt, Size: 133,321 bytes; and Date of Creation: Oct. 18, 2013) was originally submitted in the International Application No. PCT/US2013/065772 and is incorporated herein by reference in its entirety.

BACKGROUND OF THE INVENTION

Field of the Invention

The present invention relates generally to the field of therapeutics for hemostatic disorders.

Background Art

While plasma-derived and recombinant clotting factor products allow hemophilia patients to live longer and healthier, hemophilia still remains one of the most costly and complex conditions to manage. The cost of clotting factor products exceeds $50,000 a year per patient. See Blankenship C. S., *Biotechnol. Healthc.* 2008, 5(4): 37-40. According to the National Heart, Lung, and Blood Institute, National Institute of Health (NIH), approximately 18,000 people in the U.S. have hemophilia, and 400 babies are born with the disease each year. Morbidity & Mortality: 2012 Chart Book on Cardiovascular, Lung and Blood Disease, page 5, National Heart, Lung, and Blood Institute, NIH. Due to its complexity, this chronic disease requires a special therapeutic management process for doctors, pharmacies, and patients. Clinicians often assess lifestyle, psychosocial requirements, and the home environment when evaluating a patient's or guardian's ability to provide adequate care.

In hemophilia, blood clotting is disturbed by a lack of certain plasma blood clotting factors. Hemophilia A, the most common form of hemophilia, is caused by Factor VIII deficiency. Hemophilia B is caused by decreased synthesis of Factor IX protein or synthesis of defective Factor IX having reduced activity. Treating hemophilia involves replacing missing or defective clotting factor with recombinant or plasma-derived FVIII or FIX. For patients who have developed antibodies against recombinant or plasma-derived FVIII or FIX, Factor VII can be used as a bypass therapy. Commercially available clotting factors are usually administered by peripheral intravenous injection. However, for patients with small veins or children who require frequent injections, clotting factors can be administered by a central venous access device. See Blankenship C. S., *Biotechnol. Healthc.* 2008, 5(4): 37-40.

Many biologics including clotting factors are administered based on patient body size. Body sized-based dosing is assumed to minimize inter-patient variability in pharmacokinetics (PK). Currently, three FIX products are approved by the Food and Drug Administration (FDA). The first, BENEFIX®, is a recombinant FIX product marketed by Pfizer. The second and third products are plasma-derived FIX products, ALPHANINE® marketed by Grifols and MONONINE® marketed by CSL Behring. According to their labels, these three products are dosed based on individual body weight. In particular, BENEFIX® is supplied as a lyophilized powder in five different dosages: 250 IU, 500 IU, 1000 IU, 2000 IU, and 3000 IU. MONONINE® is supplied as a single dose vial with Sterile Water for Injection at 500 IU and 1000 IU. ALPHANINE is supplied in lyophilized form as single doses at 500 IU, 1000 IU, and 1500 IU. The FIX dose required for each patient is calculated based on the formula:

Number of factor IX IU required (IU)=Body Weight (kg)×Desired Factor IX Increase (% or IU/dL)× Reciprocal of Observed Recovery (IU/kg per IU/dL)     (A)

Several Factor VIII products are also commercially available, which include recombinant FVIII products (ADVATE® and RECOMBINATE® marketed by Baxter, KOGENATE® FS marketed by Bayer, HELIXATE® FS marketed by CSL-Behring, and XYNTHA® and REFACTO® marketed by PFIZER) and Plasma-derived FVIII products (HEMOFIL-M® marketed by Baxter, MONARC-M® by American Red Cross, and MONOCLATE-P® marketed by CSL Behring). The required FVIII dose for each patient is calculated using the following formula:

Number of factor FVIII IU required (IU)=Body Weight (kg)×Desired Factor FVIII Increase (IU/dL or % of normal)×0.5(IU/kg per IU/dL)     (B)

A Factor VII product, NOVOSEVEN® marketed by Novo Nordisk, is also commercially available. The dosages of NOVOSEVEN® are also calculated based on body weight: 90 g/kg bolus injection every two hours for Hemophilia A or B with inhibitors, 15-30 g/kg every 4-6 hours for congenital FVII deficiency, or 70-90 g/kg every 2-3 hours for acquired hemophilia. See NOVOSEVEN® label, page 1, January 2010, version 3, Novo Nordisk A/S.

However, administering clotting factors via body weight-based dosing can be inconvenient and costly for patients. The invention as described herein provides improved clotting factor-dosing strategies.

BRIEF SUMMARY OF THE INVENTION

In certain embodiments, the present invention provides a method of providing a clotting factor comprising administering a fixed dose of a clotting factor to a subject in need thereof. In certain embodiments, a method of reducing, ameliorating, or preventing one or more symptoms of a bleeding disease or disorder in a subject comprising administering a fixed dose of a clotting factor to a subject in need thereof is provided. In some aspects, the clotting factor is a modified clotting factor. In some embodiments, the modified clotting factor comprises a clotting factor and a heterologous moiety, e.g., a heterologous moiety which increases in vivo half-life of the clotting factor. In some aspects the heterologous moiety is a non-polypeptide moiety or a polypeptide moiety. In certain aspects, the heterologous moiety comprises albumin, albumin binding polypeptide, an FcRn binding partner, PAS, the C-terminal peptide (CTP) of the β subunit of human chorionic gonadotropin, polyethylene glycol (PEG), hydroxyethyl starch (HES), albumin-binding small molecules, or combinations thereof. In certain aspects, the modified clotting factor is a long-acting clotting factor.

In some embodiments, the fixed dose of a clotting factor is administered at regular intervals of every day, every two days, every three days, twice a week, every four days, every five days, every six days, every week, every eight days, every nine days, every 10 days, every 11 days, every 12 days, every 13 days, every two weeks, every three weeks, or every four weeks. In certain embodiments, the fixed dose is administered as needed to control bleeding.

In some aspects, the clotting factor has a wide therapeutic window. For example, the therapeutic window for the clotting factor can be a maximum serum concentration ($C_{max}$) of about 150% of normal and a minimum serum concentration ($C_{min}$) of about 1% of normal.

In other aspects, the clotting factor has a narrow therapeutic window.

In certain embodiments provided herein, the body weight effect on clearance ($\theta_{BW\_CL}$) of the clotting factor is equal to or less than about 0.75, 0.74, 0.73, 0.72, 0.71, 0.70, 0.69, 0.68, about 0.65, about 0.60, about 0.59, about 0.58, about 0.57, about 0.56, about 0.55, about 0.54, about 0.53, about 0.52, about 0.51, about 0.50, about 0.49, about 0.48, about 0.47, about 0.46, about 0.45, about 0.44, about 0.43, about 0.42, about 0.41, about 0.40, about 0.35, about 0.30, about 0.25, about 0.20, about 0.15, about 0.10, about 0.05, or about 0. Alternatively, or in addition, the body weight effect on the central volume of distribution ($\theta_{BW\_V1}$) of the clotting factor is equal to or less than about 0.75, 0.74, 0.73, 0.72, 0.71, 0.70, 0.69, 0.68, about 0.65, about 0.60, about 0.59, about 0.58, about 0.57, about 0.56, about 0.55, about 0.54, about 0.53, about 0.52, about 0.51, about 0.50, about 0.49, about 0.48, about 0.47, about 0.46, about 0.45, about 0.44, about 0.43, about 0.42, about 0.41, about 0.40, about 0.35, about 0.30, about 0.25, about 0.20, about 0.15, about 0.10, about 0.05, or about 0.

In specific embodiments, the $\theta_{BW\_CL}$ of the clotting factor is equal to or less than about 0.500 and/or the $\theta_{BW\_V1}$ of the clotting factor is equal to or less than about 0.467. For example, in some embodiments the $\theta_{BW\_CL}$ of the clotting factor is about 0.500 and/or the $\theta_{BW\_V1}$ of the clotting factor is about 0.467.

In some embodiments of the method provided herein the body weight of the subject does not produce pharmacodynamic variability within subjects. In other aspects, administration of a fixed dose of the clotting factor results in reduced variability of pharmacokinetic parameters across all body weights as compared to administration of a body weight-based dose of the clotting factor. For example, in certain embodiments the pharmacokinetic parameter is area under the curve (AUC) and variability in AUC for a fixed dose of the clotting factor is less than ±50%, less than ±45%, less than ±40%, less than ±35%, less than ±30%, or less than ±25% across all body weights.

In certain aspects of the method provided herein the clotting factor is a long-acting FIX polypeptide. The long-acting FIX polypeptide can include a FIX polypeptide and an FcRn binding partner, and the FcRn binding partner can include an Fc region. The long-acting FIX polypeptide can further include a second FcRn binding partner, which can include a second Fc region. In certain aspects the FcRn binding partner and the second FcRn binding partner are associated, e.g., by a covalent bond, e.g., by a disulfide bond. In other aspects the second FcRn binding partner is not linked to an amino acid sequence by a peptide bond. In certain embodiments, the long-acting FIX polypeptide is FIX monomer dimer hybrid.

According to the present disclosure, the fixed dose of a long acting FIX polypeptide can be standard across all body weights, e.g., about 4000 IU per dose which is, e.g., administered weekly, or about 8000 IU which is, e.g., administered weekly. In other embodiments, the fixed dose is administered every 10 days.

In certain aspects a fixed dose of a long acting FIX polypeptide is stratified into multiple (e.g., two or more) fixed dose amounts based on specified weight categories, such as low body weight, normal body weight, and high body weight. For example, the fixed dose can be stratified into three fixed dose amounts suitable for subjects with low, normal, or high body weight. In one embodiment, the normal, low, or high body weight is determined based on age, height, gender, frame size, general health, or any combination thereof. In another embodiment, the normal, low, or high body weight is determined independently of age, height, gender, frame size, general health, or any combination thereof. In other embodiments, the normal body weight for a human subject is between about 50±10 kg and about 100±10 kg. In some embodiments, the low body weight for a human subject is less than about 50±10 kg. In still other embodiments, the high body weight for a human subject is greater than about 100±10 kg.

In some aspects, the fixed dose is administered weekly (i.e., once a week). In other aspects, the fixed dose is administered every 10 days. In one embodiment, the subject has a low body weight and the fixed dose is about 5000 IU per dose administered every 10 days or about 6000 IU per dose administered every 10 days. In another embodiment, the subject has a normal body weight and the fixed dose is about 7500 IU per dose administered every 10 days or about 8000 IU per dose administered every 10 days. In other embodiments, the subject has a high body weight and the fixed dose is about 10000 IU per dose administered every 10 days or about 12000 IU per dose administered every 10 days.

In further aspects, the clotting factor is a long-acting FVIII polypeptide. For example, the long-acting FVIII polypeptide comprises a FVIII polypeptide and an FcRn binding partner, e.g., an Fc region. In some embodiments, the long-acting FVIII polypeptide further comprises a second FcRn binding partner, e.g., a second Fc region. In one example, the FcRn binding partner and the second FcRn binding partner are associated, e.g., by a covalent bond, e.g., a disulfide bond. In another example, the long-acting FVIII polypeptide is FVIII monomer dimer hybrid. In other examples, the FVIII polypeptide in the long-acting polypeptide is a full-length FVIII or a B-domain deleted FVIII.

In one aspect, the fixed dose is standard across all body weights. In one embodiment, the fixed dose is administered twice weekly. In another embodiment, the fixed dose is administered weekly. In other embodiments, the fixed dose is stratified into multiple (e.g., two or more) dose amounts based on specified weight categories, e.g., low body weight, normal body weight, and high body weight. In other embodiments, the fixed dose is stratified into three dose sizes suitable for subjects with low, normal, or high body weight. In some embodiments, the normal, low, or high body weight is determined based on age, height, gender, frame size, general health, or any combination thereof. In other embodiments, the low, normal, or high body weight is determined independently of age, height, gender, frame size, general health, or any combination thereof. In one aspect, the normal body weight for a human subject is between about 50±10 kg and about 100±10 kg. In another aspect, the low body weight for a human subject is less than about 50±10 kg. In other aspects, the high body weight for a human subject is greater than about 100±10 kg. In one example, the fixed dose for the long-acting FVIII polypeptide is administered twice weekly at about 2000 IU, about 2,500 IU, about 3,000 IU, about 3,500 IU, or about 4,000 IU. In another example, the fixed dose is administered weekly.

In some aspects, the fixed dose of the clotting factor is to prevent one or more bleeding episodes. In one embodiment, the fixed dose of the clotting factor is for individualized interval prophylaxis of a bleeding episode. In another embodiment, the fixed dose of the clotting factor is for on-demand or episodic treatment of a bleeding episode. In other embodiments, the fixed dose of the clotting factor is for perioperative management of a bleeding episode. In certain embodiments, the subject is in need of controlling or preventing bleeding or bleeding episodes, for example, in need of peri-operative management or in need of management of bleeding associated with surgery or dental extraction. In some embodiments, the subject will undergo, is undergoing, or has undergone major surgery. In certain embodiments, the subject is in need of prophylactic treatment or in need of on-demand treatment.

In other aspects, the fixed dose is provided in a single container (e.g., vial) or in two or more containers (e.g., vials), the total contents of which provide the fixed dosage amount.

The invention also includes use of a fixed dosage of a clotting factor for the manufacture of a medicament for reducing, ameliorating, or preventing one or more symptoms of a bleeding disease or disorder in a subject in need thereof. The medicament can be administered according to the method described herein.

Further included is a fixed dosage of a modified clotting factor for use in reducing, ameliorating, or preventing one or more symptoms of a bleeding disease or disorder in a subject in need thereof. The fixed dosage of the invention is suitable for administration according to the method described herein.

The present invention also includes a pharmaceutical composition comprising a fixed dose of a modified clotting factor and a pharmaceutically acceptable carrier for use to reduce, ameliorate, or prevent one or more symptoms of a bleeding disease or disorder in a subject in need thereof. The pharmaceutical composition is suitable for administration according to the method described herein.

The present invention further includes a kit comprising the pharmaceutical composition described herein and instructions to administer the fixed dose of the clotting factor to the subject. In one embodiment, the entire fixed dose is administered. In another embodiment, the fixed dose is provided in a single container (e.g., vial). In other embodiments, the fixed dose is provided in two or more containers (e.g., vials), the total contents of which provide the fixed dosage.

BRIEF DESCRIPTION OF THE DRAWINGS

FIG. 1 shows a diagram of the three-compartment model for predicting population PK for rFIXFc. CL, clearance; V, volume of distribution; Q, inter-compartmental clearance. V1 shows volume of distribution in central compartment; and V2 and V3 show volume of distribution in peripheral compartments. Q2 is inter-compartmental clearance between V1 and V2. Q3 is inter-compartmental clearance between V1 and V3.

FIG. 2A shows clearance (CL) estimates of baseline (week 1) and repeat PK (week 26) profiles. FIG. 2B shows Volume of Distribution of central compartment (V1) estimates of baseline (week 1) and repeat PK (week 26) profiles. The thick line in the middle of FIGS. 2A and 2B indicates mean, which did not change much between two occasions.

FIGS. 3A to 3E show individual PK parameters versus body weight (BW). FIG. 3A shows clearance in dL/h. FIG. 3B shows Volume of Distribution of central compartment (V1) in dL. FIG. 3C shows inter-compartmental clearance (Q2) in dL/h. FIG. 3D shows Volume of Distribution in a peripheral compartment (V2) in dL/h. FIG. 3E shows Volume of Distribution of a peripheral compartment (V3).

FIG. 4A shows goodness-of-fit plots of FIX activity predicted by the population PK model compared to observed FIX activity. FIG. 4B shows goodness-of-fit plots of FIX activity predicted by the individual PK model compared to observed FIX activity.

FIG. 5A shows Visual Predictive Check (VPC) plots of the population PK model for 50 IU/kg dose. FIG. 5B shows VPC plots of the population PK model for 100 IU/kg dose. Gray and black lines represent 10th, 50th, and 90th percentile of the simulated (gray) and observed (black) data, respectively.

FIG. 6 shows validation of the population PK model with the trough/peak records. R2=0.9857, P<0.001.

FIG. 7A shows the $97.5^{th}$, median, and $2.5^{th}$ percentiles of the simulated FIX activity-time profiles at steady state in 1000 subjects following fixed dosing (4000 IU once weekly; dotted line) compared with the $97.5^{th}$, median, and $2.5^{th}$ percentiles of the simulated FIX activity-time profiles at steady state in 1000 subjects following BW-based dosing (50 IU/kg once weekly; solid line). FIG. 7B shows the $97.5^{th}$ median, and $2.5^{th}$ percentiles of the simulated FIX activity-time profiles at steady state in 1000 subjects following fixed dosing (8000 IU every 10 days) compared with the $97.5^{th}$, median, and $2.5^{th}$ percentiles of the simulated FIX activity-time profiles at steady state in 1000 subjects following BW-based dosing (100 IU/kg every 10 days; solid lines).

FIG. 8 shows the percentiles of population within the target therapeutic range following the fixed dosing and BW-based dosing approaches in the BW-stratified populations.

DETAILED DESCRIPTION OF THE INVENTION

The present invention is derived from the recognition that a fixed dosing regimen can be suitable for a clotting factor. The present invention thus provides a method of administering a fixed dose of a clotting factor to a subject in need thereof or a population of two or more subjects in need thereof. Administration of the fixed dose of the clotting factor can reduce, ameliorate, or prevent one or more symptoms of a bleeding disease or disorder. For example, administration of the fixed dose of the clotting factor can control or prevent a bleeding episode. The invention also includes a kit comprising one or more pharmaceutical compositions and an instruction manual, wherein the one or more pharmaceutical composition comprises a fixed dose of a clotting factor.

I. DEFINITIONS

It must be noted that, as used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

It is understood that wherever embodiments are described herein with the language "comprising," otherwise analogous embodiments described in terms of "consisting of" and/or "consisting essentially of" are also provided.

The term "polypeptide," "peptide" and "protein" are used interchangeably and refer to a polymeric compound comprised of covalently linked amino acid residues.

The term "polynucleotide" and "nucleic acid" are used interchangeably and refer to a polymeric compound comprised of covalently linked nucleotide residues. Polynucleotides may be DNA, cDNA, RNA, single stranded, or double stranded, vectors, plasmids, phage, or viruses. Polynucleotides include, but are not limited to, those in Tables 4 and 6, which encode the polypeptides of Table 5 and 7. Polynucleotides also include fragments, variants, analogues, or derivatives of the polynucleotides of Tables 4 and 6, e.g., those that encode fragments of the polypeptides of Table 5, 7, or 8.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systéme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the disclosure, which can be had by reference to the specification as a whole. Accordingly, the terms defined immediately below are more fully defined by reference to the specification in its entirety. Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

An "isolated" polypeptide, antibody, polynucleotide, vector, cell, or composition refers to a polypeptide, antibody, polynucleotide, vector, cell, or composition that is in a form not found in nature. Isolated polypeptides, antibodies, polynucleotides, vectors, cells or compositions include those which have been purified to a degree that they are no longer in a form in which they are found in nature. In some aspects, an antibody, polynucleotide, vector, cell, or composition that is isolated is substantially pure. In some aspects an antibody, polynucleotide, vector, cell, or composition that is isolated is "recombinant."

The term "administering," as used herein, means to prescribe or to give a pharmaceutically acceptable clotting factor to a subject via a pharmaceutically acceptable route. Examples of routes of administration include, but are not limited to, intravenous, e.g., intravenous injection and intravenous infusion, e.g., via central venous access. Additional routes of administration include subcutaneous, intramuscular, oral, nasal, and pulmonary administration. A clotting factor (e.g., a FIX or FVIII or modified clotting factor protein) may be administered as part of a pharmaceutical composition comprising at least one excipient.

The term "modified clotting factor" as used herein means a clotting factor sequence that is modified in the polypeptide or polynucleotide sequence by deletion, substitution, insertion, conjugation, linkage, fusion, glycosylation, or any types of modifications that are not present in the polypeptide sequences in the wild-type clotting factor (e.g., FIX or FVIII) or the commercially available clotting factor (e.g., REFACTO® or XYNTHA® for SQ BDD FVIII; RECOMBINATE®, ADVATE®, OR HELIXATE® for full-length FVIII; or BENEFIX®, ALPHANINE®, or MONONINE® for FIX).

The terms "long-acting" and "long-lasting" are used interchangeably herein. In one embodiment, the term "long-acting" or "long-lasting" indicates that the clotting activity as a result of administration of a "long-acting" clotting factor is longer than the clotting activity of a wild-type clotting factor (also referred to as "short acting" or "shorter acting" clotting factor) (e.g., BENEFIX® or plasma-derived FIX ("pdFIX") for FIX, or SQ B domain deleted FVIII (e.g., REFACTO®) or mature full-length FVIII, e.g., RECOMBINATE®, for FVIII). The "longer" clotting activity can be measured by any known methods in the art, e.g., aPTT assay, chromogenic assay, ROTEM, TGA, and etc. In one embodiment, the "longer" clotting activity can be shown by the $T_{1/2beta}$ (activity). In another embodiment, the "longer" clotting activity can be shown the level of the clotting factor present in plasma, e.g., by the $T_{1/2beta}$ (antigen). In other embodiments, the long-acting or long-lasting clotting factor works longer in a coagulation cascade, e.g., is active for a longer period, compared to a wild-type clotting factor (e.g., BENEFIX® or plasma-derived FIX ("pdFIX") for FIX or SQ B domain deleted FVIII (e.g., REFACTO®) or mature full-length FVIII, e.g., RECOMBINATE®, for FVIII). The long-acting or long-lasting clotting factor can comprise one or more heterologous moieties that extend in vivo half-life of the clotting factor. Examples of the heterologous moieties are described below.

The term "chimeric clotting factor" as used herein, means a polypeptide that includes within it at least two polypeptides (or portions thereof such as subsequences or peptides) from different sources. Chimeric clotting factor can include two, three, four, five, six, seven, or more polypeptides or portions thereof from different sources, such as different genes, different cDNAs, or different animal or other species. Chimeric clotting factors can include one or more linkers joining the different polypeptides or portions thereof. Thus, the polypeptides or portions thereof can be joined directly or they may be joined indirectly, via linkers, or both, within a single chimeric polypeptide. In certain embodiments, chimeric clotting factors can include additional peptides such as signal sequences and sequences such as 6His and FLAG that aid in protein purification or detection. In addition, chimeric clotting factors can have amino acid or peptide additions to the N- and/or C-termini. Exemplary chimeric clotting factors of the invention are Factor IX-Fc chimeric polypeptides or FVIII-Fc chimeric polypeptides.

"Dosing interval," as used herein, means the amount of time that elapses between multiple doses being administered to a subject. Dosing interval can thus be indicated as a range. The dosing interval in the methods of the invention using a clotting factor can depend on the specific clotting factor. For example, a dosing interval of a long-acting clotting factor can be at least about one and a quarter, at least one and one-half to ten times longer than the dosing interval required for an equivalent amount (in IU/kg) of the wild-type clotting factor (i.e., a short-acting clotting factor). The dosing interval when administering, e.g., a Factor IX-Fc chimeric polypeptide (or a hybrid) of the invention can be at least about three times longer than the dosing interval required for an equivalent amount of said Factor IX without the FcRn BP (defined below), e.g., Fc, portion (i.e., a polypeptide consisting of said Factor IX). The dosing interval when administering, e.g., a Factor VIII-Fc chimeric polypeptide (or a hybrid) of the invention can be at least about one and a quarter, at least one and one-half times longer than the dosing interval required for an equivalent amount of the FVIII without the FcRn BP, e.g., Fc, portion (i.e., a polypeptide consisting of the FVIII). The dosing interval may be at least about one and one-half to fifteen times longer than the dosing interval required for an equivalent amount of the FIX or FVIII without, e.g., the Fc portion (or a polypeptide consisting of the FIX or FVIII portion).

The term "dosing frequency" as used herein refers to the frequency of administering doses of a clotting factor in a given time. Dosing frequency can be indicated as the number of doses per a given time, e.g., once a week or once in two weeks.

"Therapeutic dose," "dose," "effective dose," or "dosing amount" as used herein, means a dose that achieves a plasma trough level of a clotting activity at least about 1 IU/dl or above in the subject administered with the clotting factor. For the purpose of this invention, a "dose" can refer to the amount of the clotting factor required to maintain a plasma trough level of a clotting activity of at least about 1 IU/dl or above 1 IU/dl, at least about 2 IU/dl or above 2 IU/dl, at least about 3 IU/dl or above 3 IU/dl, at least about 4 IU/dl or above 4 IU/dl, at least about 5 IU/dl or above 5 IU/dl, at least about 6 IU/dl or above 6 IU/dl, at least about 7 IU/dl or above 7 IU/dl, at least about 8 IU/dl or above 8 IU/dl, at least about 9 IU/dl or above 9 IU/dl, at least about 10 IU/dl or above 10 IU/dl, at least about 11 IU/dl or above 11 IU/dl, at least about 12 IU/dl or above 12 IU/dl, at least about 13 IU/dl or above 13 IU/dl, at least about 14 IU/dl or above 14 IU/dl, at least about 15 IU/dl or above 15 IU/dl, or at least about 20 IU/dl or above 20 IU/dl, throughout the administration of the clotting factor. In another embodiment, the "dose" reduces or decreases the frequency of bleeding or symptoms of a bleeding disorder. In other embodiments, the "dose" stops on-going, uncontrollable bleeding or bleeding episodes. In still other embodiments, the "dose" prevents spontaneous bleeding or bleeding episodes in a subject susceptible to such spontaneous bleeding or bleeding episodes. The "dose" or "therapeutic dose" need not cure hemophilia.

The term "fixed dosing" or "fixed dose" as used herein means a dosing amount given to a subject regardless of the body weight, or who have a body weight within a given range. In one example, a fixed dose can be given to any subjects in need thereof whether they have a low body weight (e.g., lower than $10^{th}$ percentile of a body distribution), a normal body weight (e.g., between $10^{th}$ percentile and $90^{th}$ percentile of a body weight distribution), or a high body weight (e.g., higher than $90^{th}$ percentile of a body weight distribution). In another example, fixed dosing can be stratified over two or more patient populations. For example, a first fixed dose can be given to a subject having a low extreme body weight (e.g., lower than $10^{th}$ percentile of a body weight distribution); a second fixed dose can be given to a subject having a normal or high extreme body weight (e.g., equal to or higher than $10^{th}$ percentile of a body weight distribution). In another example, fixed dosing can be stratified over three or more groups, for example a first fixed dose can be given to subjects having a low body weight (e.g., lower than $10^{th}$ percentile of a body weight distribution); a second fixed dose can be given to subjects having a normal or high body weight (e.g., equal to or higher than $10^{th}$ percentile of a body weight distribution), and a third fixed dose can be given to subjects having a high body weight (e.g., higher than $90^{th}$ percentile of a body weight distribution).

The fixed dosing regimen can be stratified into two or more fixed dose amounts based on specified weight categories. In one embodiment, the weight categories are low body weight, normal body weight, and high body weight. For example, the fixed dose can be stratified into multiple fixed dose amounts (e.g., three) suitable for subjects who fall within the weight categories, e.g., those with low, normal, or high body weight. The ranges of each body weight can be determined based on the patient's age, gender, frame size, height, general health, or any combinations thereof or independently of age, height, gender, frame size, general health, or any combination there. A person of ordinary skill in the art can assess the factors related to body weight and can determine the specific body weight category for a subject.

The phrase "normal body weight" as used herein means a body weight of a typical individual. Therefore, the phrase "normal body weight" is used interchangeably with the phase "typical body weight." In one example, a subject having a normal body weight is neither obese nor underweight. In another example, a subject having a normal body weight has a body weight between about 50 kg±10 kg and about 110 kg±10 kg. In a particular example, a subject having a normal body weight has a body weight between 57 kg and 104 kg. The normal body weight is above a low body weight and below a high body weight.

The phrase "low body weight" as used herein means a body weight that is lower than the body weight of a typical individual. In one example, a subject having a low body weight is underweight. In another example, a subject having a low body weight has a body weight lower than about 50 kg±10 kg. In other embodiments, a low body weight is a low extreme body weight. In a particular example, a subject having a low body weight has a body weight lower than about 57 kg.

The phrase "high body weight" as used herein means a body weight that is higher than the body weight of typical individual. In one example, a subject having a high body weight is obese. In another example, a subject having a high body weight has a body weight higher than about 110 kg±10 kg. In other embodiments, a high body weight is a high extreme body weight. In a particular example, a subject having a high body weight has a body weight higher than about 104 kg.

The term "prophylaxis of one or more bleeding episodes," "prevent one or more bleeding episodes" or "prophylactic treatment" as used herein means administering a clotting factor in fixed doses to a subject over a course of time to increase the level of clotting activity in a subject's plasma. In one embodiment, "prophylaxis of one or more bleeding episodes" or "prevent one or more bleeding episodes" indicates use of a clotting factor to prevent or inhibit occurrence of one or more spontaneous or uncontrollable bleeding or bleeding episodes or to reduce the frequency of one or more spontaneous or uncontrollable bleeding or bleeding episodes. "Routine prophylaxis" is used to prevent or reduce the frequency of bleeding episodes in subjects with hemophilia A or B. In another embodiment, the increased clotting activity level is sufficient to decrease the incidence of spontaneous bleeding or to prevent bleeding in the event of an unforeseen injury. Prophylactic treatment decreases or prevents bleeding episodes, for example, those described under on-demand treatment.

The term "about once a week" as used herein means approximate number, and "about once a week" can include every seven days±two days, i.e., every five days to every nine days. The dosing frequency of "once a week" thus can be every five days, every six days, every seven days, every eight days, or every nine days.

The term "individualized interval prophylaxis" as used herein means use of a long-acting clotting factor for an individualized dosing interval or frequency for a subject to prevent or inhibit occurrence of one or more spontaneous and/or uncontrollable bleeding or bleeding episodes or to reduce the frequency of one or more spontaneous and/or uncontrollable bleeding or bleeding episodes to the subject. In one embodiment, the "individualized interval" includes every 10 days±3 days, i.e. every seven days to every 13 days. The dosing frequency of the "individualized interval prophylaxis" thus can be every seven days, every eight days, every nine days, every ten days, every 11 days, every 12 days, or every 13 days.

The term "on-demand treatment," as used herein, means treatment that is intended to take place over a short course of time and is in response to an existing condition, such as a bleeding episode, or a perceived short term need such as planned surgery. The "on-demand treatment" is used interchangeably with "episodic" treatment. Conditions that may require on-demand treatment include a bleeding episode, hemarthrosis, muscle bleed, oral bleed, hemorrhage, hemorrhage into muscles, oral hemorrhage, trauma, trauma capitis, gastrointestinal bleeding, intracranial hemorrhage, intra-abdominal hemorrhage, intrathoracic hemorrhage, bone fracture, central nervous system bleeding, bleeding in the retropharyngeal space, bleeding in the retroperitoneal space, or bleeding in the illiopsoas sheath. Bleeding episodes other than these known in the art are also included. The subject can be in need of surgical prophylaxis, perioperative management, or treatment for surgery. Such surgeries include, but are not limited to, minor surgery, major surgery, tooth extraction, tonsillectomy, other dental/thoraco-facial surgeries, inguinal herniotomy, synovectomy, total knee replacement, other joint replacement, craniotomy, osteosynthesis, trauma surgery, intracranial surgery, intra-abdominal surgery, intrathoracic surgery. Surgeries other than these are also included.

Additional non-limiting conditions that can require on-demand treatment include minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Additional reasons for on-demand treatment include the need for peri-operative management for surgery or dental extraction, major surgery, extensive oral surgery, urologic surgery, hernia surgery, orthopedic surgery such as replacement of knee, hip, or other major joint.

The term "treatment" or "treating" as used herein means amelioration or reduction of one or more symptoms of bleeding diseases or disorders including, but not limited to, hemophilia A or hemophilia B. In one embodiment, "treatment of" or "treating" a bleeding disease or disorder includes prevention of one or more symptoms of a bleeding disease or disorder. In a bleeding disease or disorder caused by a clotting factor deficiency (e.g., a low baseline clotting activity), the term "treatment" or "treating" means a clotting factor replacement therapy. By administering a clotting factor to a subject, the subject can achieve and/or maintain a plasma trough level of a clotting activity at about 1 IU/dl or above 1 IU/dl. In other embodiments, "treatment" or "treating" means reduction of the frequency of one or more symptoms of bleeding diseases or disorders, e.g., spontaneous or uncontrollable bleeding episodes. "Treatment," however, need not be a cure.

The term "perioperative management" as used herein means use of a clotting factor before, concurrently with, or after an operative procedure, e.g., a surgical operation. The use for "perioperative management" of one or more bleeding episode includes surgical prophylaxis before (i.e., preoperative), during (i.e., intraoperative), or after (i.e., postoperative) a surgery to prevent one or more bleeding or bleeding episode or reducing or inhibiting spontaneous and/or uncontrollable bleeding episodes before, during, and after a surgery.

Pharmacokinetic (PK) parameters include the terms above and the following terms, which have their ordinary meaning in the art, unless otherwise indicated. Some of the terms are explained in more detail in the Examples. PK parameters can be based on clotting factor antigen level (often denoted parenthetically herein as "antigen") or clotting activity level (often denoted parenthetically herein as "activity"). In the literature, PK parameters are often based on clotting activity level due to the presence in the plasma of some patients of endogenous, inactive clotting factor, which interferes with the ability to measure administered (i.e., exogenous) clotting factor using antibody against clotting factor. However, when a clotting factor is administered, clotting factor antigen can be accurately measured using antibody to the heterologous polypeptide. In addition, certain PK parameters can be based on model predicted data (often denoted parenthetically herein as "model predicted") or on observed data (often denoted parenthetically herein as "observed").

"Baseline," as used herein, is the lowest measured plasma clotting factor level in a subject prior to administering a dose. The clotting factor plasma levels can be measured at two time points prior to dosing: at a screening visit and immediately prior to dosing. Alternatively, (a) the baseline in patients whose pretreatment clotting activity is <1% of normal, who have no detectable clotting factor antigen, and have nonsense genotypes can be defined as 0%, (b) the baseline for patients with pretreatment clotting activity <1% of normal and who have detectable clotting factor antigen can be set at 0.5%, (c) the baseline for patients whose pretreatment clotting activity is between 1-2% is $C_{min}$ (the lowest activity throughout the PK study), and (d) the baseline for patients whose pretreatment clotting activity is ≥2% can be set at 2% of normal. Activity above the baseline pre-dosing can be considered residue drug from prior treatment, and can be decayed to baseline and subtracted from the PK data following clotting factor dosing.

"Trough," as used herein, is the lowest plasma clotting activity level reached after administering a dose of a clotting factor molecule (e.g., chimeric clotting factor) and before the next dose is administered, if any. Trough is used interchangeably herein with "threshold." Baseline clotting factor levels are subtracted from measured clotting factor levels to calculate the trough level.

"Subject," as used herein means a mammal. The subject can be a human, e.g., a human patient. Subject as used herein includes an individual who is known to have at least one incidence of uncontrolled bleeding episodes, who has been diagnosed with a disease or disorder associated with uncontrolled bleeding episodes, e.g., a bleeding disease or disorder, e.g., hemophilia A or hemophilia B, who are susceptible to uncontrolled bleeding episodes, e.g., hemophilia, or any combinations thereof. Subjects can also include an individual who is in danger of one or more uncontrollable bleeding episodes prior to a certain activity, e.g., a surgery, a sport activity, or any strenuous activities. The subject can have a baseline clotting activity less than 1%, less than 0.5%, less than 2%, less than 2.5%, less than 3%, or less than 4%.

"Variant," as used herein, refers to a polynucleotide or polypeptide differing from the original polynucleotide or polypeptide, but retaining essential properties thereof, e.g., clotting activity or Fc (FcRn binding) activity. Generally, variants are overall closely similar, and, in many regions, identical to the original polynucleotide or polypeptide. Variants include polypeptide and polynucleotide fragments, deletions, insertions, and modified versions of original polypeptides.

II. CLOTTING FACTORS

The present invention is directed to a clotting factor suitable for a fixed dosing regimen. A suitable dosing strategy can be identified for a particular drug based on its pharmacokinetic (PK) and/or pharmacodynamic (PD) properties. For example, a good drug candidate for a fixed dosing strategy provides more consistent exposure of the drug across subjects when administered by a fixed dosing regimen rather than by a body weight based dosing regimen. Advantages of the present invention include: improved regimen compliance; reduced break through bleeds; increased protection of joints from bleeds; prevention of joint damage; reduced morbidity; reduced mortality; prolonged protection from bleeding; decreased thrombotic events; and improved quality of life. In one embodiment, a clotting factor suitable for a fixed dosing regimen exhibits a wide therapeutic window. In another embodiment, a clotting factor suitable for a fixed dosing regimen has less inter-individual variability of pharmacokinetic parameters (e.g., AUC or $C_{max}$) when administered by a fixed dosing regimen compared to the inter-individual variability of pharmacokinetic parameters when administered by a body-weight based dosing regimen. In another embodiment, a clotting factor suitable for a fixed dosing regimen has inter-individual variability of pharmacokinetic parameters (e.g., AUC or $C_{max}$) that is similar when administered either by a fixed dosing regimen or by a body-weight based dosing regimen.

In one aspect, the pharmaceutical properties of a clotting factor suitable for a fixed dosing regimen can be represented by the following formulas:

$$\text{AUC} = \text{Dose}/CL, \tag{C}$$

$$CL = \text{Typical } CL \times (\text{BW}/\text{Typical BW})^{exponent} \tag{D}$$

$$C_{max} = \text{Dose}/V, \tag{E}$$

$$V = \text{Typical } V \times (\text{BW}/\text{TypicalBW})^{exponent} \tag{F}$$

The exponent for formula (D) indicates a body weight effect on clearance ($\theta_{BW\_CL}$). The exponent for formula (F) indicates a body weight effect on the central volume of distribution ($\theta_{BW\_V1}$). In another aspect of the invention, the body weight effect on clearance ($\theta_{BW\_CL}$) of the clotting factor is equal to or less than 0.75, 0.74, 0.73, 0.72, 0.71, 0.70, 0.69, 0.68, 0.67, 0.66, 0.65, 0.64, 0.63, 0.62, 0.61, 0.6, 0.59, 0.58, 0.57, 0.56, 0.55, 0.54, 0.53, 0.52, 0.51, 0.50, 0.49, 0.48, 0.47, 0.46, 0.45, 0.44, 0.43, 0.42, 0.41, 0.40, 0.39, 0.38, 0.37, 0.36, 0.35, 0.34, 0.32, 0.31, 0.3, 0.25, 0.2, 0.15, 0.1, 0.5, or 0. In other aspects, the body weight effect on the central volume of distribution ($\theta_{BW\_V1}$) of the clotting factor is equal to or less than 0.75, 0.74, 0.73, 0.72, 0.71, 0.70, 0.69, 0.68, 0.67, 0.66, 0.65, 0.64, 0.63, 0.62, 0.61, 0.6, 0.59, 0.58, 0.57, 0.56, 0.55, 0.54, 0.53, 0.52, 0.51, 0.50, 0.49, 0.48, 0.47, 0.46, 0.45, 0.44, 0.43, 0.42, 0.41, 0.40, 0.39, 0.38, 0.37, 0.36, 0.35, 0.34, 0.32, 0.31, 0.3, 0.25, 0.2, 0.15, 0.1, 0.5, or 0. In still other aspects, $\theta_{BW\_CL}$ is equal to or less than 0.75, 0.74, 0.73, 0.72, 0.71, 0.70, 0.69, 0.68, 0.67, 0.66, 0.65, 0.64, 0.63, 0.62, 0.61, 0.6, 0.59, 0.58, 0.57, 0.56, 0.55, 0.54, 0.53, 0.52, 0.51, 0.50, 0.49, 0.48, 0.47, 0.46, 0.45, 0.44, 0.43, 0.42, 0.41, 0.40, 0.39, 0.38, 0.37, 0.36, 0.35, 0.34, 0.32, 0.31, or 0.3, 0.25, 0.2, 0.15, 0.1, 0.5, or 0 and $\theta_{BW\_V1}$ is equal to or less than 0.75, 0.74, 0.73, 0.72, 0.71, 0.70, 0.69, 0.68, 0.67, 0.66, 0.65, 0.64, 0.63, 0.62, 0.61, 0.6, 0.59, 0.58, 0.57, 0.56, 0.55, 0.54, 0.53, 0.52, 0.51, 0.50, 0.49, 0.48, 0.47, 0.46, 0.45, 0.44, 0.43, 0.42, 0.41, 0.40, 0.39, 0.38, 0.37, 0.36, 0.35, 0.34, 0.32, 0.31, or 0.3, 0.25, 0.2, 0.15, 0.1, 0.5, or 0. In some aspects, the clotting factor has $\theta_{BW\_CL}$ equal to or less than about 0.500 and $\theta_{BW\_V1}$ equal to or less than 0.467. In other embodiments, the clotting factor has $\theta_{BW\_CL}$ equal to about 0 and $\theta_{BW\_V1}$ equal to or less than 0.492. In other embodiments, the clotting factor has $\theta_{BW\_CL}$ equal to or less than about 0.436 and $\theta_{BW\_V1}$ equal to or less than about 0.396.

In certain aspects, a clotting factor is administered to a population of two or more subjects. In some aspects, the area under curve (AUC) or $C_{max}$ between a high extreme body weight subject and a low extreme body weight subject after administration of the fixed dosing of the clotting factor is similar to or less variable than AUC or $C_{max}$ between a high body weight subject and a low body weight after administration of a body weight-based dosing amount of the clotting factor. In one embodiment, the variability in AUC is less than ±50%, less than ±45%, less than ±40%, less than ±35%, less than ±30%, or less than ±25%. In another embodiment, the variability in $C_{max}$ is less than ±50%, less than ±45%, less than ±40%, less than ±35%, less than ±30%, or less than ±25%.

In other aspects, the clotting factor has a wide therapeutic window. In one embodiment, the therapeutic window for the clotting factor comprises a maximum serum concentration ($C_{max}$) of about 150% of normal and a minimum serum concentration ($C_{min}$) of about 1% of normal. In still other aspects, the body weight of the subject does not drive pharmacodynamic variability when administered by a fixed dosing regimen compared to the pharmacodynamics variability when administered by a body weight based dosing regimen. In some aspects, a clotting factor of the invention has low or no off-target toxicity. In certain aspects, a clotting factor is cleared primarily through cellular uptake in liver.

In some aspects, a clotting factor has less pharmacokinetic inter-subject variability than a clotting factor suitable for a body-weight based dosing. In one embodiment, the inter-subject variability is about 20% to about 50%, about 21% to about 49%, about 22% to about 48%, about 23% to about 47%, about 24% to about 46%, about 25% to about 46%, about 26% to about 46% for total clearance (CL) and Volume of Distribution at Steady State (Vss).

A clotting factor suitable for a fixed dosing strategy can be a wild-type clotting factor, a commercially available clotting factor, or a modified clotting factor. Examples of the wild-type clotting factors include, but are not limited to, full-length recombinant FIX (e.g., BENEFIX®), plasma-derived FIX (e.g., ALPHANINE®, or MONONINE®), or full-length recombinant FVIII (e.g., RECOMBINATE®, ADVATE®, or HELIXATE®), or B-domain deleted recombinant FVIII (e.g., REFACTO® or XYNTHA®).

Clotting factors for the invention can be modified. Modified clotting factors includes any clotting factors that have improvements in one or more aspects, pharmacokinetics (PK), pharmacodynamics (PD), stability, expression, or any combinations thereof. In one embodiment, a modified clotting factor comprises a clotting factor and a heterologous moiety. In another embodiment, a clotting factor for the invention is a long-acting clotting factor. Long-acting clotting factors can comprise a heterologous moiety that increases in vivo half-life of the clotting factor. In other embodiments, the heterologous moiety for the modified clotting factor (e.g., long-acting clotting factor) is a polypeptide moiety or a non-polypeptide moiety. In yet other embodiments, a heterologous moiety comprises albumin, albumin binding polypeptide, an FcRn binding partner, PAS, the C-terminal peptide (CTP) of the β subunit of human chorionic gonadotropin, polyethylene glycol (PEG), hydroxyethyl starch (HES), albumin-binding small molecules, or combinations thereof. Examples of the heterologous moieties are described below. In some embodiments, a clotting factor of the invention is a chimeric clotting factor. In some embodiments, the heterologous moiety is linked to the N-terminus or the C-terminus of the FVIII polypeptide or inserted between two amino acids of the FVIII polypeptide.

A. Factor IX

In certain embodiments, a clotting factor of the invention is a modified FIX polypeptide. In one example, a modified clotting factor useful for the invention comprises a long-acting FIX polypeptide, which is a chimeric polypeptide comprising a FIX polypeptide and an FcRn binding partner. The FIX polypeptide of the invention comprises a functional Factor IX polypeptide in its normal role in coagulation, unless otherwise specified. Thus, the FIX polypeptide includes variant polypeptides that are functional and the polynucleotides that encode such functional variant polypeptides. In one embodiment, the FIX polypeptides are the human, bovine, porcine, canine, feline, and murine FIX polypeptides. The full-length polypeptide and polynucleotide sequences of FIX are known, as are many functional variants, e.g., fragments, mutants and modified versions. FIX polypeptides include full-length FIX, full-length FIX minus Met at the N-terminus, full-length FIX minus the signal sequence, mature FIX (minus the signal sequence and propeptide), and mature FIX with an additional Met at the N-terminus. FIX can be made by recombinant means ("recombinant Factor IX" or "rFIX"), i.e., it is not naturally occurring or derived from plasma.

A great many functional FIX variants are known. International publication number WO 02/040544 A3, which is herein incorporated by reference in its entirety, discloses mutants that exhibit increased resistance to inhibition by heparin at page 4, lines 9-30 and page 15, lines 6-31. International publication number WO 03/020764 A2, which is herein incorporated by reference in its entirety, discloses FIX mutants with reduced T cell immunogenicity in Tables 2 and 3 (on pages 14-24), and at page 12, lines 1-27. International publication number WO 2007/149406 A2, which is herein incorporated by reference in its entirety, discloses functional mutant FIX molecules that exhibit increased protein stability, increased in vivo and in vitro half-life, and increased resistance to proteases at page 4, line 1 to page 19, line 11. WO 2007/149406 A2 also discloses chimeric and other variant FIX molecules at page 19, line 12 to page 20, line 9. International publication number WO 08/118507 A2, which is herein incorporated by reference in its entirety, discloses FIX mutants that exhibit increased clotting activity at page 5, line 14 to page 6, line 5. International publication number WO 09/051717 A2, which is herein incorporated by reference in its entirety, discloses FIX mutants having an increased number of N-linked and/or O-linked glycosylation sites, which results in an increased half-life and/or recovery at page 9, line 11 to page 20, line 2. International publication number WO 09/137254 A2, which is herein incorporated by reference in its entirety, also discloses Factor IX mutants with increased numbers of glycosylation sites at page 2, paragraph [006] to page 5, paragraph [011] and page 16, paragraph [044] to page 24, paragraph [057]. International publication number WO 09/130198 A2, which is herein incorporated by reference in its entirety, discloses functional mutant FIX molecules that have an increased number of glycosylation sites, which result in an increased half-life, at page 4, line 26 to page 12, line 6. International publication number WO 09/140015 A2, which is herein incorporated by reference in its entirety, discloses functional FIX mutants that an increased number of Cys residues, which may be used for polymer (e.g., PEG) conjugation, at page 11, paragraph [0043] to page 13, paragraph [0053]. The FIX polypeptides described in International Application No. PCT/US2011/043569 filed Jul. 11, 2011 and published as WO 2012/006624 on Jan. 12, 2012 are also incorporated herein by reference in its entirety.

In addition, hundreds of non-functional mutations in FIX have been identified in hemophilia patients, many of which are disclosed in Table 1, at pages 11-14 of International publication number WO 09/137254 A2, which is herein incorporated by reference in its entirety. Such non-functional mutations are not included in the invention, but provide additional guidance for which mutations are more or less likely to result in a functional FIX polypeptide.

In one embodiment, the Factor IX (or Factor IX portion of a chimeric polypeptide) may be at least 70%, at least 80%, at least 85%, at least 90%, at least 95%, at least 96%, at least 97%, at least 98%, at least 99%, or 100% identical to a FIX amino acid sequence shown in Table 5A without a signal sequence and propeptide sequence (amino acids 1 to 415 of SEQ ID NO:2), or alternatively, with a propeptide sequence, or with a propeptide and signal sequence (full-length FIX).

Factor IX coagulant activity is expressed as International Unit(s) (IU). One IU of FIX activity corresponds approximately to the quantity of FIX in one milliliter of normal human plasma. Several assays are available for measuring Factor IX activity, including the one stage clotting assay (activated partial thromboplastin time; aPTT), thrombin generation time (TGA) and rotational thromboelastometry (ROTEM®).

A chimeric polypeptide comprising a FIX polypeptide and an FcRn binding partner can comprise an amino acid sequence at least 60%, at least 70%, at least 80%, at least 85%, at least 90%, at least 95%, at least 96%, at least 97%, at least 98%, at least 99%, or 100% identical to the Factor IX and FcRn BP, e.g., the Fc amino acid sequence shown in Table 5A without a signal sequence and propeptide sequence (amino acids 1 to 642 of SEQ ID NO:2), or alternatively, with a propeptide sequence, or alternatively with a signal sequence and a propeptide sequence.

A long-acting or long-lasting FIX polypeptide can be a hybrid FIX polypeptide. Hybrid FIX polypeptide means a combination of a FIX chimeric polypeptide with a second polypeptide. The chimeric polypeptide and the second polypeptide in a hybrid may be associated with each other via non-covalent protein-protein interactions, such as charge-charge or hydrophobic interactions. The chimeric polypeptide and the second polypeptide in a hybrid may be associated with each other via covalent bond(s) such as disulfide bonds. The chimeric peptide and the second peptide may be associated with each other via more than one type of bond, such as non-covalent and disulfide bonds. Hybrids are described in WO 2004/101740, WO2005/001025, U.S. Pat. No. 7,404,956, U.S. Pat. No. 7,348,004, and WO 2006/074199, each of which is incorporated herein by reference in its entirety. The second polypeptide may be a second copy of the same chimeric polypeptide or it may be a non-identical chimeric polypeptide. In other embodiments, the second polypeptide is a polypeptide comprising an FcRn BP, e.g., Fc. In some embodiments, the chimeric polypeptide is a Factor IX-FcRn BP, e.g., Factor IX-Fc chimeric polypeptide, and the second polypeptide consists essentially of Fc. See, e.g., Table 5A and B (SEQ ID NOs:2 and 4). See, e.g., U.S. Pat. No. 7,404,956, which is incorporated herein by reference in its entirety.

The second polypeptide in a hybrid may comprise or consist essentially of a sequence at least 70%, at least 80%, at least 85%, at least 90%, at least 95%, at least 96%, at least 97%, at least 98%, at least 99%, or 100% identical to the amino acid sequence shown in Table 5B without a signal sequence (SEQ ID NO:4), or alternatively, with a signal sequence.

In some embodiments, a long-acting FIX polypeptide is a FIX monomer dimer hybrid. Monomer-dimer hybrid can comprise two polypeptide chains, one chain comprising a FIX polypeptide and a first Fc region, and another chain comprising, consisting essentially of, or consisting of a second Fc region. In certain aspects, a FIX monomer dimer hybrid consists essentially of or consists of two polypeptide chains, a first chain consisting essentially of or consisting of a FIX polypeptide and a second chain consisting essentially of or consisting of a second Fc region.

A long-acting FIX polypeptide can be encoded by a nucleotide sequence which is at least 85%, 90%, 95%, 96%, 97%, 98% or 99% identical to, for example, the nucleotide coding sequence in SEQ ID NO:1 or 3 (the Factor IX portion, the Fc portion, individually or together) or the complementary strand thereto, the nucleotide coding sequence of known mutant and recombinant Factor IX or Fc such as those disclosed in the publications and patents cited herein or the complementary strand thereto, a nucleotide sequence encoding the polypeptide of SEQ ID NO:2 or 4 (the Factor IX portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

B. Factor VIII

In some embodiments, a clotting factor for the invention is a modified FVIII polypeptide. In one aspect, a modified FVIII polypeptide is a long-acting FVIII polypeptide. In another aspect, a long-acting FVIII polypeptide comprises a FVIII polypeptide and an FcRn binding partner. The FVIII polypeptide means functional factor VIII polypeptide in its normal role in coagulation, unless otherwise specified. Thus, the term Factor VIII includes variant polypeptides that are functional. Factor VIII proteins can be the human, porcine, canine, and murine factor VIII proteins, in addition, the full-length polypeptide and polynucleotide sequences are known, as are many functional fragments, mutants and modified versions. Examples of human factor VIII sequences are shown as subsequences in SEQ ID NO: 6 or 8 (Table 7A and 7B). Factor VIII polypeptides include, e.g., full-length factor VIII, fall-length factor VIII minus Met at the N-terminus, mature factor VIII (minus the signal sequence), mature factor VIII with an additional Met at the N-terminus, and/or factor VIII with a full or partial deletion of the B domain. Factor VIII variants include B domain deletions, whether partial or full deletions.

A great many functional factor VIII variants are known, as is discussed above and below. In addition, hundreds of nonfunctional mutations in factor VIII have been identified in hemophilia patients, and it has been determined that the effect of these mutations on factor VIII function is due more to where they lie within the 3-dimensional structure of factor VIII than on the nature of the substitution (Cutler et al., Hum. Mutat. 19:274-8 (2002)), incorporated herein by reference in its entirety. In addition, comparisons between factor VIII from humans and other species have identified conserved residues that are likely to be required for function (Cameron et al., Thromb. Haemost. 79:317-22 (1998); U.S. Pat. No. 6,251,632), incorporated herein by reference in its entirety.

The human factor VIII gene was isolated and expressed in mammalian cells (Toole, J. J., et al., Nature 312:342-347 (1984); Gitschier, J., et al., Nature 312:326-330 (1984); Wood, W. I., et al., Nature 312:330-337 (1984); Vehar, G. A., et al., Nature 312:337-342 (1984); WO 87/04187; WO 88/08035; WO 88/03558; U.S. Pat. No. 4,757,006), each of which is incorporated herein by reference in its entirety, and the amino acid sequence was deduced from cDNA. Capon et al., U.S. Pat. No. 4,965,199, incorporated herein by reference in its entirety, discloses a recombinant DNA method for producing factor VIII in mammalian host cells and purification of human factor VIII. Human factor VIII expression in CHO (Chinese hamster ovary) cells and BHKC (baby hamster kidney cells) has been reported. Human factor VIII has been modified to delete part or all of the B domain (U.S. Pat. Nos. 4,994,371 and 4,868,112, each of which is incorporated herein by reference in its entirety), and replacement of the human factor VIII B domain with the human factor V B domain has been performed (U.S. Pat. No. 5,004,803, incorporated herein by reference in its entirety). The cDNA sequence encoding human factor VIII and predicted amino acid sequence are shown in SEQ ID NO: 3B and 4B, respectively, of US Application Publ. No. 2005/0100990, incorporated herein by reference in its entirety.

U.S. Pat. No. 5,859,204, Lollar, J. S., incorporated herein by reference in its entirety, reports functional mutants of factor VIII having reduced antigenicity and reduced immunoreactivity. U.S. Pat. No. 6,376,463, Lollar, J. S., incorporated herein by reference in its entirety, also reports mutants of factor VIII having reduced immunoreactivity. US Application Publ. No. 2005/0100990, Saenko et al., incorporated herein by reference in its entirety, reports functional mutations in the A2 domain of factor VIII.

A number of functional factor VIII molecules, including B-domain deletions, are disclosed in the following U.S. Pat. No. 6,316,226 and U.S. Pat. No. 6,346,513, both assigned to Baxter; U.S. Pat. No. 7,041,635 assigned to In2Gen; U.S. Pat. No. 5,789,203, U.S. Pat. No. 6,060,447, U.S. Pat. No. 5,595,886, and U.S. Pat. No. 6,228,620 assigned to Chiron; U.S. Pat. No. 5,972,885 and U.S. Pat. No. 6,048,720 assigned to Biovitrum, U.S. Pat. No. 5,543,502 and U.S. Pat. No. 5,610,278 assigned to Novo Nordisk; U.S. Pat. No. 5,171,844 assigned to Immuno Ag; U.S. Pat. No. 5,112,950 assigned to Transgene S. A.; U.S. Pat. No. 4,868,112 assigned to Genetics Institute, each of which is incorporated herein by reference in its entirety.

The porcine factor VIII sequence is published, (Toole, J. J., et al., Proc. Natl. Acad. Sci. USA 83:5939-5942 (1986)), incorporated herein by reference in its entirety, and the complete porcine cDNA sequence obtained from PCR amplification of factor VIII sequences from a pig spleen cDNA library has been reported (Healey, J. F. et al., Blood 88:4209-4214 (1996), incorporated herein by reference in its entirety). Hybrid human/porcine factor VIII having substitutions of all domains, all subunits, and specific amino acid sequences were disclosed in U.S. Pat. No. 5,364,771 by Lollar and Runge, and in WO 93/20093, incorporated herein by reference in its entirety. More recently, the nucleotide and corresponding amino acid sequences of the A1 and A2 domains of porcine factor VIII and a chimeric factor VIII with porcine A1 and/or A2 domains substituted for the corresponding human domains were reported in WO 94/11503, incorporated herein by reference in its entirety. U.S. Pat. No. 5,859,204, Lollar, J. S., also discloses the porcine cDNA and deduced amino acid sequences. U.S. Pat. No. 6,458,563, incorporated herein by reference in its entirety assigned to Emory discloses a B-domain deleted porcine Factor VIII.

The factor VIII (or Factor VIII portion of a chimeric polypeptide) may be at least 60%, at least 70%, at least 80%, at least 90%, at least 95%, at least 96%, at least 97%, at least 98%, at least 99%, or at least 100% identical to a Factor VIII amino acid sequence shown in Tables 7A and 7B without a signal sequence (amino acids 20 to 1457 of SEQ ID NO: 6; and amino acids 20 to 2351 of SEQ ID NO: 8), wherein said Factor VIII portion has Factor VIII activity. The Factor VIII (or Factor VII portion of a chimeric polypeptide) may be identical to a Factor VIII amino acid sequence shown in Tables 7A and 7B without a signal sequence (amino acids 20 to 1457 of SEQ ID NO: 6; and amino acids 20 to 2351 of SEQ ID NO: 8).

The Factor VIII (or Factor VIII portion of a chimeric polypeptide) may be at least 60%, at least 70%, at least 80%, at least 90%, at least 95%, at least 96%, at least 97%, at least 98%, at least 99%, or at least 100% identical to a Factor VIII amino acid sequence shown in Tables 7A and 7B with a signal sequence (amino acids 1 to 1457 of SEQ ID NO: 6 and amino acids 1 to 2351 of SEQ ID NO: 8), wherein the Factor VIII portion has Factor VIII activity. The Factor VIII (or Factor VIII portion of a chimeric polypeptide) may be identical to a Factor VIII amino acid sequence shown in Tables 7A and 7B with a signal sequence (amino acids 1 to 1457 of SEQ ID NO: 6 and amino acids 1 to 2351 of SEQ ID NO: 8).

A "B domain" of Factor VIII, as used herein, is the same as the B domain known in the art that is defined by internal amino acid sequence identity and sites of proteolytic cleavage by thrombin, e.g., residues Ser741-Arg1648 of full-length human factor VIII. The other human factor VIII domains are defined by the following amino acid residues: A1, residues Ala1-Arg372; A2, residues Ser373-Arg740; A3, residues Ser1690-Ile2032; C1, residues Arg2033-Asn2172; C2, residues Ser2173-Tyr2332. The A3-C1-C2 sequence includes residues Ser1690-Tyr2332. The remaining sequence, residues Glu1649-Arg1689, is usually referred to as the factor VIII light chain activation peptide. The locations of the boundaries for all of the domains, including the B domains, for porcine, mouse and canine factor VIII are also known in the art. In one embodiment, the B domain of Factor VIII is deleted ("B domain deleted factor VIII" or "BDD FVIII"). An example of a BDD FVIII is REFACTO® (recombinant SQ BDD FVIII), which has the same sequence as the Factor VIII portion of the sequence in Table 7A (amino acids 1 to 1457 or 20 to 1457 of SEQ ID NO:6). In another embodiment, the B domain deleted Factor VIII contains an intact intracellular processing site, which corresponds to Arginine at residue 754 of B domain deleted Factor VIII, which corresponds to Arginine residue 773 of SEQ ID NO: 6, or residue 1648 of full-length Factor VIII, which corresponds to Arginine residue 1667 of SEQ ID NO: 8. The sequence residue numbers used herein without referring to any SEQ ID Numbers correspond to the Factor VIII sequence without the signal peptide sequence (19 amino acids) unless otherwise indicated. For example, S743/Q1638 of full-length Factor VIII corresponds to S762/Q1657 of SEQ ID NO: 8 due to the 19 amino acid signal peptide sequence. In other embodiments, the B domain deleted FVIII comprises a substitution or mutation at an amino acid position corresponding to Arginine 1645, a substitution or mutation at an amino acid position corresponding to Arginine 1648, or a substitution or mutation at amino acid positions corresponding to Arginine 1645 and Arginine 1648 in full-length Factor VIII. In some embodiments, the amino acid substituted at the amino acid position corresponding to Arginine 1645 is a different amino acid from the amino acid substituted at the amino acid position corresponding to Arginine 1648. In certain embodiments, the substitution or mutation is an amino acid other than arginine, e.g., alanine.

A "B domain deleted factor VIII" may have the full or partial deletions disclosed in U.S. Pat. Nos. 6,316,226, 6,346,513, 7,041,635, 5,789,203, 6,060,447, 5,595,886, 6,228,620, 5,972,885, 6,048,720, 5,543,502, 5,610,278, 5,171,844, 5,112,950, 4,868,112, and 6,458,563, each of which is incorporated herein by reference in its entirety. In some embodiments, a B domain deleted factor VIII sequence of the present invention comprises any one of the deletions disclosed at col. 4, line 4 to col. 5, line 28 and examples 1-5 of U.S. Pat. No. 6,316,226 (also in U.S. Pat. No. 6,346,513). In some embodiments, a B domain deleted factor VIII of the present invention has a deletion disclosed at col. 2, lines 26-51 and examples 5-8 of U.S. Pat. No. 5,789,203 (also U.S. Pat. No. 6,060,447, U.S. Pat. No. 5,595,886, and U.S. Pat. No. 6,228,620). In some embodiments, a B domain deleted factor VIII has a deletion described in col. 1, lines 25 to col. 2, line 40 of U.S. Pat. No. 5,972,885; col. 6, lines 1-22 and example 1 of U.S. Pat. No. 6,048,720; col. 2, lines 17-46 of U.S. Pat. No. 5,543,502; col. 4, line 22 to col. 5, line 36 of U.S. Pat. No. 5,171,844; col. 2, lines 55-68, FIG. 2, and example 1 of U.S. Pat. No. 5,112,950; col. 2, line 2 to col. 19, line 21 and table 2 of U.S. Pat. No. 4,868,112; col. 2, line 1 to col. 3, line 19, col. 3, line 40 to col. 4, line 67, col. 7, line 43 to col. 8, line 26, and col. 11, line 5 to col. 13, line 39 of U.S. Pat. No. 7,041,635; or col. 4, lines 25-53, of U.S. Pat. No. 6,458,563. In some embodiments, a B domain deleted factor VIII has a deletion of most of the B domain, but still contains amino-terminal sequences of the B domain that are essential for in vivo proteolytic processing of the primary translation product into two polypeptide chain (i.e., intracellular processing site), as disclosed in WO 91/09122, which is incorporated herein by reference in its entirety. In some embodiments, a B domain deleted factor VIII is constructed with a deletion of amino acids 747-1638, i.e., virtually a complete deletion of the B domain. Hoeben R. C., et al. *J, Biol. Chem.* 265 (13): 7318-7323 (1990), incorporated herein by reference in its entirety. A B domain deleted factor VIII may also contain a deletion of amino acids 771-1666 or amino acids 868-1562 of factor VIII. Meulien P., et al. *Protein Eng.* 2(4): 301-6 (1988), incorporated herein by reference in its entirety. Additional B domain deletions that are part of the invention include, e.g.: deletion of amino acids 982 through 1562 or 760 through 1639 (Toole et al., Proc. Natl. Acad. Sci. U.S.A. 83:5939-5942 (1986)), 797 through 1562 (Eaton et al., Biochemistry 25:8343-8347 (1986)), 741 through 1646 (Kaufman (PCT published application No. WO 87/04187)), 747-1560 (Sarver et al., DNA 6:553-564 (1987)), 741 through 1648 (Pasek (PCT application No. 88/00831)), 816 through 1598 or 741 through 1689 (Lagner (Behring Inst. Mitt. (1988) No 82:16-25, EP 295597)), each of which is incorporated herein by reference in its entirety. Each of the foregoing deletions may be made in any Factor VIII sequence.

In one embodiment, the B domain deleted Factor VIII portion in the chimeric polypeptide is processed into two chains connected (or associated) by a metal bond, the first chain comprising a heavy chain (A1-A2-partial B) and a second chain comprising a light chain (A3-C1-C2). In another embodiment, the B domain deleted Factor VIII portion is a single chain Factor VIII or unprocessed FVIII. The single chain Factor VIII can comprise an intracellular processing site, which corresponds to Arginine at residue 754 of B domain deleted Factor VIII (i.e., residue 773 of SEQ ID NO: 6) or at residue 1648 of full-length Factor VIII (i.e., residue 1657 of SEQ ID NO: 8).

The metal bond between the heavy chain and the light chain can be any metal known in the art. For example, the metals useful for the invention can be a divalent metal ion. The metals that can be used to associate the heavy chain and light chain include, but not limited to, Ca2+, Mn2+, or Cu2+. Fatouros et al., Intern. *J Pharm.* 155(1): 121-131 (1997); Wakabayashi et al., JBC. 279(13): 12677-12684 (2004).

In other embodiments, a FVIII polypeptide of the invention is processed FVIII comprising a light chain and a heavy chain of FVIII. In yet other embodiments, a FVIII polypeptide is single chain FVIII. In other embodiments, the single chain FVIII comprises a substitution or mutation at an amino acid position corresponding to Arginine 1645, a substitution or mutation at an amino acid position corresponding to Arginine 1648, or a substitution or mutation at amino acid positions corresponding to Arginine 1645 and Arginine 1648 in full-length Factor VIII. In some embodiments, the amino acid substituted at the amino acid position corresponding to Arginine 1645 is a different amino acid from the amino acid substituted at the amino acid position corresponding to Arginine 1648. In certain embodiments, the substitution or mutation is an amino acid other than arginine, e.g., alanine.

In one embodiment, a chimeric polypeptide comprising a FVIII polypeptide and an FcRn binding partner can comprise an amino acid sequence at least 70%, at least 80%, at least 85%, at least 90%, at least 95%, at least 96%, at least 97%, at least 98%, at least 99%, or 100% identical to the Factor VIII and FcRn BP, e.g., the Fc amino acid sequence shown in Table 5B without a signal sequence (SEQ ID NO:4).

In another embodiment, a chimeric polypeptide comprising a FVIII polypeptide and an FcRn binding partner can comprise an amino acid sequence at least 70%, at least 80%, at least 85%, at least 90%, at least 95%, at least 96%, at least 97%, at least 98%, at least 99%, or 100% identical to the Factor VIII and FcRn BP, e.g., the Fc amino acid sequence shown in Table 5B without a signal sequence (SEQ ID NO:4).

A long-acting or long-lasting FVIII polypeptide can be a hybrid FVIII polypeptide. Hybrid FVIII polypeptide means a combination of a FVIII chimeric polypeptide with a second polypeptide. The chimeric polypeptide and the second polypeptide in a hybrid may be associated with each other via non-covalent protein-protein interactions, such as charge-charge or hydrophobic interactions. The chimeric polypeptide and the second polypeptide in a hybrid may be associated with each other via covalent bond(s) such as disulfide bonds. The chimeric peptide and the second peptide may be associated with each other via more than one type of bond, such as non-covalent and disulfide bonds. The second polypeptide may be a second copy of the same chimeric polypeptide or it may be a non-identical chimeric polypeptide. In other embodiments, the second polypeptide is a polypeptide comprising an FcRn BP, e.g., Fc. In some embodiments, the chimeric polypeptide is a Factor VIII-FcRn BP, e.g., Factor VIII-Fc chimeric polypeptide, and the second polypeptide consists essentially of Fc.

The second polypeptide in a hybrid may comprise or consist essentially of a sequence at least 70%, at least 80%, at least 85%, at least 90%, at least 95%, at least 96%, at least 97%, at least 98%, at least 99%, or 100% identical to the amino acid sequence shown in Table 5B without a signal sequence (SEQ ID NO:4), or alternatively, with a signal sequence.

In some embodiments, a long-acting FVIII polypeptide is a FVIII monomer dimer hybrid. Monomer-dimer hybrids can comprise two polypeptide chains, one chain comprising a FVIII polypeptide and a first Fc region, and another chain comprising, consisting essentially of, or consisting of a second Fc region. In certain aspects, a FVIII monomer dimer hybrid consists essentially of or consists of two polypeptide chains, a first chain consisting essentially of or consisting of a FVIII polypeptide and a second chain consisting essentially of or consisting of a second Fc region.

In some embodiments, a long-acting FVIII polypeptide comprises a FVIII polypeptide and at least one heterologous moiety, which increases in vivo half-life of the FVIII polypeptide, wherein the at least one heterologous moiety is linked to the C-terminus or N-terminus of the FVIII polypeptide or inserted between two amino acids of the FVIII polypeptide.

A long-acting FVIII polypeptide can be encoded by a nucleotide sequence which is at least 85%, 90%, 95%, 96%, 97%, 98% or 99% identical to, for example, the nucleotide coding sequence in SEQ ID NO:5 or 7 (the Factor VIII portion, the Fc portion, individually or together) or the complementary strand thereto, the nucleotide coding sequence of known mutant and recombinant Factor VIII or Fc such as those disclosed in the publications and patents cited herein or the complementary strand thereto, a nucleotide sequence encoding the polypeptide of SEQ ID NO:6 or 8 (the Factor VIII portion, the Fc portion, individually or together), and/or polynucleotide fragments of any of these nucleic acid molecules (e.g., those fragments described herein). Polynucleotides which hybridize to these nucleic acid molecules under stringent hybridization conditions or lower stringency conditions are also included as variants, as are polypeptides encoded by these polynucleotides as long as they are functional.

By a nucleic acid having a nucleotide sequence at least, for example, 95% "identical" to a reference nucleotide sequence, it is intended that the nucleotide sequence of the nucleic acid is identical to the reference sequence except that the nucleotide sequence may include up to five point mutations per each 100 nucleotides of the reference nucleotide sequence. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be, for example, the entire sequence shown in SEQ ID NO:1 or 3, the ORF (open reading frame), or any fragment specified as described herein.

As a practical matter, whether any particular nucleic acid molecule or polypeptide is at least 85%, 90%, 95%, 96%, 97%, 98% or 99% identical to a nucleotide sequence or polypeptide of the present invention can be determined conventionally using known computer programs. In one embodiment, the best overall match between a query sequence (reference or original sequence) and a subject sequence, also referred to as a global sequence alignment, can be determined using the FASTDB computer program based on the algorithm of Brutlag et al. (Comp. App. Biosci. (1990) 6:237-245), which is herein incorporated by reference in its entirety. In a sequence alignment the query and subject sequences are both DNA sequences. An RNA sequence can be compared by converting U's to T's. The result of said global sequence alignment is in percent identity. In certain embodiments, the parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to made for the purposes of the present invention.

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 85%, 90%, 95%, 96%, 97%, 98% or 99% identical to, for instance, the amino acid sequences of SEQ ID NOs:2, 4, 6, or 8 (the FIX portion, the FVIII portion, the Fc portion, individually or together), or a known FIX, FVIII, or Fc polypeptide sequence, can be determined conventionally using known computer programs. In one embodiment, the best overall match between a query sequence (reference or original sequence) and a subject sequence, also referred to as a global sequence alignment, can be determined using the FASTDB computer program based on the algorithm of Brutlag et al., Comp. App. Biosci. 6:237-245(1990), incorporated herein by reference in its entirety. In a sequence alignment the query and subject sequences are either both nucleotide sequences or both amino acid sequences. The result of said global sequence alignment is in percent identity. In certain embodiments, the parameters used in a FASTDB amino acid alignment are: Matrix=PAM 0, k-tuple=2, Mismatch Penalty=1, Joining Penalty=20, Randomization Group Length=0, Cutoff Score=1, Window Size-sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention, Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are to made for the purposes of the present invention.

The polynucleotide variants may contain alterations in the coding regions, non-coding regions, or both. Certain embodiments include polynucleotide variants containing alterations which produce silent substitutions, additions, or deletions, but do not alter the properties or activities of the encoded polypeptide. Nucleotide variants can be produced by silent substitutions due to the degeneracy of the genetic code. Moreover, variants in which 5-10, 1-5, or 1-2 amino acids are substituted, deleted, or added in any combination are included. Polynucleotide variants can be produced for a variety of reasons, e.g., to optimize codon expression for a particular host (change codons in the human mRNA to those preferred by a bacterial host such as *E. coli*).

Naturally occurring variants are called "allelic variants," and refer to one of several alternate forms of a gene occupying a given locus on a chromosome of an organism (Genes II, Lewin, B., ed., John Wiley & Sons, New York (1985)). These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides. For instance, one or more amino acids can be deleted from the N-terminus or C-terminus of the secreted protein without substantial loss of biological function. The authors of Ron et al., *J Biol. Chem.* 268: 2984-2988 (1993), incorporated herein by reference in its entirety, reported variant KGF proteins having heparin binding activity even after deleting 3, 8, or 27 amino-terminal amino acid residues. Similarly, Interferon gamma exhibited up to ten times higher activity after deleting 8-10 amino acid residues from the carboxy terminus of this protein. (Dobeli et al., *J. Biotechnology* 7:199-216 (1988), incorporated herein by reference in its entirety.)

Moreover, ample evidence demonstrates that variants often retain a biological activity similar to that of the naturally occurring protein. For example, Gayle and coworkers (*J Biol. Chem.* 268:22105-22111 (1993), incorporated herein by reference in its entirety) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." (See Abstract.) In fact, only 23 unique amino acid sequences, out of more than 3,500 nucleotide sequences examined, produced a protein that significantly differed in activity from wild type.

As stated above, polypeptide variants include modified polypeptides. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

C. Half-Life Extension

In certain aspects, a modified clotting factor of the invention comprises at least one heterologous moiety which increases the in vivo half-life of the protein. In vivo half-life of a modified clotting factor can be determined by any method known to those of skill in the art, e.g., clotting activity assays (chromogenic assay or one stage clotting aPTT assay) to detect plasma clotting activity levels or ELISA to detect plasma clotting factor antigen level.

In certain aspects, a heterologous moiety which increases in vivo half-life of the modified clotting factor of the invention can comprise, without limitation, a heterologous polypeptide such as albumin, an immunoglobulin Fc region, the β subunit of the C-terminal peptide (CTP) of human chorionic gonadotropin, a PAS sequence, a HAP sequence, a transferrin, albumin-binding moieties, or any fragments, derivatives, variants, or combinations of these polypeptides. In certain aspects the modified clotting factor of the invention comprises a heterologous polypeptide which increases in vivo half-life. In other related aspects a heterologous moiety can include an attachment site for a non-polypeptide moiety such as polyethylene glycol (PEG), hydroxyethyl starch (HES), polysialic acid, or any derivatives, variants, or combinations of these elements.

In other embodiments, a modified clotting factor of the invention is conjugated to one or more polymers. The polymer can be water-soluble or non-water-soluble. The polymer can be covalently or non-covalently attached to a clotting factor or to other moieties conjugated to a clotting factor. Non-limiting examples of the polymer can be poly (alkylene oxide), poly(vinyl pyrrolidone), poly(vinyl alcohol), polyoxazoline, or poly(acryloylmorpholine). Additional types of polymer-conjugated clotting factor are disclosed in U.S. Pat. No. 7,199,223, which is disclosed by reference in its entirety.

In certain aspects, a modified clotting factor of the invention can comprise one, two, three or more heterologous moieties, which can each be the same or different molecules.

D. FcRn Binding Partner

FcRn binding partner ("FcRn BP") comprises functional neonatal Fc receptor (FcRn) binding partners, unless otherwise specified. An FcRn binding partner is any molecule that can be specifically bound by the FcRn receptor with consequent active transport by the FcRn receptor of the FcRn binding partner. Thus, the term FcRn BP includes any variants of IgG Fc that are functional. For example, the region of the Fc portion of IgG that binds to the FcRn receptor has been described based on X-ray crystallography (Burmeister et al. 1994, Nature 372:379, incorporated herein by reference in its entirety). The major contact area of the Fc with the FcRn is near the junction of the CH2 and CH3 domains. Fc-FcRn contacts are all within a single Ig heavy chain. FcRn BPs include whole IgG, the Fc fragment of IgG, and other fragments of IgG that include the complete binding region of FcRn. The major contact sites include amino acid residues 248, 250-257, 272, 285, 288, 290-291, 308-311, and 314 of the CH2 domain and amino acid residues 385-387, 428, and 433-436 of the CH3 domain. References made to amino acid numbering of immunoglobulins or immunoglobulin fragments, or regions, are all based on Kabat et al. 1991, Sequences of Proteins of Immunological interest, U. S. Department of Public Health, Bethesda; MD, incorporated herein by reference in its entirety. (The FcRn receptor has been isolated from several mammalian species including humans. The sequences of the human FcRn, rat FcRn, and mouse FcRn are known (Story et al. 1994, J. Exp. Med. 180: 2377), incorporated herein by reference in its entirety.) An FcRn BP may comprise the CH2 and CH3 domains of an immunoglobulin with or without the hinge region of the immunoglobulin. In a particular embodiment, an FcRn BP is an Fc region. Exemplary FcRn BP variants are provided in WO 2004/101740 and WO 2006/074199, incorporated herein by reference in its entirety.

FcRn BP (or FcRn BP portion of a chimeric polypeptide) may contain one or more mutations, and combinations of mutations.

FcRn BP (or FcRn BP portion of a chimeric polypeptide) may contain mutations conferring increased half-life such as M252Y, S254T, T256E, and combinations thereof, as disclosed in Oganesyan et al., Mol. Immunol. 46:1750 (2009), which is incorporated herein by reference in its entirety; H433K, N434F, and combinations thereof, as disclosed in Vaccaro et al., Nat. Biotechnol. 23:1283 (2005), which is incorporated herein by reference in its entirety; the mutants disclosed at pages 1-2, paragraph [0012], and Examples 9 and 10 of U.S. 2009/0264627 A1, which is incorporated herein by reference in its entirety; and the mutants disclosed at page 2, paragraphs [0014] to [0021] of U.S. 20090163699 A1, which is incorporated herein by reference in its entirety.

FcRn BP (or FcRn BP portion of a chimeric polypeptide) may also include the following mutations: The Fc region of IgG can be modified according to well recognized procedures such as site directed mutagenesis and the like to yield modified IgG or Fc fragments or portions thereof that will be bound by FcRn. Such modifications include modifications remote from the FcRn contact sites as well as modifications within the contact sites that preserve or even enhance binding to the FcRn. For example the following single amino acid residues in human IgG1 Fc (Fcγ1) can be substituted without significant loss of Fc binding affinity for FcRn: P238A, S239A, K246A, K248A, D249A, M252A, T256A, E258A, T260A, D265A, S267A, H268A, E269A, D270A, E272A, L274A, N276A, Y278A, D280A, V282A, E283A, H285A, N286A, T289A, K290A, R292A, E293A, E294A, Q295A, Y296F, N297A, S298A, Y300F, R301A, V303A, V305A, T307A, L309A, Q311A, D312A, N315A, K317A, E318A, K320A, K322A, S324A, K326A, A327Q, P329A, A330Q, A330S, P331A, P331S, E333A, K334A, T335A, S337A, K338A, K340A, Q342A, R344A, E345A, Q347A, R355A, E356A, M358A, T359A, K360A, N361A, Q362A, Y373A, S375A D376A, A378Q, E380A, E382A, S383A, N384A, Q386A, E388A, N389A, N390A, Y391F, K392A, L398A, S400A, D401A, D413A, K414A, R416A, Q418A, Q419A, N421A, V422A, S424A, E430A, N434A, T437A, Q438A, K439A, S440A, S444A, and K447A, where for example P238A represents wild type proline substituted by alanine at position number 238. In addition to alanine other amino acids may be substituted for the wild type amino acids at the positions specified above. Mutations may be introduced singly into Fc giving rise to more than one hundred FcRn binding partners distinct from native Fc. Additionally, combinations of two, three, or more of these individual mutations may be introduced together, giving rise to hundreds more FcRn binding partners. Certain of these mutations may confer new functionality upon the FcRn binding partner. For example, one embodiment incorporates N297A, removing a highly conserved N-glycosylation site. The effect of this mutation is to reduce immunogenicity, thereby enhancing circulating half-life of the FcRn binding partner, and to render the FcRn binding partner incapable of binding to FcγRI, FcγRIIA, FcγRIIB, and FcγRIIIA, without compromising affinity for FcRn (Routledge et al. 1995, Transplantation 60:847, which is incorporated herein by reference in its entirety; Friend et al. 1999, Transplantation 68:1632, which is incorporated herein by reference in its entirety; Shields et al. 1995, J. Biol. Chem. 276:6591, which is incorporated herein by reference in its entirety). Additionally, at least three human Fc gamma receptors appear to recognize a binding site on IgG within the lower hinge region, generally amino acids 234-237. Therefore, another example of new functionality and potential decreased immunogenicity may arise from mutations of this region, as for example by replacing amino acids 233-236 of human IgG1 "ELLG" to the corresponding sequence from IgG2 "PVA" (with one amino acid deletion). It has been shown that FcγRI, FcγRII, and FcγRIII which mediate various effector functions will not bind to IgG1 when such mutations have been introduced (Ward and Ghetie 1995, Therapeutic Immunology 2:77, which is incorporated herein by reference in its entirety; and Armour et al. 1999, Eur. J. Immunol. 29:2613, which is incorporated herein by reference in its entirety). As a further example of new functionality arising from mutations described above, affinity for FcRn may be increased beyond that of wild type in some instances. This increased affinity may reflect an increased "on" rate, a decreased "off" rate or both an increased "on" rate and a decreased "off" rate. Mutations believed to impart an increased affinity for FcRn include T256A, T307A, E380A, and N434A (Shields et al. 2001, J. Biol. Chem. 276:6591, which is incorporated herein by reference in its entirety).

The FcRn BP (or FcRn BP portion of a chimeric polypeptide) may be at least 70%, at least 80%, at least 85%, at least 90%, at least 95%, at least 96%, at least 97%, at least 98%, at least 99%, or 100% identical to the Fc amino acid sequence shown in Table 5B without a signal sequence (SEQ ID NO:4), or alternatively, with a signal sequence.

Myriad mutants, fragments, variants, and derivatives are described, e.g., in PCT Publication Nos. WO 2011/069164 A2, WO 2012/006623 A2, WO 2012/006635 A2, or WO 2012/006633 A2, all of which are incorporated herein by reference in their entireties.

E. Albumins

In certain aspects, a modified clotting factor of the invention comprises a clotting factor and at least one albumin polypeptide or fragment, variant, or derivative thereof, wherein the modified clotting factor has procoagulant activity and can be expressed in vivo or in vitro in a host cell. Human serum albumin (HSA, or HA), a protein of 609 amino acids in its full-length form, is responsible for a significant proportion of the osmotic pressure of serum and also functions as a carrier of endogenous and exogenous ligands. The term "albumin" as used herein includes full-length albumin or a functional fragment, variant, derivative, or analog thereof. Examples of albumin or the fragments or variants thereof are disclosed in US Pat. Publ. Nos. 2008/0194481A1, 2008/0004206 A1, 2008/0161243 A1, 2008/0261877 A1, or 2008/0153751 A1 or PCT Appl. Publ. Nos. 2008/033413 A2, 2009/058322 A1, or 2007/021494 A2, which are incorporated herein by reference in their entireties.

The albumin binding polypeptides can compromise, without limitation, bacterial albumin-binding domains, albumin-binding peptides, or albumin-binding antibody fragments that can bind to albumin. Domain 3 from streptococcal protein G, as disclosed by Kraulis et al., FEBS Lett. 378: 190-194 (1996) and Linhult et al., Protein Sci. 11:206-213 (2002) is an example of a bacterial albumin-binding domain. Examples of albumin-binding peptides include a series of peptides having the core sequence DICLPRWGCLW (SEQ ID NO:18). See, e.g., Dennis et al., J. Biol. Chem. 2002, 277: 35035-35043 (2002). Examples of albumin-binding antibody fragments are disclosed in Muller and Kontermann, Curr. Opin. Mol. Ther. 9:319-326 (2007); Roovers et al., Cancer Immunol. Immunother. 56:303-317 (2007), and Holt et al., Prot. Eng. Design Sci., 21:283-288 (2008), which are incorporated herein by reference in their entireties.

In certain aspects, a modified clotting factor of the invention comprises a clotting factor and at least one attachment site for a non-polypeptide small molecule, variant, or derivative that can bind to albumin thereof. For example, a modified clotting factor of the invention can include one or more organic albumin binding moieties attached to the clotting factor. An example of such albumin binding moieties is 2-(3-maleimidopropanamido)-6-(4-(4-iodophenyl)butanamido)hexanoate ("Albu" tag) as disclosed by Trussel et al., Bioconjugate Chem. 20:2286-2292 (2009).

F. CTP

In certain aspects, a modified clotting factor of the invention comprises a clotting factor and at least one C-terminal peptide (CTP) of the β subunit of human chorionic gonadotropin or fragment, variant, or derivative thereof. One or more CTP peptides fused to or inserted into a clotting factor is known to increase the in vivo half-life of that protein. See, e.g., U.S. Pat. No. 5,712,122, incorporated by reference herein in its entirety. Exemplary CTP peptides include DPRFQDSSSSKAPPPSLPSPSRLPGPSDTPIL (SEQ ID NO:9) or SSSSKAPPPSLPSPSRLPGPSDTPILPQ. (SEQ ID NO:10). See, e.g., U.S. Patent Application Publication No. US 2009/0087411 A1, incorporated by reference.

G. PAS

In certain aspects, a modified clotting factor of the invention comprises a clotting factor and at least one PAS peptide or fragment, variant, or derivative thereof. A PAS peptide or PAS sequence, as used herein, means an amino acid sequence comprising mainly alanine and serine residues or comprising mainly alanine, serine, and proline residues, the amino acid sequence forming random coil conformation under physiological conditions. Accordingly, the PAS sequence is a building block, an amino acid polymer, or a sequence cassette comprising, consisting essentially of, or consisting of alanine, serine, and proline which can be used as a part of the heterologous moiety in the chimeric protein. An amino acid polymer also can form random coil conformation when residues other than alanine, serine, and proline are added as a minor constituent in the PAS sequence. By "minor constituent" is meant that that amino acids other than alanine, serine, and proline can be added in the PAS sequence to a certain degree, e.g., up to about 12%, i.e., about 12 of 100 amino acids of the PAS sequence, up to about 10%, up to about 9%, up to about 8%, about 6%, about 5%, about 4%, about 3%, i.e. about 2%, or about 1%, of the amino acids. The amino acids different from alanine, serine and proline cab be selected from the group consisting of Arg, Asn, Asp, Cys, Gln, Glu, Gly, His, Ile, Leu, Lys, Met, Phe, Thr, Trp, Tyr, and Val. Under physiological conditions, a PAS peptide forms a random coil conformation and thereby can mediate an increased in vivo and/or in vitro stability to a recombinant protein of the invention, and has procoaguiant activity.

Non-limiting examples of the PAS peptides include ASPAAPAPASPAAPAPSAPA (SEQ ID NO: 11), AAPASPAPAAPSAPAPAAPS (SEQ ID NO:12), APSSPSPSAPSSPSPASPSS (SEQ ID NO:13), APSSPSPSAPSSPSPASPS (SEQ ID NO:14), SSPSAPSPSSPASPSPSSPA (SEQ ID) NO:15), AASPAAPSAPPAAASPAAPSAPPA (SEQ ID NO:16), ASAAAPAAASAAASAPSAAA (SEQ ID NO:17) or any variants, derivatives, fragments, or combinations thereof. Additional examples of PAS sequences are known from, e.g., US Pat. Publ. No. 2010/0292130 A1 and PCT Appl. Publ. No. WO 2008/155134 A1. European issued patent EP2173890.

H. HAP

In certain aspects, a modified clotting factor of the invention comprises a clotting factor and at least one homo-amino acid polymer (HAP) peptide or fragment, variant, or derivative thereof. A HAP peptide can comprise a repetitive sequence of glycine, which has at least 50 amino acids, at least 100 amino acids, 120 amino acids, 140 amino acids, 160 amino acids, 180 amino acids, 200 amino acids, 250 amino acids, 300 amino acids, 350 amino acids, 400 amino acids, 450 amino acids, or 500 amino acids in length. A HAP sequence is capable of extending half-life of a moiety fused to or linked to the HAP sequence. Non-limiting examples of the HAP sequence includes, but are not limited to (Gly), $(Gly_4Ser)_n$ or $S(Gly_4Ser)_n$, wherein n is 1, 3, 3, 4, 5, 6, 7, 8, 9, 10, 11, 12, 13, 14, 15, 16, 17, 18, 19, or 20. In one embodiment, n is 20, 21, 22, 23, 24, 25, 26, 26, 28, 29, 30, 31, 32, 33, 34, 35, 36, 37, 38, 39, or 40. In another embodiment, n is 50, 60, 70, 80, 90, 100, 110, 120, 130, 140, 150, 160, 170, 180, 190, or 200. See, e.g., Schlapschy M et at, Protein Eng. Design Selection, 20: 273-284 (2007).

I. Transferrin

In certain aspects, a modified clotting factor of the invention comprises at least one transferrin peptide or fragment, variant, or derivative thereof linked to or inserted into the clotting factor, wherein the modified clotting factor has procoagulant activity. Any transferrin can be linked to or inserted into a modified clotting factor of the invention. As an example, wild-type human Tf (Tf) is a 679 amino acid protein, of approximately 75 KDa (not accounting for glycosylation), with two main domains, N (about 330 amino acids) and C (about 340 amino acids), which appear to originate from a gene duplication. See GenBank accession numbers NM001063, XM002793, M12530, XM039845, XM 039847 and S95936 (www.ncbi.nlm.nih.gov), all of which are herein incorporated by reference in their entirety.

Transferrin transports iron through transferrin receptor (TfR)-mediated endocytosis. After the iron is released into an endosomal compartment and Tf-TfR complex is recycled to cell surface, the Tf is released back extracellular space for next cycle of iron transporting. Tf possesses a long half-life that is in excess of 14-17 days (Li et al., Trends Pharmacol. Sci. 23:206-209 (2002)). Transferrin fusion proteins have been studied for half-life extension, targeted deliver for cancer therapies, oral delivery and sustained activation of proinsulin (Brandsma et al., Biotechnol. Adv., 29: 230-238 (2011); Bai et al., Proc. Natl. Acad. Sci. USA 102:7292-7296 (2005); Kim et al., J. Pharmacol. Exp. Ther., 334:682-692 (2010); Wang et al., J. Controlled Release 155:386-392 (2011)).

J. PEG

In certain aspects, a modified clotting factor of the invention comprises a clotting factor and at least one attachment site for a non-polypeptide heterologous moiety or fragment, variant, or derivative thereof linked to or inserted into the clotting factor, wherein the modified clotting factor has procoagulant activity. For example, a modified clotting factor of the invention can include one or more polyethylene glycol (PEG) moieties attached to or inserted into the clotting factor, wherein the modified clotting factor has procoagulant activity.

PEGylated clotting factor can refer to a conjugate formed between clotting factor and at least one polyethylene glycol (PEG) molecule. PEG is commercially available in a large variety of molecular weights and average molecular weight ranges. Typical examples of PEG average molecular weight ranges include, but are not limited to, about 200, about 300, about 400, about 600, about 1000, about 1300-1600, about 1450, about 2000, about 3000, about 3000-3750, about 3350, about 3000-7000, about 3500-4500, about 5000-7000, about 7000-9000, about 8000, about 10000, about 8500-11500, about 16000-24000, about 35000, about 40000, about 60000, and about 80000 daltons. These average molecular weights are provided merely as examples and are not meant to be limiting in any way.

A modified clotting factor of the invention can be PEGylated to include mono- or poly- (e.g., 2-4) PEG moieties. PEGylation can be carried out by any of the PEGylation reactions known in the art. Methods for preparing a PEGylated protein product will generally include (i) reacting a polypeptide with polyethylene glycol (such as a reactive ester or aldehyde derivative of PEG) under conditions whereby the peptide of the invention becomes attached to one or more PEG groups; and (ii) obtaining the reaction product(s). In general, the optimal reaction conditions for the reactions will be determined case by case based on known parameters and the desired result.

There are a number of PEG attachment methods available to those skilled in the art, for example Malik F et al., *Exp. Hematol.* 20:1028-35 (1992); Francis, *Focus on Growth Factors* 3(2):4-10 (1992); European Pat. Pub. Nos. EP0401384, EP0154316, and EP0401384; and International Pat. Appl. Pub. Nos. WO92/16221 and WO95/34326. As a non-limiting example, clotting factor variants can contain cysteine substitutions in one or more permissive loops as described herein, and the cysteines can be further conjugated to PEG polymer. See Mei et al., *Blood* 116:270-279 (2010) and U.S. Pat. No. 7,632,921, which are incorporated herein by reference in their entireties.

K. HES

In certain aspects, a modified clotting factor of the invention comprises a clotting factor and at least one hydroxyethyl starch (HES) polymer conjugated to or inserted into the clotting factor, wherein the modified clotting factor has procoagulant activity. HES is a derivative of naturally occurring amylopectin and is degraded by alpha-amylase in the body. HES exhibits advantageous biological properties and is used as a blood volume replacement agent and in hemodilution therapy in the clinics. See, e.g., Sommermeyer et al., *Krankenhauspharmazie* 8:271-278 (1987); and Weidler et al., *Arzneim.-Forschung/Drug Res.* 41: 494-498 (1991).

HES is mainly characterized by the molecular weight distribution and the degree of substitution. HES has a mean molecular weight (weight mean) of from 1 to 300 kD, from 2 to 200 kD, from 3 to 100 kD, or from 4 to 70 kD. Hydroxyethyl starch can further exhibit a molar degree of substitution of from 0.1 to 3, from 0.1 to 2, from 0.1 to 0.9, or from 0.1 to 0.8, and a ratio between C2:C6 substitution in the range of from 2 to 20 with respect to the hydroxyethyl groups. HES with a mean molecular weight of about 130 kD is VOLUVEN® from Fresenius. VOLUVEN® is an artificial colloid, employed, e.g., for volume replacement used in the therapeutic indication for therapy and prophylaxis of hypovolaemia. There are a number of HES attachment methods available to those skilled in the art, e.g., the same PEG attachment methods described above.

L. PSA

In certain aspects, a modified clotting factor of the invention comprises a clotting factor and at least one polysialic acid (PSA) polymer conjugated to or inserted into the clotting factor, wherein the modified clotting factor has procoagulant activity. PSAs are naturally occurring unbranched polymers of sialic acid produced by certain bacterial strains and in mammals in certain cells. See, e.g., Roth J. et al. (1993) in *Polysialic Acid: From Microbes to Man*, eds. Roth J., Rutishauser U., Troy F. A. (BirkhäuserVerlag, Basel, Switzerland), pp. 335-348. PSAs can be produced in various degrees of polymerization from n=about 80 or more sialic acid residues down to n=2 by limited acid hydrolysis or by digestion with neuraminidases, or by fractionation of the natural, bacterially derived forms of the polymer. There are a number of PSA attachment methods available to those skilled in the art, e.g., the same PEG attachment methods described above. In certain aspects, an activated PSA can also be attached to a cysteine amino acid residue on the clotting factor. See, e.g., U.S. Pat. No. 5,846,951.

M. Clearance Receptors

In certain aspects, the in vivo half-life of a modified clotting factor of the invention can be extended where the modified clotting factor comprises at least one fragment of a clotting factor clearance receptor or fragment, variant, or derivative thereof linked to or inserted into the clotting factor, wherein the modified clotting factor has procoagulant activity. For example, insertion of soluble forms of clearance receptors, such as the low density lipoprotein-related protein receptor LRP1, or fragments thereof, can block binding of FVII to clearance receptors and thereby extend its in vivo half-life. LRP1 is a 600 kDa integral membrane protein that is implicated in the receptor-mediate clearance of a variety of proteins, including FVIII. See, e.g., Lenting et al., Haemophilia 16:6-16 (2010). Other suitable FVIII clearance receptors are, e.g., LDLR (low-density lipoprotein receptor), VLDLR (very low-density lipoprotein receptor), and megalin (LRP-2), or fragments thereof. See, e.g., Bovenschen et al., Blood 106:906-912 (2005); Bovenschen, Blood 116: 5439-5440 (2010); Martinelli et al., Blood 116:5688-5697 (2010).

III. DOSING STRATEGIES FOR CLOTTING FACTORS

The present invention provides a dosing strategy for a clotting factor. A good dosing strategy provides reduced interpatient variability in pharmacokinetics and pharmacodynamics. While clotting factors have routinely been dosed based on the body weight of the patient, the present invention shows that a fixed dosing regimen is suitable for clotting factors that have a wide therapeutic window.

In one aspect, the invention provides methods of administering a clotting factor to a subject in need thereof, comprising administering to the subject a fixed dose of a clotting factor. Administration of the clotting factor is a replacement therapy by providing a recombinant clotting factor to a subject with clotting factor deficiency. Administration of the clotting factor can reduce the number of bleeding episodes or prevent the symptoms of a bleeding disorder in the subject.

In another aspect, the invention provides a method of reducing, ameliorating, or preventing one or more symptoms of a bleeding disease or disorder in a subject comprising administering a fixed dose of a clotting factor to the subject in need thereof. The invention also provides use of a fixed dose of a clotting factor for the manufacture of a medicament for reducing, ameliorating, or preventing one or more symptoms of a bleeding disease or disorder in a subject in need thereof. The one or more symptoms of a bleeding disease or disorder can be one or more bleeding episodes. The bleeding episodes can be spontaneous or caused by trauma or surgery. The invention can control bleeding or prevent one or more bleeding episodes. The subject can be bleeding at the time of administration or be expected to be bleeding, or can be susceptible to bleeding as the result of minor hemorrhage, hemarthroses, superficial muscle hemorrhage, soft tissue hemorrhage, moderate hemorrhage, intramuscle or soft tissue hemorrhage with dissection, mucous membrane hemorrhage, hematuria, major hemorrhage, hemorrhage of the pharynx, hemorrhage of the retropharynx, hemorrhage of the retroperitonium, hemorrhage of the central nervous system, bruises, cuts, scrapes, joint hemorrhage, nose bleed, mouth bleed, gum bleed, intracranial bleeding, intraperitoneal bleeding, minor spontaneous hemorrhage, bleeding after major trauma, moderate skin bruising, or spontaneous hemorrhage into joints, muscles, internal organs or the brain. Such subjects also include those in need of peri-operative management, such as management of bleeding associated with surgery or dental extraction. In one aspect, the subject is in need of prophylaxis of one or more bleeding episodes. In another aspect, the subject is in need of individualized interval prophylaxis. In other aspects, the subject is in need of on-demand treatment or episodic treatment of one or more bleeding episodes. In still other aspects, the subject is in need of perioperative management of one or more bleeding episodes.

In other aspects, the invention includes a method of manufacturing a pharmaceutical composition, or compositions comprising formulating a fixed dose of a clotting factor. The fixed dose manufactured by the present method can be administered to a subject in need thereof. The pharmaceutical composition(s) can comprise, consist essentially or, or consist of a fixed dose of a clotting factor and one or more pharmaceutically acceptable carrier or excipient, but does not comprise any additional amount of the clotting factor. In some embodiments, the entire fixed dose is administered to the subject, i.e., no portion of the composition is left unused.

In some aspects, the invention provides a pharmaceutical composition comprising a fixed dose of a clotting factor and a pharmaceutically acceptable carrier for use to reduce, ameliorate, or prevent one or more symptoms of a bleeding disease or disorder to a subject in need thereof. The pharmaceutical composition can comprise, consist essentially or, or consist of a fixed dose of a clotting factor and one or more pharmaceutically acceptable carrier or excipient, but does not comprise any additional amount of the clotting factor. In some embodiments, the entire fixed dose is administered to the subject, i.e., no portion of the composition is left unused. In certain embodiments, the pharmaceutical composition comprises a fixed dose of a clotting factor, wherein the fixed dose is provided in two or more (e.g., two, three, four, or five) vials. The total contents of which provide the fixed dosage of the clotting factor.

A clotting factor can be formulated as a pharmaceutical composition. The pharmaceutical composition can be formulated for administration to humans. The pharmaceutical compositions used in the methods of this invention comprise pharmaceutically acceptable carriers, including, e.g., ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Various methods of formulating the invention are well known in the art.

In still other aspects, the invention is directed to a kit for administration of a fixed dose amount of a clotting factor comprising one or more containers (e.g., vials) of a pharmaceutical composition and an instructional material. In one embodiment, a kit comprises a single vial of a pharmaceutical composition comprising a fixed dose of a clotting factor and an instructional material, wherein the composition in the single vial is to be administered in its entirety to a subject in need thereof. The instruction material that can be inserted in the kit can comprise instructions to administer the pharmaceutical composition of the clotting factor to the subject. In another embodiment, a kit comprises an x number of the pharmaceutical compositions, wherein x is any integer, and an instructional material, wherein each of the pharmaceutical compositions, e.g., each vial, comprises a portion of a clotting factor, wherein the total amount of the clotting factor, when combined, is a fixed dose for a subject in need thereof. For example, x can be 1, 2, 3, 4, 5, 6, 7, 8, 9, or 10. When the kit comprises two or more (i.e., x=2 or more) pharmaceutical compositions (e.g., vials), each comprising a portion of a clotting factor, the two or more compositions can be combined together into one vial or syringe. Techniques for combining vials, e.g., by using a large syringe, are known in the art. The combination of the portions of the two or more compositions provides the fixed dose of the clotting factor that is to be administered to the subject in need thereof. In some embodiments, the entire fixed dose is administered to the subject, i.e., no portion of the composition is left unused.

In one example, a kit for administration of a fixed dose amount of a clotting factor (e.g., a fixed dose of 4000 IU) comprises a first container of a pharmaceutical composition and a second container of a pharmaceutical composition, wherein the first container comprises a first portion of a fixed dose of a clotting factor (e.g., a vial containing 2,000 IU of the clotting factor) and the second container comprises a second portion of the fixed dose of the clotting factor (e.g., a second vial containing 2,000 IU of the clotting factor) and wherein the total amount of the first container and the second container, when combined, is the fixed dose (e.g., 4,000 IU). In another example, a kit for administration of a fixed dose amount of a clotting factor (e.g., a fixed dose of 6000 IU) comprises a first container of a pharmaceutical composition, a second container of a pharmaceutical composition, and a third container of a pharmaceutical composition, wherein the first container comprises a first portion of a fixed dose of a modified clotting factor (e.g., a vial containing 2,000 IU of the clotting factor), the second container comprises a second portion of the fixed dose of the clotting factor (e.g., a second vial containing 2,000 IU of the clotting factor), and the third container comprises a third portion of the fixed dose of the clotting factor (e.g., a third vial containing 2,000 IU of the clotting factor) and wherein the total amount of the first container, the second container, and the third container is the fixed dose (e.g., 6,000 IU). In other examples, the first portion of the first pharmaceutical composition, the second portion of the pharmaceutical composition, and the third portion of the pharmaceutical composition are the same or different. The combination of the first and second composition (i.e., vials) and the third, if present, is the fixed dose. The entire fixed dose is then administered to the subject in need thereof.

In some embodiments, the two or more pharmaceutical compositions (e.g., vials) in a kit can be administered separately. For example, a first pharmaceutical composition comprising a first portion of a fixed dose of a clotting factor is first administered to a subject in need thereof, and a second pharmaceutical composition comprising a second portion of a fixed dose of a clotting factor is then administered to the subject.

The present invention also identifies the fixed dose that can treat or prevent one or more bleeding episodes in a subject regardless of the body weight. Administration of the appropriate dosing amount for the dosing interval can achieve a plasma trough level of a clotting activity at least about 1 IU/dl or above 1 IU/dl during the interval in a subject administered with a clotting factor. In one embodiment, the invention includes a dosing amount (or ranges of the dosing amount) and a dosing interval (or ranges of the dosing interval) that can maintain a plasma trough level of a clotting activity at least about 1 IU/dl (1%) or above 1 IU/dl (1%), at least about 2 IU/dl (2%) or above 2 IU/dl (2%), at least about 3 IU/dl (3%) or above 3 IU/dl (3%), at least about 4 IU/dl (4%) or above 4 IU/dl (4%), at least about 5 IU/dl (5%) or above 5 IU/dl (5%), at least about 6 IU/dl (6%) or above 6 IU/dl (6%), at least about 7 IU/dl (7%) or above 7 IU/dl (7%), at least about 8 IU/dl (8%) or above 8 IU/dl (8%), at least about 9 IU/dl (9%) or above 9 IU/dl (9%), at least about 10 IU/dl (10%) or above 10 IU/dl (10%), at least about 11 IU/dl (11%) or above 11 IU/dl (11%), at least about 12 IU/dl (12%) or above 12 IU/dl (12%), at least about 13 IU/dl (13%) or above 13 IU/dl (13%), at least about 14 IU/dl (14%) or above 14 IU/dl (14%), at least about 15 IU/dl (15%) or above 15 IU/dl (15%), at least about 16 IU/dl (16%) or above 6 IU/dl (16%), at least about 17 IU/dl (17%) or above 17 IU/dl (17%) at least about 18 IU/dl (8%) or above 18 IU/dl (18%), at least about 19 IU/dl (19%) or above 19 IU/dl (19%), at least about 20 IU/dl (20%) or above 20 IU/dl (20%) throughout the interval.

In another embodiments, a plasma trough level of a clotting factor is maintained between about 1% and about 5%, between about 1% and about 6%, between about 1% and about 7%, between about 1% and about 8%, between about 1% and about 9%, between about 1% and about 10%, between about 1% and about 12%, between about 1% and about 14%, between about 1% and about 15%, between about 1% and about 17%, between about 1% and about 19%, between about 1% and about 20%, between about 1% and about 22%, between about 1% and about 24%, between about 1% and about 25%, between about 1% and about 30%, between about 1% and about 35%.

In other embodiments, the trough is 1-5 or 1-3 IU/dl after about 6, about 7, about 8, about 9, about 10, about 11, about 12, about 13 or about 14 days after administration of a clotting factor. In some embodiments, the plasma level of the clotting factor reaches an average trough of at least about 1 IU/dl after at least about 6 days or reaches a trough of at least about 1, 2, 3, 4, or 5 IU/dl after at least about 6 days in a subject. In some embodiments, the plasma level of the clotting factor reaches an average trough of about 1-5 or 1-3 IU/dl. Such trough or average trough may be reached after about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, or about 40 days.

In some embodiments, a dosing amount (or ranges of the dosing amount) and a dosing interval (or ranges of the dosing interval) are selected to reduce or decrease the frequency of bleeding or bleeding disorder. In other embodiments, the dosing amount (or ranges of the dosing amount) and the dosing interval (or ranges of the dosing interval) of a clotting factor stops on-going, uncontrollable bleeding or bleeding episodes in a subject administered with the dosing amount during the dosing interval. In still other embodiments, the dosing amount (or ranges of the dosing amount) and the dosing interval (or ranges of the dosing interval) of a clotting factor prevents spontaneous bleeding or bleeding episodes in a subject susceptible to such spontaneous bleeding or bleeding episodes.

In one aspect, a fixed dose of a FIX polypeptide is about 4,000 IU per dose, 6000 IU or about 8,000 IU per dose. In one embodiment, a dosing interval is at least about every five days, about every six days, at least about every seven days, at least about every eight days, at least about every nine days, at least about every ten days, at least about every 11 days, at least about every 12 days, at least about every 13 days, at least about every 14 days, at least about every 15 days, at least about every 16 days, at least about every 17 days, at least about every 18 days, at least about every 19 days, at least about every 20 days, or at least about every 21 days. In another embodiment, a fixed dose of a FIX polypeptide is about 4,000 IU per dose and is administered weekly, i.e., once per week. In other embodiments, a fixed dose of a FIX polypeptide is about 8,000 IU per dose and is administered every 10 days or once every two weeks. In yet other embodiments, the fixed dose of a long-acting FIX polypeptide is not calculated by the formula:

Number of factor IX IU required (IU)=Body Weight (kg)×Desired Factor IX Increase (% or IU/dL)×1 IU/kg per IU/dL)　　(A)

In certain aspects of the invention, the method, the use, the pharmaceutical composition, or the kit further comprises administering an additional dosing amount of a clotting factor.

In certain embodiments, the fixed dosing strategy is a stratified dosing regimen. For example, the fixed dose can be stratified into two or more dose sizes based on specified weight categories. The weight categories can be low body weight, normal body weight, and high body weight. In one embodiment, the fixed dose is stratified into three dose sizes suitable for subjects with low, normal, or high body weight. The normal, low, or high body weight can be determined based on age, height, gender, frame size, general health, or any combination thereof or independently of age, height, gender, frame size, general health, or any combination thereof. In another embodiment, a subject has a low body weight, and the fixed dose of a long-acting FIX polypeptide is about 5,000 IU per dose or about 6,000 IU per dose, which is administered at an interval longer than 7 days, e.g., every 10 days. In other embodiments, a subject has a normal body weight and the fixed dose is about 7500 IU per dose or about 8000 IU per dose, which is administered at an interval longer than 7 days, e.g., every 10 days. In some embodiments, a subject has a high body weight and the fixed dose is about 10000 IU per dose administered every 10 days or about 12000 IU per dose administered every 10 days.

The dosing interval can, alternatively, be an individualized interval that is determined for each subject based on pharmacokinetic data or other information about that subject. The individualized dose/dosing interval combination may be the same as those for fixed interval regimens in the preceding paragraphs, or may differ. The regimen can initially be at a fixed dosing interval, and then it can change to an individualized dosing interval.

In certain embodiments of the invention, the method of the invention further comprises measuring a baseline FIX activity of a subject prior to the initial administration of a FIX polypeptide. Measuring of a baseline FIX activity can employ any known clotting assays in the art, e.g., one step aPTT assay, two step chromogenic assay, ROTEM, TGA, or etc.

In one aspect, a fixed dose of a FVIII polypeptide is about 2000 IU, about 2,500 IU, about 3,000 IU, about 3,500 IU, or about 4,000 IU per dose. In one embodiment, the fixed dose is administered twice a week (i.e., two times per week). In another embodiment, the fixed dose is administered weekly (i.e., once a week). In other embodiments, the entire fixed dose is administered to the subject, i.e., no portion of the composition is left unused. In yet other embodiments, the fixed dose of a long-acting FVIII polypeptide is not calculated by the formula:

Number of factor FVIII IU required (IU)=Body Weight (kg)×Desired Factor FVIII Increase (IU/ dL or % of normal)×0.5(IU/kg per IU/dL)　　(B)

IV. METHODS OF MAKING

A clotting factor can be manufactured in a host cell comprising a vector encoding the clotting factor. As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

A gene expression control sequence as used herein is any regulatory nucleotide sequence, such as a promoter sequence or promoter-enhancer combination, which facilitates the efficient transcription and translation of the coding nucleic acid to which it is operably linked. The gene expression control sequence may, for example, be a mammalian or viral promoter, such as a constitutive or inducible promoter. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

Examples of vectors include, but are not limited to viral vectors or plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids may be custom designed using standard molecular biology techniques to remove and/or add specific fragments of DNA.

The expression vector or vectors are then transfected or co-transfected into a suitable target cell, which will express the polypeptides. Transfection techniques known in the art include, but are not limited to, calcium phosphate precipitation (Wigler et al. (1978) Cell 14:725), electroporation (Neumann et al. (1982) EMBO J 1:841), and liposome-based reagents. A variety of host-expression vector systems may be utilized to express the proteins described herein including both prokaryotic and eukaryotic cells. These include, but are not limited to, microorganisms such as bacteria (e.g., *E. coli*) transformed with recombinant bacteriophage DNA or plasmid DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus or tobacco mosaic virus) or transformed with recombinant plasmid expression vectors (e.g., Ti plasmid) containing an appropriate coding sequence; or animal cell systems, including mammalian cells (e.g., HEK 293, CHO, Cos, HeLa, HKB11, and BHK cells).

In one embodiment, the host cell is a eukaryotic cell. As used herein, a eukaryotic cell refers to any animal or plant cell having a definitive nucleus. Eukaryotic cells of animals include cells of vertebrates, e.g., mammals, and cells of invertebrates, e.g., insects. Eukaryotic cells of plants specifically can include, without limitation, yeast cells. A eukaryotic cell is distinct from a prokaryotic cell, e.g., bacteria.

In certain embodiments, the eukaryotic cell is a mammalian cell. A mammalian cell is any cell derived from a mammal. Mammalian cells specifically include, but are not limited to, mammalian cell lines. In one embodiment, the mammalian cell is a human cell. In another embodiment, the mammalian cell is a HEK 293 cell, which is a human embryonic kidney cell line. HEK 293 cells are available as CRL-1533 from American Type Culture Collection, Manassas, Va., and as 293-H cells, Catalog No. 11631-017 or 293-F cells, Catalog No. 11625-019 from Invitrogen (Carlsbad, Calif.). In some embodiments, the mammalian cell is a PER.C6® cell, which is a human cell line derived from retina. PER.C6® cells are available from Crucell (Leiden, The Netherlands). In other embodiments, the mammalian cell is a Chinese hamster ovary (CHO) cell. CHO cells are available from American Type Culture Collection, Manassas, Va. (e.g., CHO-K1; CCL-61). In still other embodiments, the mammalian cell is a baby hamster kidney (BHK) cell. BHK cells are available from American Type Culture Collection, Manassas, Va. (e.g., CRL-1632). In some embodiments, the mammalian cell is a HKB11 cell, which is a hybrid cell line of a HEK293 cell and a human B cell line. Mei et al., *Mol. Biotechnol.* 34(2): 165-78 (2006).

The method can further comprise purification steps. Various known purifications steps are well known in the art.

Having now described the present invention in detail, the same will be more clearly understood by reference to the following examples, which are included herewith for purposes of illustration only and are not intended to be limiting of the invention. All patents and publications referred to herein are expressly incorporated by reference.

EXAMPLES

Example 1

Population Pharmacokinetic Analysis of a Long-Acting Recombinant Factor IX-Fc Fusion Protein (rFIXFc) in Patients with Severe Hemophilia B BACKGROUND: Population pharmacokinetic (popPK) models are developed to understand the sources of variability in dose requirements (covariates) and to help individualize dosing regimens if necessary. Dosing histories and patient-specific data are used to gain an understanding of drug disposition in order to discern specific demographic and/or clinical factors that may be predictors of PK parameters. By characterizing the population PK of long-acting FIX-Fc (rFIXFc) in patients with severe hemophilia B (≤2 IU/dL plasma FIX activity), a model of estimated population PK parameters of rFIXFc can be established. This model may assist physicians who wish to tailor dosing for individual patients with sparse PK samples. This model may also help determine the suitability of rFIXFc for a fixed dosing regimen.

METHODS: Male subjects with severe hemophilia B were included from a phase 1/2a clinical study (n=12) and a phase 3 clinical study (B-LONG, n=123) of rFIXFc. Male subjects with severe hemophilia B were treated with long-lasting recombinant FIX-Fc (rFIXFc) in an amount of 50 IU/kg or 100 IU/kg. The subjects ranged in age from 12 to 76 years and in body weight from 45 to 186 kg. The modeling dataset included 135 baseline PK profiles at Week 1, as well as 21 repeat PK profiles at Week 26, with a total of 1400 measured FIX activity records. The final population PK model was validated using 1027 trough/peak FIX activity records from 119 patients.

In the popPK analysis, plasma FIX activity was measured by the one-stage (activated partial thromboplastin time) clotting assay. Corrected FIX activity was calculated using the formula:

Corrected FIX activity=Measured FIX activity−Baseline−Residual decay.

Baseline FIX activity was defined as the lowest level of activity (LLACT) recorded at screening, predose, postdose, or from historical clinical records. The baseline is defined as 0 when the LLACT is less than 1% (lower limit of quantification). The baseline FIX activity is equal to LLACT when LLACT is from 1% to 2% (i.e., 1≤LLACT≤2).

Prestudy residual decay was performed using terminal half-life obtained from a noncompartmental analysis of the individual data by the following formula:

Residual decay=(predose−baseline)×$e^{-decay\ rate \times time}$.

Clearance was presented by the following formula:

$CL$=Typical $CL$×(BW/Typical BW)$^{exponent}$, where typical BW is 73 kg.

Volume of distribution was presented by the following formula:

$V$=Typical $V$×(BW/Typical BW)$^{exponent}$, where typical BW is 73 kg.

For the popPK model development, NONMEM VII version 1.0 (ICON Development Solutions, Ellicott City, Md.) was used. The modeling and qualification steps are presented below in Table 1.

TABLE 1

| \multicolumn{2}{c}{Modeling and Qualification Steps} | |
|---|---|
| Steps | Model selection |
| Base model and Inter-individual variability (IIV) evaluation | Base Model, IIV on CL/V1/Q2/V2/Q3 |
| Inter-occasion variability (IOV) evaluation | Base Model with IOV on CL and V1 |
| Covariate Modelling | Final model, body weight as covariate on CL and V1 |
| Internal qualification (bootstrap and VPC) | |

TABLE 1-continued

Modeling and Qualification Steps

| Steps | Model selection |
|---|---|
| External qualification using trough/peak records | |

CL, clearance;
V, volume of distribution;
Q, inter-compartmental clearance;
VPC, visual predictive check A first order conditional estimation with interaction method (FOCET) was used to estimate the popPK parameters. Residual errors were modeled as combined proportional and additive errors. Stepwise forward addition (p<0.005) and backward elimination (p<0.001) covariate modeling was performed. Potential covariates assessed in this analysis included: body weight (BW), Age, Race, Blood type, Human Immunodeficiency Virus status, Hepatitis C Virus status, haematocrit, $IgG_1$ and albumin concentration, and FIX genotype.

Model qualifications included bootstrap, visual predictive check (VPC) and validation with trough/peak records. The mean relative prediction error (an indicator of accuracy) was calculated as:

$$\frac{1}{N}\sum_{i=1}^{i=N} \frac{[DV - IPRED]}{DV}$$

RESULTS: The rFIXFc disposition was best described by a three-compartment base model (FIG. 1). The model was further improved by including intra-subject random changes at different occasions (i.e., inter-occasion variability, IOV) for CL and V1 (FIG. 2). IOV was smaller than inter-individual variability (IIV), indicating that individual PK was more accurate than the mean popPK for individual PK prediction.

BW was the only statistically significant covariate on CL and V1 (volume of the central compartment). However, the impact of body weight on the PK of rFIXFc was limited. Body weight was found to be a significant covariate for rFIXFc disposition (FIG. 3), although the impact of BW was limited. For example, the BW exponent on CL and V1 was 0.436 and 0.396, respectively, and inclusion of BW reduced inter-individual variability (IIV) for both CL and V1 only by 3.4% and 2.5%, respectively. None of the other covariates assessed, including age, race, blood type or genotype, were significant covariates in this model.

The final popPK model is summarized below in Table 2.

TABLE 2

Summary of the final rFIXFc population pharmacokinetic model.

| Parameter | Population Estimate | 95% non-parametic CI from bootstrap[a] | IIV[b] (%) | IOV (%) |
|---|---|---|---|---|
| $CL = Typical\ CL \times \left(\frac{BW}{73}\right)^{0.436}$ | | | | |
| Typical CL for a 73 kg subject (dL/h) | 2.39 | 2.29, 2.49 | 17.7 | 15.1 |
| BW exponent on CL | 0.436 | 0.272, 0.584 | | |
| $V1 = Typical\ V1 \times \left(\frac{BW}{73}\right)^{0.396}$ | | | | |
| Typical V1 for a 73 kg subject (dL) | 71.4 | 58.5, 76.0 | 21.7 | 17.4 |
| BW exponent on V1 | 0.396 | 0.169, 0.580 | | |
| Q2 (dL/h) | 1.67 | 1.35, 1.89 | 35.8 | — |
| V2 (dL) | 87.0 | 79.0, 95.5 | 46.2 | — |
| Q3 (dL/h) | 39.3 | 16.6, 141 | — | — |
| V3 (dL) | 39.9 | 36.6, 52.4 | 37.7 | — |
| Residual Error: | Proportional 10.6% | Additive 0.24 IU/dL | | |

CI, confidence interval;
IIV, inter-individual variability;
IOV, inter occasion variability;
CL, clearance;
BW, body weight;
V, volume of distribution;
Q, inter-compartmental clearance For a typical 73 kg subject, the predicted popPK values for clearance, volume of central compartment, and volume of distribution at steady state are 2.39 dL/h, 71.4 dL, and 198 dL, respectively. Goodness-of-fit plots show that the predicted popPK data generated by the model closely mimic the observed FIX activity data (FIG. 4).

The results of the popPK model were validated using the observed FIX activity data. The median and 80% interval for observed and predicted FIX activity time profiles nearly overlapped, indicating that the final model was able to reproduce both the central tendency and variability of the observed FIX activity data on the time scale (FIG. 5). The strong correlation between observed and predicted FIX activities in the trough/peak dataset suggested that the final popPK model is predictive (FIG. 6).

Finally, the overall relative prediction error was −3.23% with a 95% confidence interval of −5.27% to −1.23%. Post hoc estimates from this popPK analysis were very similar to the results from the conventional PK analysis shown below in Table 3.

TABLE 3

Post hoc empirical Bayesian estimates of key PK parameters.

| Parameter | Phase 3 Mean (SD) | Phase 1/2a Mean (SD) |
|---|---|---|
| Clearance (CL), mL/h/kg | 3.42 (0.89) | 2.82 (0.58) |
| Volume of central compartment (V1), mL | 102 (29.6) | 96.2 (24.7) |
| Incremental in vivo recovery, IU/dL per IU/kg | 1.02 (0.45) | 1.04 (0.19) |
| Volume of distribution at steady-state (Vss), mL/kg | 297 (90.5) | 234 (70.8) |
| Terminal Half-life, h | 86.7 (27.9) | 70.9 (13.9) |
| Mean residence time (MRT), h | 89.4 (25.9) | 82.5 (15.5) |

SD, standard deviation

CONCLUSIONS: The three-compartment popPK model predicted disposition of rFIXFc with modest inter-individual variability (IIV). Individual PK parameters derived from the three-compartment popPK model were similar to those derived from the two-compartment conventional PK analysis, indicating a limited 3rd compartment contribution. For a typical 73 kg subject, the popPK model predicted a clearance of 2.39 dL/h; volume of central compartment of 71.4 dL; and volume of distribution at steady state of 198 dL. The only significant covariate assessed in the popPK model was BW, although its impact on rFIXFc PK variability was limited.

Drugs with body weight effect on clearance ($\theta_{BW\_CL}$) and body weight effect on the central volume of distribution ($\theta_{BW\_V1}$) equal to or less than 0.5 are considered good candidates for fixed dosing regimens due to the limited impact of patient body weight on PK variability. Here, rFIXFc had $\theta_{BW\_CL}$ and $\theta_{BW\_V1}$ values of 0.436 and 0.396, respectively (Table 2). Furthermore, the inclusion of BW in the population PK model resulted in a modest reduction of approximately 3% in IIV for both CL and V1. These results indicate that body weight had a minimal impact on PK variability and suggest that rFIXFc is suitable for a fixed dosing regimen.

The final popPK model can be used to simulate dosing regimens and intervals for routine prophylaxis, control and prevention of bleeding episodes, and peri-operative management. This model may assist physicians who wish to tailor dosing for individual patients with sparse PK samples.

Example 2

Fixed Dosing

The body weight of adult patients has a limited impact on PK variability among patients. Therefore, rFIXFc is suitable for fixed dosing regimens that do not use the formula:

Number of factor FIX IU required (IU)=Body Weight (kg)×Desired Factor FIX Increase (IU/dL or % of normal)×0.5(IU/kg per IU/dL).

In this example, fixed dose regimens are established using vials of rFIXFc that contain 2,000 IU per vial. In one alternative, the entire population of adult patients is treated with 2 vials of rFIXFc once weekly. Alternatively, stratified fixed dosing is applied based on the BW range in which the patient belongs to.

METHODS: Patients with hemophilia B are categorized into one of three categories: (i) low body weight; (ii) normal body weight; and (iii) high body weight. Patients weighing less than 57 kg are categorized as low body weight. Patients weighing between 57 and 104 kg are categorized as normal body weight. Patients weighing more than 104 kg are categorized as high body weight.

Patients in the low body weight category are treated with a single vial of fixed dose long acting FIXFc (i.e., 2,000 IU total) once weekly. Patients in the normal body weight category are treated with two vials of fixed dose long-acting rFIXFc (i.e., 4,000 IU total) once weekly. Patients in the high body weight category are treated with three vials of fixed dose long-acting rFIXFc (i.e., 6,000 IU total) once weekly.

RESULTS: The PK properties of long-acting rFIXFc are minimally affected by the BW. As FIGS. 7A and 7B show, the $97.5^{th}$, median, and $2.5^{th}$ percentiles of the simulated FIX activity-time profiles at steady state in 1000 subjects following fixed dosing (4000 IU once weekly and 8000 IU every 10 days; dotted lines) significantly overlap with those of BW-based dosing (50 IU/kg once weekly and 100 IU/kg every 10 days; solid lines). FIG. 8 shows that the percentages of population within the target therapeutic range following the fixed dosing and body weight (BW)-based dosing approaches in the BW-stratified population are similar. These data demonstrate that the clotting factors having a wide therapeutic window can be used for fixed dosing regimen: for example, this allows the physician to treat patients with fixed dose regimens of long-acting rFIXFc, eliminating the need to use formulaic dose calculation methods.

Example 3

Population Pharmacokinetic Analysis of a Long-Acting Recombinant Factor VIII-Fc Fusion Protein (rFVIIIFc) in Patients with Severe Hemophilia A By characterizing the population PK of long-acting FVIII-Fc (rFVIIIFc) in patients with severe hemophilia A, a model of estimated population PK parameters of rFVIIIFc can be established. This model may assist physicians who wish to tailor dosing for individual patients with sparse PK samples. This model may also help determine the suitability of rFVIIIFc for a fixed dosing regimen.

Objectives: To characterize the activity-time profiles of rFVIIIFc in hemophilia A patients by population PK analysis and to identify intrinsic covariates that may affect the variability of rFVIIIFc PK.

The modeling dataset included activity-time profiles of 180 subjects (15 from a Phase 1/2a study and 165 from a Phase 3 study [A-LONG], collected over ≤52 weeks of treatment). Subjects were 12 to 65 years old and weighed 41-132 kg. The analysis was done with NONMEM 7 software, and included model building, covariate search, and model qualification steps.

A 2-compartmental model adequately described the activity of rFVIIIFc. The population estimate for clearance (CL)=1.65 dL/h; volume of distribution at steady state (Vss)=44.4 dL. The inter-individual variability (IIV) of CL was moderate (24.3%) and central volume of distribution (V1) was low (13.4%). The inter-occasional variability (IOV) of both CL and V1 was low (20.6 and 12.0% respectively). The additive residual error was very low (0.208 IU/dL), as was the proportional residual error (13.6%), approximating the variability of the one-stage clotting assay for FVIII activity. Von Willebrand Factor (VWF) level was identified as the major covariate for CL; higher levels of VWF yielded lower clearance values, reflecting the protective role that VWF has on FVIII activity. Body Weight (BW) and Haematocrit (HCT) were identified as weak covariates on V1.

This is the first population PK analysis that systematically describes and characterizes the prolonged activity profile of long-acting rFVIIIFc. The population PK model of rFVIII activity adequately describes the observed activity-time profiles. The clearance of rFVIIIFc activity is lower than the clearance observed for ADVATE®, resulting in longer duration of activity. The low IIV underlines the consistency and homogeneity of the activity profiles. The low IOV indicates that rFVIIIFc maintains stable and predictable activity with long term administration over time. The set of covariates identified is physiologically relevant. Therefore, the population model developed can be used to simulate various dosing scenarios in support of dosing regimen selection and other decision making related to rFVIIIFc therapy. This approach represents an advance over the current utilitarian approach, wherein a regimen is not determined to be ineffective until after a patient has a bleeding episode.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are incorporated by reference herein in their entirety.

TABLES

TABLE 4

Polynucleotide Sequences: FIX-Fc

A. FIX-Fc Chain DNA Sequence (SEQ ID NO: 1, which encodes SEQ ID NO: 2)
pSYN-FIX-030 Nucleotide sequence (nt 1 to 7583):
FIX exon 1 (signal peptide, 1st amino acid propeptide): nt 690-777
FIX mini intron: nt 778-1076
FIX propeptide sequence: nt 1077-1126
Mature FIX sequence: nt 1127-2371
Fc: nt 2372-3052

```
gcgcgcgttgacattgattattgactagttattaatagtaatcaattacggggtcattagttcatagcccatata tggagttccgcgttacataacttacggtaaatggcccgcctggctgaccgcccaacgaccccgcccattgacgt caataatgacgtatgttcccatagtaacgccaatagggactttccattgacgtcaatgggtggagtatttacggt aaactgcccacttggcagtacatcaagtgtatcatatgccaagtacgccccctattgacgtcaatgacggtaaat ggcccgcctggcattatgcccagtacatgaccttatgggactttcctacttggcagtacatctacgtattagtca tcgctattaccatggtgatgcggttttggcagtacatcaatgggcgtggatagcggtttgactcacggggatttc caagtctccacccattgacgtcaatgggagtttgttttggcaccaaaatcaacgggactttccaaaatgtcgta acaactccgccccattgacgcaaatgggcggtaggcgtgtacggtgggaggtctatataagcagagctctctggc taactagagaacccactgcttactggcttatcgaaattaatacgactcactatagggagacccaagcttcgcgac gtacgccgccaccatgcagcgcgtgaacatgatcatggcagaatcaccaggcctcatcaccatctgcctttag gatatctactcagtgctgaatgtacaggtttgtttccttttttaaaatacattgagtatgcttgccttttagata tagaaatatctgatgctgtcttcttcactaaattttgattacatgatttgacagcaatattgaagagtctaacag ccagcacgcaggttggtaagtactgtgggaacatcacagattttggctccatgccctaaagagaaattggctttc agattatttggattaaaaacaaagactttcttaagagatgtaaaattttcatgatgttttcttttttgctaaaac taaagaattattcttttacatttcagttttcttgatcatgaaaacgccaacaaaattctgaatcggccaaagag gtataattcaggtaaattggaagagtttgttcaagggaatctagagagagaatgtatggaagaaaagtgtagttt tgaagaagcacgagaagttttgaaaacactgaaagaacaactgaattttggaagcagtatgttgatggagatca gtgtgagtccaatccatgtttaaatggcggcagttgcaaggatgacattaattcctatgaatgttggtgtccctt tggatttgaaggaaagaactgtgaattagatgtaacatgtaacattaagaatggcagatgcgagcagttttgtaa aaatagtgctgataacaaggtggtttgctcctgtactgagggatatcgacttgcagaaaaccagaagtcctgtga accagcagtgccatttccatgtggaagagtttctgtttcacaaacttctaagctcacccgtgctgagactgtttt
```

TABLE 4-continued

Polynucleotide Sequences: FIX-Fc tcctgatgtggactatgtaaattctactgaagctgaaaccattttggataacatcactcaaagcacccaatcatt taatgacttcactcgggttgttggtggagaagatgccaaaccaggtcaattcccttggcaggttgttttgaatgg taaagttgatgcattctgtggaggctctatcgttaatgaaaaatggattgtaactgctgcccactgtgttgaaac tggtgttaaaattacagttgtcgcaggtgaacataatattgaggagacagaacatacagagcaaaagcgaaatgt gattcgaattattcctcaccacaactacaatgcagctattaataagtacaaccatgacattgcccttctggaact ggacgaaccccttagtgctaaacagctacgttacacctatttgcattgctgacaaggaatacacgaacatcttcct caaatttggatctggctatgtaagtggctggggaagagtcttccacaaagggagatcagctttagttcttcagta ccttagagttccacttgttgaccgagccacatgtcttcgatctacaaagttcaccatctataacaacatgttctg tgctggcttccatgaaggaggtagagattcatgtcaaggagatagtgggggaccccatgttactgaagtggaagg gaccagtttcttaactggaattattagctggggtgaagagtgtgcaatgaaaggcaaatatggaatatataccaa ggtgtcccggtatgtcaactggattaaggaaaaaacaaagctcactgacaaaactcacacatgcccaccgtgccc agctccggaactcctgggcggaccgtcagtcttcctcttccccccaaaacccaaggacaccctcatgatctcccg gacccctgaggtcacatgcgtggtggtggacgtgagccacgaagaccctgaggtcaagttcaactggtacgtgga cggcgtggaggtgcataatgccaagacaaagccgcgggaggagcagtacaacagcacgtaccgtgtggtcagcgt cctcaccgtcctgcaccaggactggctgaatggcaaggagtacaagtgcaaggtctccaacaaagccctcccagc ccccatcgagaaaaccatctccaaagccaaagggcagccccgagaaccacaggtgtacaccctgcccccatcccg ggatgagctgaccaagaaccaggtcagcctgacctgcctggtcaaaggcttctatcccagcgacatcgccgtgga gtgggagagcaatgggcagccggagaacaactacaagaccacgcctcccgtgttggactccgacggctccttctt cctctacagcaagctcaccgtggacaagagcaggtggcagcaggggaacgtcttctcatgctccgtgatgcatga ggctctgcacaaccactacacgcagaagagcctctccctgtctccgggtaaatgagaattcagacatgataagat acattgatgagtttggacaaaccacaactagaatgcagtgaaaaaaatgctttatttgtgaaatttgtgatgcta ttgctttatttgtaaccattataagctgcaataaacaagttggggtgggcgaagaactccagcatgagatccccg cgctggaggatcatccagccggcgtcccggaaaacgattccgaagcccaaccctttcatagaaggcggcggtggaa tcgaaatctcgtagcacgtgtcagtcctgctcctcggccacgaagtgcacgcagttgccggccgggtcgcgcagg gcgaactcccgcccccacggctgctcgccgatctcggtcatggccgcccggaggcgtcccggaagttcgtggac acgacctccgaccactcggcgtacagctcgtccaggccgcgcacccacacccaggccagggtgttgtccggcacc acctggtcctggaccgcgctgatgaacagggtcacgtcgtcccggaccacaccggcgaagtcgtcctccacgaag tcccgggagaacccgagccggtcggtccagaactcgaccgctccggcgacgtcgcgcgcggtgagcaccggaacg gcactggtcaacttggccatggtttagttcctcaccttgtcgtattatactatgccgatatactatgccgatgat taattgtcaacacgtgctgatcagatccgaaaatggatatacaagctcccgggagcttttgcaaaagcctaggc ctccaaaaaagcctcctcactacttctggaatagctcagaggcagaggcggcctcggcctctgcataaataaaaa aaattagtcagccatggggcggagaatgggcggaactgggcggagttaggggcgggatgggcggagttaggggcg ggactatggttgctgactaattgagatgcatgctttgcatacttctgcctgctggggagcctggggactttccac acctggttgctgactaattgagatgcatgctttgcatacttctgcctgctggggagcctggggactttccacacc ctcgtcgagctagcttcgtgaggctccggtgcccgtcagtgggcagagcgcacatcgcccacagtccccgagaag ttgggggaggggtcggcaattgaaccggtgcctagagaaggtggcgcggggtaaactgggaaagtgatgtcgtg tactggctccgcctttttcccgagggtgggggagaaccgtatataagtgcagtagtcgccgtgaacgttcttttt cgcaacgggtttgccgccagaacacaggtaagtgccgtgtgtggttcccgcgggcctggcctctttacgggttat ggcccttgcgtgccttgaattacttccacctggctccagtacgtgattcttgatcccgagctggagccaggggcg TABLE 4-continued Polynucleotide Sequences: FIX-Fc ggccttgcgctttaggagccccttcgcctcgtgcttgagttgaggcctggcctgggcgctggggccgccgcgtgc gaatctggtggcaccttcgcgcctgtctcgctgctttcgataagtctctagccatttaaaattttttgatgacctg ctgcgacgcttttttttctggcaagatagtcttgtaaatgcgggccaggatctgcacactggtatttcggttttttg gggccgcgggcggcgacgggccccgtgcgtcccagcgcacatgttcggcgaggcggggcctgcgagcgcggccac cgagaatcggacggggggtagtctcaagctggccggcctgctctggtgcctggcctcgcgccgccgtgtatcgccc cgccctgggcggcaaggctggcccggtcggcaccagttgcgtgagcggaaagatggccgcttcccggccctgctc cagggggctcaaaatggaggacgcggcgctcgggagagcgggcgggtgagtcacccacacaaaggaaaggggcct ttccgtcctcagccgtcgcttcatgtgactccacggagtaccgggcgccgtccaggcacctcgattagttctgga gcttttggagtacgtcgtctttaggttgggggaggggttttatgcgatggagtttccccacactgagtgggtgg agactgaagttaggccagcttggcacttgatgtaattctccttggaacttgccctttttgagtttggatcttggt tcattctcaagcctcagacagtggttcaaagttttttttcttccatttcaggtgtcgtgaacacgtggtcgcggcc gcgccgccaccatggagacagacacactcctgctatgggtactgctgctccgggttccaggttccactggtgaca aaactcacacatgcccaccgtgcccagcacctgaactcctgggaggaccgtcagtcttcctcttcccccaaaac ccaaggacaccctcatgatctcccggacccctgaggtcacatgcgtggtggtggacgtgagccacgaagaccctg aggtcaagttcaactggtacgtggacggcgtggaggtgcataatgccaagacaaagccgcgggaggagcagtaca acagcacgtaccgtgtggtcagcgtcctcaccgtcctgcaccaggactggctgaatggcaaggagtacaagtgca aggtctccaacaaagccctcccagcccccatcgagaaaaccatctctccaaagccaaagggcagccccgagaaccac aggtgtacaccctgcccccatcccgcgatgagctgaccaagaaccaggtcagcctgacccgcctggtcaaaggct tctatcccagcgacatcgccgtggagtgggagagcaatgggcagccggagaacaactacaagaccacgcctcccg tgttggactccgacggctccttcttcctctacagcaagctcaccgtggacaagagcaggtggcagcaggggaacg tcttctcatgctccgtgatgcatgaggctctgcacaaccactacacgcagaagagcctctccctgtctccgggta aatgactcgagagatctggccggctgggcccgtttcgaaggtaagcctatccctaaccctctcctcggtctcgat tctacgcgtaccggCcatcaccaccatcaccattgagtttaaacccgctgatcagcctcgactgtgccttctagt tgccagccatctgttgtttgcccctcccccgtgccttccttgaccctggaaggtgccactcccactgtcctttcc taataaaatgaggaaattgcatcgcattgtctgagtaggtgtcattctattctggggggtggggtggggcaggac agcaaggggaggattgggaagacaatagcaggcatgctggggatgcggtgggctctatggcttctgaggcggaa agaaccagtggcggtaatacggttatccacagaatcaggggataacgcaggaaagaacatgtgagcaaaaggcca gcaaaaggccaggaaccgtaaaaaggccgcgttgctggcgtttttccataggctccgcccccctgacgagcatca caaaaatcgacgctcaagtcagaggtggcgaaacccgacaggactataaagataccaggcgtttccccctagaag ctccctcgtgcgctctcctgttccgaccctgccgcttaccggatacctgtccgcctttctcccttcgggaagcgt ggcgctttctcatagctcacgctgtaggtatctcagttcggtgtaggtcgttcgctccaagctgggctgtgtgca cgaaccccccgttcagcccgaccgctgcgccttatccggtaactatcgtcttgagtccaacccggtaagacacga cttatcgccactggcagcagccactggtaacaggattagcagagcgaggtatgtaggcggtgctacagagttctt gaagtggtggcctaactacggctacactagaagaacagtatttggtatctgcgctctgctgaagccagttacctt cggaaaaagagttggtagctcttgatccggcaaacaaaccaccgctggtagcggtggtttttttgtttgcaagca gcagattacgcgcagaaaaaaaggatctcaagaagatcctttgatcttttctacggggtctgacgctcagtggaa cgaaaactcacgttaagggattttggtcatgacattaacctataaaaataggcgtatcacgaggccctttcgtct cgcgcgtttcggtgatgacggtgaaaacctctgacacatgcagctcccggagacggtcacagcttgtctgtaagc ggatgccgggagcagacaagcccgtcagggcgcgtcagcgggtgttggcgggtgtcggggctggcttaactatgc TABLE 4-continued Polynucleotide Sequences: FIX-Fc ggcatcagagcagattgtactgagagtgcaccatatatgcggtgtgaaataccgcacagatgcgtaaggagaaaa taccgcatcaggcgccattcgccattcaggctgcgcaactgttgggaagggcgatcggtgcgggcctcttcgcta ttacgcca B. Fc DNA sequence (mouse IgK signal peptide underlined) (SEQ ID NO: 3), which encodes SEQ ID NO: 4) This is the Fc cassette from pSYN-FIX-030. In addidtion, there is a separate Fc expression cassette that was transfected into the cell line in plasmid pSYN-Fc-015 that encodes the same amino acid sequence, but contains a few noncoding changes. The second copy of Fc encoding sequence enables a better monomer: dimer ratio.
<u>atggagacagacacactcctgctatgggtactgctgctctgggttccaggttccactggt</u>gacaaaactcacaca tgcccaccgtgcccagcacctgaactcctgggaggaccgtcagtcttcctcttccccccaaaacccaaggacacc ctcatgatctcccggacccctgaggtcacatgcgtggtggtggacgtgagccacgaagaccctgaggtcaagttc aactggtacgtggacggcgtggaggtgcataatgccaagacaaagccgcgggaggagcagtacaacagcacgtac cgtgtggtcagcgtcctcaccgtcctgcaccaggactggctgaatggcaaggagtacaagtgcaaggtctccaac aaagccctcccagcccccatcgagaaaaccatctccaaagccaaagggcagccccgagaaccacaggtgtacacc ctgcccccatcccgcgatgagctgaccaagaaccaggtcagcctgacctgcctggtcaaaggcttctatcccagc gacatcgccgtggagtgggagagcaatgggcagccggagaacaactacaagaccacgcctcccgtgttggactcc gacggctccttcttcctctacagcaagctcaccgtggacaagagcaggtggcagcaggggaacgtcttctcatgc tccgtgatgcatgaggctctgcacaaccactacacgcagaagagcctctccctgtctccgggtaaa

TABLE 5

Polypeptide Sequences: FIX-Fc
FIX-Fc Monomer Hybrid: created by
coexpressing FIX-Fc and Fc chains.

A. FIX-Fc chain (SEQ ID NO: 2):
(28 amino acid signal sequence underlined, 18 amino acid propeptide double underlined, Fc portion in italics.) The C-terminal lysine is not present in either subunit; this processing is often observed in recombinant proteins produced in mammalian cell culture, as well as with plasma derived proteins.
FIXFC-SC SUBUNIT:
FIX SignalPeptide: -46 <u>MQRVNMIMAE SPGLITICLL GYLLSAEC</u>

FIX Propeptide: -18 <u>TVFLDHENAN KILNUKR</u>

```
  1  YNSGKLEEFV QGNLERECME EKCSFEEARE VFENTERTTE FWKQYVDGDQ

51  CESNPCLNGG SCKDDINSYE CWCPFGFEGK NCELDVTCNI KNGRCEQFCK

101  NSADNKVVCS CTEGYRLAEN QKSCEPAVPF PCGRVSVSQT SKLTRAETVF

151  PDVDYVNSTE AETILDNITQ STQSFNDFTR VVGGEDAKPG QFPWQVVLNG

201  KVDAFCGGSI VNEKWIVTAA HCVETGVKIT VVAGEHNIEE TEHTEQKRNV

251  IRIIPHHNYN AAINKYNHDI ALLELDEPLV LNSYVTPICI ADKEYTNIFL

301  KFGSGYVSGW GRVFRRGR6A LVLQYLRVPL VDRATCLRST KFTIYNNMFC

351  AGFHEGGRDS CQGDSGGPHV TEVEGTSFLT GIISWGEECA MKGKYGIYTK

401  VSRYVNWIKE KTKL*TDKTHT CPPCPAPELL GGPSVFLFPP KPKDTLMISR*

451  *TPEVTCVVVD VSHEDPEVKF NWYVDGVEVH NAKTKPREEQ YNSTYRVVSV*

501  *LTV1HQDWIN GKEYKCKVSN KALPAPIEKT ISKAKGQPRE PQVYTLPPSR*

551  *LELTENQVSL TCLVKGFYPS DIAVEWESNG QPENNYKTTP PVLDSDGSFF*
```

TABLE 5-continued

Polypeptide Sequences: FIX-Fc
FIX-Fc Monomer Hybrid: created by
coexpressing FIX-Fc and Fc chains.

601 *LYSKLTVDKS RWQQGNVFSC SVMHEALHNH YTQKSLSLSP GK*

B. Fc chain (SEQ ID NO: 4)
20 amino acid heterologous mouse Igκ light chain signal
peptide (underlined): -20 <u>METDTLLLWV LLLWVPGSTG</u>

Mature Fc sequence (corresponding to human IgG1 amino acids
221 to 447, EU numbering)
```
  1  DKTHTCPPCP APELLGGPSV FLFPPKPKDT LMISRTPEVT CVVVDVSHED

51  PEVKFNWYVD GVEVENAKTK PREEQYNSTY RVVSVLTVLH QDWLNGKEYK

101  CKVSNKALPA PIEKTISKAK GQPREPQVYT LPPSRDELTK NQVSLTCLVK

151  GFYPSDIAVE WESNGQPENN YKTTPPVLDS DGSFFLYSKL TVDKSRWQQG

201  NVFSCSVMHE ALHNHYTQKS LSLSPGK
```

TABLE 6

Polynucleotide Sequence: FVIII-Fc

A. B-Domain Deleted FVIIIFc
(i) B-Domain Deleted FVIIIFc Chain DNA Sequence (FVIII signal peptide
underlined. Fc region in bold) (SEQ ID NO: 5, which encodes
SEQ ID NO: 6)
```
 661                             A TGCAAATAGA GCTCTCCACC TGCTTCTTTC

721  TGTGCCTTTT GCGATTCTGC TTTAGTGCCA CCAGAAGATA CTACCTGGGT GCAGTGGAAC

781  TGTCATGGGA CTATATGCAA AGTGATCTCG GTGAGCTGCC TGTGGACGCA AGATTTCCTC

841  CTAGAGTGCC AAAATCTTTT CCATTCAACA CCTCAGTCGT GTACAAAAAG ACTCTGTTTG

901  TAGAATTCAC GGATCACCTT TTCAACATCG CTAAGCCAAG GCCACCCTGG ATGGGTCTGC

961  TAGGTCCTAC CATCCAGGCT GAGGTTTATG ATACAGTGGT CATTACACTT AAGAACATGG

1021  CTTCCCATCC TGTCAGTCTT CATGCTGTTG GTGTATCCTA CTGGAAAGCT TCTGAGGGAG

1081  CTGAATATGT TGATCAGACC AGTCAAAGGG AGAAAGAAGA TGATAAAGTC TTCCCTGGTG

1141  GAAGCCATAC ATATGTCTGG CAGGTCCTGA AAGAGAATGG TCCAATGGCC TCTGACCCAC

1201  TGTGCCTTAC CTACTCATAT CTTTCTCATG TGGACCTGGT AAAAGACTTG AATTCAGGCC

1261  TCATTGGAGC CCTACTAGTA TGTAGAGAAG GGAGTCTGGC CAAGGAAAAG ACACAGACCT

1321  TGCACAAATT TATACTACTT TTTGCTGTAT TTGATGAAGG GAAAAGTTGG CACTCAGAAA

1381  CAAAGAACTC CTTGATGCAG GATAGGGATG CTGCATCTGC TCGGGCCTGG CCTAAAATGC

1441  ACACAGTCAA TGGTTATGTA AACAGGTCTC TGCCAGGTCT GATTGGATGC CACAGGAAAT

1501  CAGTCTATTG GCATGTGATT GGAATGGGCA CCACTCCTGA AGTGCACTCA ATATTCCTCG

1561  AAGGTCACAC ATTTCTTGTG AGGAACCATC GCCAGGCGTC CTTGGAAATC TCGCCAATAA

1621  CTTTCCTTAC TGCTCAAACA CTCTTGATGG ACCTTGGACA GTTTCTACTG TTTTGTCATA

1681  TCTCTTCCCA CCAACATGAT GGCATGGAAG CTTATGTCAA AGTAGACAGC TGTCCAGAGG

1741  AACCCCAACT ACGAATGAAA AATAATGAAG AAGCGGAAGA CTATGATGAT GATCTTACTG

1801  ATTCTGAAAT GGATGTGGTC AGGTTTGATG ATGACAACTC TCCTTCCTTT ATCCAAATTC

1861  GCTCAGTTGC CAAGAAGCAT CCTAAAACTT GGGTACATTA CATTGCTGCT GAAGAGGAGG

1921  ACTGGGACTA TGCTCCCTTA GTCCTCGCCC CCGATGACAG AAGTTATAAA AGTCAATATT

1981  TGAACAATGG CCCTCAGCGG ATTGGTAGGA AGTACAAAAA AGTCCGATTT ATGGCATACA

2041  CAGATGAAAC CTTTAAGACT CGTGAAGCTA TTCAGCATGA ATCAGGAATC TTGGGACCTT
```

TABLE 6-continued

Polynucleotide Sequence: FVIII-Fc

```
2101  TACTTTATGG GGAAGTTGGA GACACACTGT TGATTATATT TAAGAATCAA GCAAGCAGAC
2161  CATATAACAT CTACCCTCAC GGAATCACTG ATGTCCGTCC TTTGTATTCA AGGAGATTAC
2221  CAAAAGGTGT AAACATTTG AAGGATTTTC CAATTCTGCC AGGAGAAATA TTCAAATATA
2281  AATGGACAGT GACTGTAGAA GATGGGCCAA CTAAATCAGA TCCTCGGTGC CTGACCCGCT
2341  ATTACTCTAG TTTCGTTAAT ATGGAGAGAG ATCTAGCTTC AGGACTCATT GGCCCTCTCC
2401  TCATCTGCTA CAAAGAATCT GTAGATCAAA GAGGAAACCA GATAATGTCA GACAAGAGGA
2461  ATGTCATCCT GTTTTCTGTA TTTGATGAGA ACCGAAGCTG GTACCTCACA GAGAATATAC
2521  AACGCTTTCT CCCCAATCCA GCTGGAGTGC AGCTTGAGGA TCCAGAGTTC CAAGCCTCCA
2581  ACATCATGCA CAGCATCAAT GGCTATGTTT TTGATAGTTT GCAGTTGTCA GTTTGTTTGC
2641  ATGAGGTGGC ATACTGGTAC ATTCTAAGCA TTGGAGCACA GACTGACTTC CTTTCTGTCT
2701  TCTTCTCTGG ATATACCTTC AAACACAAAA TGGTCTATGA AGACACACTC ACCCTATTCC
2761  CATTCTCAGG AGAAACTGTC TTCATGTCGA TGGAAAACCC AGGTCTATGG ATTCTGGGGT
2821  GCCACAACTC AGACTTTCGG AACAGAGGCA TGACCGCCTT ACTGAAGGTT TCTAGTTGTG
2881  ACAAGAACAC TGGTGATTAT TACGAGGACA GTTATGAAGA TATTTCAGCA TACTTGCTGA
2941  GTAAAAACAA TGCCATTGAA CCAAGAAGCT TCTCTCAAAA CCCACCAGTC TTGAAACGCC
3001  ATCAACGGGA ATAACTCGT ACTACTCTTC AGTCAGATCA AGAGGAAATT GACTATGATG
3061  ATACCATATC AGTTGAAATG AAGAAGGAAG ATTTTGACAT TTATGATGAG GATGAAAATC
3121  AGAGCCCCCG CAGCTTTCAA AAGAAAACAC GACACTATTT TATTGCTGCA GTGGAGAGGC
3181  TCTGGGATTA TGGGATGAGT AGCTCCCCAC ATGTTCTAAG AAACAGGGCT CAGAGTGGCA
3241  GTGTCCCTCA GTTCAAGAAA GTTGTTTTCC AGGAATTTAC TGATGGCTCC TTTACTCAGC
3301  CCTTATACCG TGGAGAACTA AATGAACATT TGGGACTCCT GGGGCCATAT ATAAGAGCAG
3361  AAGTTGAAGA TAATATCATG GTAACTTTCA GAAATCAGGC CTCTCGTCCC TATTCCTTCT
3421  ATTCTAGCCT TATTTCTTAT GAGGAAGATC AGAGGCAAGG AGCAGAACCT AGAAAAAACT
3481  TTGTCAAGCC TAATGAAACC AAAACTTACT TTTGGAAAGT GCAACATCAT ATGGCACCCA
3541  CTAAAGATGA GTTTGACTGC AAAGCCTGGG CTTATTTCTC TGATGTTGAC CTGGAAAAAG
3601  ATGTGCACTC AGGCCTGATT GGACCCCTTC TGGTCTGCCA CACTAACACA CTGAACCCTG
3661  CTCATGGGAG ACAAGTGACA GTACAGGAAT TTGCTCTGTT TTTCACCATC TTTGATGAGA
3721  CCAAAAGCTG GTACTTCACT GAAAATATGG AAAGAAACTG CAGGGCTCCC TGCAATATCC
3781  AGATGGAAGA TCCCACTTTT AAAGAGAATT ATCGCTTCCA TGCAATCAAT GGCTACATAA
3841  TGGATACACT ACCTGGCTTA GTAATGGCTC AGGATCAAAG GATTCGATGG TATCTGCTCA
3901  GCATGGGCAG CAATGAAAAC ATCCATTCTA TTCATTTCAG TGGACATGTG TTCACTGTAC
3961  GAAAAAAAGA GGAGTATAAA ATGGCACTGT ACAATCTCTA TCCAGGTGTT TTTGAGACAG
4021  TGGAAATGTT ACCATCCAAA GCTGGAATTT GGCGGGTGGA ATGCCTTATT GGCGAGCATC
4081  TACATGCTGG GATGAGCACA CTTTTTCTGG TGTACAGCAA TAAGTGTCAG ACTCCCCTGG
4141  GAATGGCTTC TGGACACATT AGAGATTTTC AGATTACAGC TTCAGGACAA TATGGACAGT
4201  GGGCCCCAAA GCTGGCCAGA CTTCATTATT CCGGATCAAT CAATGCCTGG AGCACCAAGG
4261  AGCCCTTTTC TTGGATCAAG GTGGATCTGT TGGCACCAAT GATTATTCAC GGCATCAAGA
4321  CCCAGGGTGC CCGTCAGAAG TTCTCCAGCC TCTACATCTC TCAGTTTATC ATCATGTATA
4381  GTCTTGATGG GAAGAAGTGG CAGACTTATC GAGGAAATTC CACTGGAACC TTAATGGTCT
```

TABLE 6-continued

Polynucleotide Sequence: FVIII-Fc

```
4441 TCTTTGGCAA TGTGGATTCA TCTGGGATAA AACACAATAT TTTTAACCCT CCAATTATTG

4501 CTCGATACAT CCGTTTGCAC CCAACTCATT ATAGCATTCG CAGCACTCTT CGCATGGAGT

4561 TGATGGGCTG TGATTTAAAT AGTTGCAGCA TGCCATTGGG AATGGAGAGT AAAGCAATAT

4621 CAGATGCACA GATTACTGCT TCATCCTACT TTACCAATAT GTTTGCCACC TGGTCTCCTT

4681 CAAAAGCTCG ACTTCACCTC CAAGGGAGGA GTAATGCCTG AGACCTCAG GTGAATAATC

4741 CAAAAGAGTG GCTGCAAGTG GACTTCCAGA AGACAATGAA AGTCACAGGA GTAACTACTC

4801 AGGGAGTAAA ATCTCTGCTT ACCAGCATGT ATGTGAAGGA GTTCCTCATC TCCAGCAGTC

4861 AAGATGGCCA TCAGTGGACT CTCTTTTTTC AGAATGGCAA AGTAAAGGTT TTTCAGGGAA

4921 ATCAAGACTC CTTCACACCT GTGGTGAACT CTCTAGACCC ACCGTTACTG ACTCGCTACC

4981 TTCGAATTCA CCCCCAGAGT TGGGTGCACC AGATTGCCCT GAGGATGGGA GTTCTGGGCT

5041 GCGAGGCACA GGACCTCTAC GACAAAACTC ACACATGCCC ACCGTGCCCA GCTCCAGAAC

5101 TCCTGGGCGG ACCGTCAGTC TTCCTCTTCC CCCCAAAACC CAAGGACACC CTCATGATCT

5161 CCCGGACCCC TGAGGTCACA TGCCTGGTGG TGGACCTGAG CCACGAAGAC CCTGAGGTCA

5221 AGTTCAACTG GTACGTGGAC GGCGTGGAGG TCCATAATGC CAAGACAAAG CCGCGGGAGG

5281 AGCAGTACAA CAGCACGTAC CGTGTGGTCA GCGTCCTCAC CGTCCTGCAC CACCACTGGC

5341 TGAATGGCAA GGAGTACAAG TGCAAGGTCT CCAACAAAGC CCTCCCAGCC CCCATCGAGA

5401 AAACCATCTC CAAAGCCAAA GGGCAGCCCC GAGAACCACA GGTGTACACC CTGCCCCCAT

5461 CCCGGGATGA GCTGACCAAG AACCAGGTCA GCCTGACCTG CCTGGTCAAA GGCTTCTATC

5521 CCAGCGACAT CGCCGTGGAG TGGGAGAGCA ATGGGCAGCC GGAGAACAAC TACAAGACCA

5581 CGCCTCCCGT GTTGGACTCC GACGGCTCCT TCTTCCTCTA CAGCAAGCTC ACCGTGGACA

5641 AGAGCAGGTG GCAGCAGGGG AACGTCTTCT CATGCTCCGT GATGCATGAG GCTCTGCACA

5701 ACCACTACAC GCAGAAGACC CTCTCCCTGT CTCCGGGTAA A
```

(ii) Fc DNA sequence mouse Igκ signal peptide underlined)
(SEQ ID NO: 3, which encodes SEQ ID NO: 4)

```
7981                                                  ATGGA GACAGACACA

8041 CTCCTGCTAT GGGTACTGCT GCTCTGGGTT CCAGGTTCCA CTGGTGACAA AACTCACACA

8101 TGCCCACCGT GCCCAGCACC TGAACTCCTG GGAGGACCGT CAGTCTTCCT CTTCCCCCCA

8161 AAACCCAAGG ACACCCTCAT GATCTCCCGG ACCCCTGAGG TCACATGCGT GGTGGTGGAC

8221 GTGAGCCACG AAGACCCTGA GGTCAAGTTC AACTGGTACG TGGACGGCGT GGAGGTGCAT

8281 AATGCCAAGA CAAAGCCGCG GGAGGAGCAG TACAACAGCA CGTACCGTGT GGTCAGCGTC

8341 CTCACCGTCC TGCACCAGGA CTGGCTGAAT GGCAAGGAGT ACAAGTGCAA GGTCTCCAAC

8401 AAAGCCCTCC CAGCCCCCAT CGAGAAAACC ATCTCCAAAG CCAAAGGGCA GCCCCGAGAA

8461 CCACAGGTGT ACACCCTGCC CCCATCCCGC GATGAGCTGA CCAAGAACCA GGTCAGCCTG

8521 ACCTGCCTGG TCAAAGGCTT CTATCCCAGC GACATCGCCG TGGAGTGGGA GAGCAATGGG

8581 CAGCCGGAGA ACAACTACAA GACCACGCCT CCCGTGTTGG ACTCCGACGG CTCCTTCTTC

8641 CTCTACAGCA AGCTCACCGT GGACAAGAGC AGGTGGCAGC AGGGGAACGT CTTCTCATGC

8701 TCCGTGATGC ATGAGGCTCT GCACAACCAC TACACGCAGA AGAGCCTCTC CCTGTCTCCG

8761 GGTAAA
```

TABLE 6-continued

| Polynucleotide Sequence: FVIII-Fc |
|---|

B. Full-length FVIIIFc
(i) Full-length FVIIIFc DNA Sequence (FVIII signal peptide underlined,
Fc region in bold) (SEQ ID NO: 7, which encodes SEQ ID NO: 8)

```
 661                                             ATG CAAATAGAGC TCTCCACCTG
 721 CTTCTTTCTG TGCCTTTTGC GATTCTGCTT TAGTGCCACC AGAAGATACT ACCTGGGTGC
 781 AGTGGAACTG TCATGGGACT ATATGCAAAG TGATCTCGGT GAGCTGCCTG TGGACGCAAG
 841 ATTTCCTCCT AGAGTGCCAA ATCTTTTCC ATTCAACACC TCAGTCGTGT ACAAAAAGAC
 901 TCTGTTTGTA GAATTCACGG ATCACCTTTT CAACATCGCT AAGCCAAGGC CACCCTGGAT
 961 GGGTCTGCTA GGTCCTACCA TCCAGGCTGA GGTTTATGAT ACAGTGGTCA TTACACTTAA
1021 GAACATGGCT TCCCATCCTG TCAGTCTTCA TGCTGTTGGT GTATCCTACT GGAAAGCTTC
1081 TGAGGGAGCT GAATATGATG ATCAGACCAG TCAAAGGGAG AAGAAGATG ATAAAGTCTT
1141 CCCTGGTGGA AGCCATACAT ATGTCTGGCA GGTCCTGAAA GAGAATGGTC CAATGGCCTC
1201 TGACCCACTG TGCCTTACCT ACTCATATCT TTCTCATGTG GACCTGGTAA AGACTTGAA
1261 TTCAGGCCTC ATTGGAGCCC TACTAGTATG TAGAGAAGGG AGTCTGGCCA AGGAAAAGAC
1321 ACAGACCTTG CACAAATTTA TACTACTTTT TGCTGTATTT GATGAAGGGA AAGTTGGCA
1381 CTCAGAAACA AAGAACTCCT TGATGCAGGA TAGGGATGCT GCATCTGCTC GGGCCTGGCC
1441 TAAAATGCAC ACAGTCAATG GTTATGTAAA CAGGTCTCTG CCAGGTCTGA TTGGATGCCA
1501 CAGGAAATCA GTCTATTGGC ATGTGATTGG AATGGGCACC ACTCCTGAAG TGCACTCAAT
1561 ATTCCTCGAA GGTCACACAT TTCTTGTGAG GAACCATCGC CAGGCGTCCT TGGAAATCTC
1621 GCCAATAACT TTCCTTACTG CTCAAACACT CTTGATGGAC CTTGGACAGT TTCTACTGTT
1681 TTGTCATATC TCTTCCCACC AACATGATGG CATGGAAGCT TATGTCAAAG TAGACAGCTG
1741 TCCAGAGGAA CCCCAACTAC GAATGAAAA TAATGAAGAA GCGGAAGACT ATGATGATGA
1801 TCTTACTGAT TCTGAAATGG ATGTGGTCAG GTTTGATGAT GACAACTCTC CTTCCTTTAT
1861 CCAAATTCGC TCAGTTGCCA AGAAGCATCC TAAAACTTGG GTACATTACA TTGCTGCTGA
1921 AGAGGAGGAC TGGGACTATG CTCCCTTAGT CCTCGCCCCC GATGACAGAA GTTATAAAAG
1981 TCAATATTTG AACAATGGCC CTCAGCGGAT TGGTAGGAAG TACAAAAAAG TCCGATTTAT
2041 GGCATACACA GATGAAACCT TTAAGACTCG TGAAGCTATT CAGCATGAAT CAGGAATCTT
2101 GGGACCTTTA CTTTATGGGG AAGTTGGAGA CACACTGTTG ATTATATTTA AGAATCAAGC
2161 AAGCAGACCA TATAACATCT ACCCTCACGG AATCACTGAT GTCCGTCCTT TGTATTCAAG
2221 GAGATTACCA AAAGGTGTAA ACATTTGAA GGATTTTCCA ATTCTGCCAG GAGAAATATT
2281 CAAATATAAA TGGACAGTGA CTGTAGAAGA TGGGCCAACT AAATCAGATC CTCGGTGCCT
2341 GACCCGCTAT TACTCTAGTT TCGTTAATAT GGAGAGAGAT CTAGCTTCAG GACTCATTGG
2401 CCCTCTCCTC ATCTGCTACA AAGAATCTGT AGATCAAAGA GGAAACCAGA TAATGTCAGA
2461 CAAGAGGAAT GTCATCCTGT TTTCTGTATT TGATGAGAAC CGAAGCTGGT ACCTCACAGA
2521 GAATATACAA CGCTTTCTCC CCAATCCAGC TGGAGTGCAG CTTGAGGATC CAGAGTTCCA
2581 AGCCTCCAAC ATCATGCACA GCATCAATGG CTATGTTTTT GATAGTTTGC AGTTGTCAGT
2641 TTGTTTGCAT GAGGTGGCAT ACTGGTACAT TCTAAGCATT GGAGCACAGA CTGACTTCCT
2701 TTCTGTCTTC TTCTCTGGAT ATACCTTCAA ACACAAAATG GTCTATGAAG ACACACTCAC
2761 CCTATTCCCA TTCTCAGGAG AAACTGTCTT CATGTCGATG GAAAACCCAG GTCTATGGAT
2821 TCTGGGGTGC CACAACTCAG ACTTTCGGAA CAGAGGCATG ACCGCCTTAC TGAAGGTTTC
```

TABLE 6-continued

| Polynucleotide Sequence: FVIII-Fc |
|---|
| 2881 TAGTTGTGAC AAGAACACTG GTGATTATTA CGAGGACAGT TATGAAGATA TTTCAGCATA |
| 2941 CTTGCTGAGT AAAAACAATG CCATTGAACC AAGAAGCTTC TCCCAGAATT CAAGACACCC |
| 3001 TAGCACTAGG CAAAAGCAAT TTAATGCCAC CACAATTCCA GAAAATGACA TAGAGAAGAC |
| 3061 TGACCCTTGG TTTGCACACA GAACACCTAT GCCTAAAATA CAAAATGTCT CCTCTAGTGA |
| 3121 TTTGTTGATG CTCTTGCGAC AGAGTCCTAC TCCACATGGG CTATCCTTAT CTGATCTCCA |
| 3181 AGAAGCCAAA TATGAGACTT TTTCTGATGA TCCATCACCT GGAGCAATAG ACAGTAATAA |
| 3241 CAGCCTGTCT GAAATGACAC ACTTCAGGCC ACAGCTCCAT CACAGTGGGG ACATGGTATT |
| 3301 TACCCCTGAG TCAGGCCTCC AATTAAGATT AAATGAGAAA CTGGGGACAA CTGCAGCAAC |
| 3361 AGAGTTGAAG AAACTTGATT TCAAAGTTTC TAGTACATCA AATAATCTGA TTTCAACAAT |
| 3421 TCCATCAGAC AATTTGGCAG CAGGTACTGA TAATACAAGT TCCTTAGGAC CCCCAAGTAT |
| 3481 GCCAGTTCAT TATGATAGTC AATTAGATAC CACTCTATTT GGCAAAAAGT CATCTCCCCT |
| 3541 TACTGAGTCT GGTGGACCTC TGAGCTTGAG TGAAGAAAAT AATGATTCAA AGTTGTTAGA |
| 3601 ATCAGGTTTA ATGAATAGCC AAGAAAGTTC ATGGGGAAAA AATGTATCGT CAACAGAGAG |
| 3661 TGGTAGGTTA TTTAAAGGGA AAAGAGCTCA TGGACCTGCT TTGTTGACTA AGATAATGC |
| 3721 CTTATTCAAA GTTAGCATCT CTTTGTTAAA GACAAACAAA ACTTCCAATA ATTCAGCAAC |
| 3781 TAATAGAAAG ACTCACATTG ATGGCCCATC ATTATTAATT GAGAATAGTC CATCAGTCTG |
| 3841 GCAAAATATA TTAGAAAGTG ACACTGAGTT TAAAAAAGTG ACACCTTTGA TTCATGACAG |
| 3901 AATGCTTATG GACAAAAATG CTACAGCTTT GAGGCTAAAT CATATGTCAA ATAAAACTAC |
| 3961 TTCATCAAAA AACATGGAAA TGGTCCAACA GAAAAAAGAG GGCCCCATTC CACCAGATGC |
| 4021 ACAAAATCCA GATATGTCGT TCTTTAAGAT GCTATTCTTG CCAGAATCAG CAAGGTGGAT |
| 4081 ACAAAGGACT CATGGAAAGA ACTCTCTGAA CTCTGGGCAA GGCCCCAGTC CAAAGCAATT |
| 4141 AGTATCCTTA GGACCAGAAA AATCTGTGGA AGGTCAGAAT TTCTTGTCTG AGAAAAACAA |
| 4201 AGTGGTAGTA GGAAAGGGTG AATTTACAAA GGACGTAGGA CTCAAAGAGA TGGTTTTTCC |
| 4261 AAGCAGCAGA AACCTATTTC TTACTAACTT GGATAATTTA CATGAAAATA ATACACACAA |
| 4321 TCAAGAAAAA AAAATTCAGG AAGAAATAGA AAAGAAGGAA ACATTAATCC AAGAGAATGT |
| 4381 AGTTTTGCCT CAGATACATA CAGTGACTGG CACTAAGAAT TTCATGAAGA ACCTTTTCTT |
| 4441 ACTGAGCACT AGGCAAAATG TAGAAGGTTC ATATGACGGG GCATATGCTC CAGTACTTCA |
| 4501 AGATTTTAGG TCATTAAATG ATTCAACAAA TAGAACAAAG AAACACACAG CTCATTTCTC |
| 4561 AAAAAAAGGG GAGGAAGAAA ACTTGGAAGG CTTGGGAAAT CAAACCAAGC AAATTGTAGA |
| 4621 GAAATATGCA TGCACCACAA GGATATCTCC TAATACAAGC CAGCAGAATT TTGTCACGCA |
| 4681 ACGTAGTAAG AGAGCTTTGA ACAATTCAG ACTCCCACTA GAAGAAACAG AACTTGAAAA |
| 4741 AAGGATAATT GTGGATGACA CCTCAACCCA GTGGTCCAAA AACATGAAAC ATTTGACCCC |
| 4801 GAGCACCCTC ACACAGATAG ACTACAATGA GAAGGAGAAA GGGGCCATTA CTCAGTCTCC |
| 4861 CTTATCAGAT TGCCTTACGA GGAGTCATAG CATCCCTCAA GCAAATAGAT CTCCATTACC |
| 4921 CATTGCAAAG GTATCATCAT TTCCATCTAT TAGACCTATA TATCTGACCA GGGTCCTATT |
| 4981 CCAAGACAAC TCTTCTCATC TTCCAGCAGC ATCTTATAGA AAGAAAGATT CTGGGGTCCA |
| 5041 AGAAAGCAGT CATTTCTTAC AAGGAGCCAA AAAAATAAC CTTTCTTTAG CCATTCTAAC |
| 5101 CTTGGAGATG ACTGGTGATC AAAGAGAGGT TGGCTCCCTG GGGACAAGTG CCACAAATTC |
| 5161 AGTCACATAC AAGAAAGTTG AGAACACTGT TCTCCCGAAA CCAGACTTGC CCAAAACATC |

TABLE 6-continued

| Polynucleotide Sequence: FVIII-Fc |
|---|
| 5221 TGGCAAAGTT GAATTGCTTC CAAAAGTTCA CATTTATCAG AAGGACCTAT TCCCTACGGA |
| 5281 AACTAGCAAT GGGTCTCCTG GCCATCTGGA TCTCGTGGAA GGGAGCCTTC TTCAGGGAAC |
| 5341 AGAGGGAGCG ATTAAGTGGA ATGAAGCAAA CAGACCTGGA AAGTTCCCT TTCTGAGAGT |
| 5401 AGCAACAGAA AGCTCTGCAA AGACTCCCTC CAAGCTATTG GATCCTCTTG CTTGGGATAA |
| 5461 CCACTATGGT ACTCAGATAC CAAAAGAAGA GTGGAAATCC AAGAGAAGT CACCAGAAAA |
| 5521 AACAGCTTTT AAGAAAAAGG ATACCATTTT GTCCCTGAAC GCTTGTGAAA GCAATCATGC |
| 5581 AATAGCAGCA ATAAATGAGG GACAAAATAA GCCCGAAATA GAAGTCACCT GGGCAAAGCA |
| 5641 AGGTAGGACT GAAAGGCTGT GCTCTCAAAA CCCACCAGTC TTGAAACGCC ATCAACGGGA |
| 5701 AATAACTCGT ACTACTCTTC AGTCAGATCA AGAGGAAATT GACTATGATG ATACCATATC |
| 5761 AGTTGAAATG AAGAAGGAAG ATTTTGACAT TTATGATGAG GATGAAAATC AGAGCCCCCG |
| 5821 CAGCTTTCAA AAGAAAACAC GACACTATTT TATTGCTGCA GTGGAGAGGC TCTGGGATTA |
| 5881 TGGGATGAGT AGCTCCCCAC ATGTTCTAAG AAACAGGGCT CAGAGTGGCA GTGTCCCTCA |
| 5941 GTTCAAGAAA GTTGTTTTCC AGGAATTTAC TGATGGCTCC TTTACTCAGC CCTTATACCG |
| 6001 TGGAGAACTA AATGAACATT TGGGACTCCT GGGGCCATAT ATAAGAGCAG AAGTTGAAGA |
| 6061 TAATATCATG GTAACTTTCA GAAATCAGGC CTCTCGTCCC TATTCCTTCT ATTCTAGCCT |
| 6121 TATTTCTTAT GAGGAAGATC AGAGGCAAGG AGCAGAACCT AGAAAAAACT TTGTCAAGCC |
| 6181 TAATGAAACC AAAACTTACT TTTGGAAAGT GCAACATCAT ATGGCACCCA CTAAAGATGA |
| 6241 GTTTGACTGC AAAGCCTGGG CTTATTTCTC TGATGTTGAC CTGGAAAAAG ATGTGCACTC |
| 6301 AGGCCTGATT GGACCCCTTC TGGTCTGCCA CACTAACACA CTGAACCCTG CTCATGGGAG |
| 6361 ACAAGTGACA GTACAGGAAT TTGCTCTGTT TTTCACCATC TTTGATGAGA CCAAAAGCTG |
| 6421 GTACTTCACT GAAAATATGG AAAGAAACTG CAGGGCTCCC TGCAATATCC AGATGGAAGA |
| 6481 TCCCACTTTT AAAGAGAATT ATCGCTTCCA TGCAATCAAT GGCTACATAA TGGATACACT |
| 6541 ACCTGGCTTA GTAATGGCTC AGGATCAAAG GATTCGATGG TATCTGCTCA GCATGGGCAG |
| 6601 CAATGAAAAC ATCCATTCTA TTCATTTCAG TGGACATGTG TTCACTGTAC GAAAAAAGA |
| 6661 GGAGTATAAA ATGGCACTGT ACAATCTCTA TCCAGGTGTT TTTGAGACAG TGGAAATGTT |
| 6721 ACCATCCAAA GCTGGAATTT GGCGGGTGGA ATGCCTTATT GGCGAGCATC TACATGCTGG |
| 6781 GATGAGCACA CTTTTTCTGG TGTACAGCAA TAAGTGTCAG ACTCCCCTGG GAATGGCTTC |
| 6841 TGGACACATT AGAGATTTTC AGATTACAGC TTCAGGACAA TATGGACAGT GGGCCCCAAA |
| 6901 GCTGGCCAGA CTTCATTATT CCGGATCAAT CAATGCCTGG AGCACCAAGG AGCCCTTTTC |
| 6961 TTGGATCAAG GTGGATCTGT TGGCACCAAT GATTATTCAC GGCATCAAGA CCCAGGGTGC |
| 7021 CCGTCAGAAG TTCTCCAGCC TCTACATCTC TCAGTTTATC ATCATGTATA GTCTTGATGG |
| 7081 GAAGAAGTGG CAGACTTATC GAGGAAATTC CACTGGAACC TTAATGGTCT TCTTTGGCAA |
| 7141 TGTGGATTCA TCTGGGATAA AACACAATAT TTTTAACCCT CCAATTATTG CTCGATACAT |
| 7201 CCGTTTGCAC CCAACTCATT ATAGCATTCG CAGCACTCTT CGCATGGAGT TGATGGGCTG |
| 7261 TGATTTAAAT AGTTGCAGCA TGCCATTGGG AATGGAGAGT AAAGCAATAT CAGATGCACA |
| 7321 GATTACTGCT TCATCCTACT TTACCAATAT GTTTGCCACC TGGTCTCCTT CAAAAGCTCG |
| 7381 ACTTCACCTC CAAGGGAGGA GTAATGCCTG GAGACCTCAG GTGAATAATC CAAAAGAGTG |
| 7441 GCTGCAAGTG GACTTCCAGA AGACAATGAA AGTCACAGGA GTAACTACTC AGGGAGTAAA |
| 7501 ATCTCTGCTT ACCAGCATGT ATGTGAAGGA GTTCCTCATC TCCAGCAGTC AAGATGGCCA |

TABLE 6-continued

| Polynucleotide Sequence: FVIII-Fc |
|---|
| 7561 TCAGTGGACT CTCTTTTTTC AGAATGGCAA AGTAAAGGTT TTTCAGGGAA ATCAAGACTC |
| 7621 CTTCACACCT GTGGTGAACT CTCTAGACCC ACCGTTACTG ACTCGCTACC TTCGAATTCA |
| 7681 CCCCCAGAGT TGGGTGCACC AGATTGCCCT GAGGATGGAG GTTCTGGGCT GCGAGGCACA |
| 7741 GGACCTCTAC GACAAAACTC ACACATGCCC ACCGTGCCCA GCTCCAGAAC TCCTGGGCGG |
| 7801 ACCGTCAGTC TTCCTCTTCC CCCCAAAACC CAAGGACACC CTCATGATCT CCCGGACCCC |
| 7861 TGAGGTCACA TGCGTGGTGG TGGACGTGAG CCACGAAGAC CCTGAGGTCA AGTTCAACTG |
| 7921 GTACGTGGAC GGCGTGGAGG TGCATAATGC CAAGACAAAG CCGCGGGAGG AGCAGTACAA |
| 7981 CAGCACGTAC CGTGTGGTCA GCGTCCTCAC CGTCCTGCAC CAGGACTGGC TGAATGGCAA |
| 8041 GGAGTACAAG TGCAAGGTCT CCAACAAAGC CCTCCCAGCC CCCATCGAGA AAACCATCTC |
| 8101 CAAAGCCAAA GGGCAGCCCC GAGAACCACA GGTGTACACC CTGCCCCCAT CCCGGGATGA |
| 8161 GCTGACCAAG AACCAGGTCA GCCTGACCTG CCTGGTCAAA GGCTTCTATC CCAGCGACAT |
| 8221 CGCCGTGGAG TGGGAGAGCA ATGGGCAGCC GGAGAACAAC TACAAGACCA CGCCTCCCGT |
| 8281 GTTGGACTCC GACGGCTCCT TCTTCCTCTA CAGCAAGCTC ACCGTGGACA AGAGCAGGTG |
| 8341 GCAGCAGGGG AACGTCTTCT CATGCTCCGT GATGCATGAG GCTCTGCACA ACCACTACAC |
| 8401 GCAGAAGAGC CTCTCCCTGT CTCCGGGTAA A |
| (ii) Fc (SEQ ID NO: 3) |

TABLE 7

| Polypeptide Sequence: FVIII-Fc |
|---|
| A. B-Domain Deleted FVIII-Fc Monomer Hybrid (BDD FVIIIFc monomer dimer): created by coexpressing BDD FVIIIFc and Fc chains. Construct = HC-LC-Fc fusion. An Fc expression cassette is cotransfected with BDDFVIII-Fc to generate the BDD FVIIIFc monomer-. For the BDD FVIIIFc chain, the Fc sequence is shown in bold; HC sequence is shown in double underline; remaining B domain sequence is shown in italics. Signal peptides are underlined.<br>i) B domain deleted FVIII-Fc chain (19 amino acid signal sequence underlined) (SEQ ID NO: 6) |

FVIII SIGNAL PEPTIDE: -19 <u>MQIELSTCFFLCLLRFCFS</u>

FVIII MATURE POLYPEPTIDE SEQUENCE:
<u>ATRRYYLGAVELSWDYMQSDLGELPVDARFPPRVPKSFPFNTSVVYKKTLFVEFTDHLFNIAKPRPPW</u>

<u>MGLLGPTIQAEVYDTVVITLKNMASHPVSLHAVGVSYWKASEGAEYDDQTSQREKEDDKVFPGGSHTY</u>

<u>VWQVLKENGPMASDPLCLTYSYLSHVDLVKDLNSGLIGALLVCREGSLAKEKTQTLHKFILLFAVFDE</u>

<u>GKSWHSETKNSLMQDRDAASARAWPKMHTVNGYVNRSLPGLIGCHRKSVYWHVIGMGTTPEVHSIFLE</u>

<u>GHTFLVRNHRQASLEISPITFLTAQTLLMDLGQFLLFCHISSHQHDGMEAYVKVDSCPEEPQLRMKNN</u>

<u>EEAEDYDDDLTDSEMDVVRFDDDNSPSFIQIRSVAKKHPKTWVHYIAAEEEDWDYAPLVLAPDDRSYK</u>

<u>SQYLNNGPQRIGRKYKKVRFMAYTDETFKTREAIQHESGILGPLLYGEVGDTLLIIFKNQASRPYNIY</u>

<u>PHGITDVRPLYSRRLPKGVKHLKDFPILPGEIFKYKWTVTVEDGPTKSDPRCLTRYYSSFVNMERDLA</u>

<u>SGLIGPLLICYKESVDQRGNQIMSDKRNVILFSVFDENRSWYLTENIQRFLPNPAGVQLEDPEFQASN</u>

<u>IMHSINGYVFDSLQLSVCLHEVAYWYILSIGAQTDFLSVFFSGYTFKHKMVYEDTLTLFPFSGETVFM</u>

<u>SMENPGLWILGCHNSDFRNRGMTALLKVSSCDKNTGDYYEDSYEDISAYLLSKNNAIEPR</u>*SFSQNPPV*

*LKRHQR*EITRTTLQSDQEEIDYDDTISVEMKKEDFDIYDEDENQSPRSFQKKTRHYFIAAVERLWDYG

MSSSPHVLRNRAQSGSVPQFKKVVFQEFTDGSFTQPLYRGELNEHLGLLGPYIRAEVEDNIMVTFRNQ

TABLE 7-continued

| Polypeptide Sequence: FVIII-Fc |
|---|

ASRPYSFYSSLISYEEDQRQGAEPRKNFVKPNETKTYFWKVQHHMAPTKDEFDCKAWAYFSDVDLEKD

VHSGLIGPLLVCHTNTLNPAHGRQVTVQEFALFFTIFDETKSWYFTENMERNCRAPCNIQMEDPTFKE

NYRFHAINGYIMDTLPGLVMAQDQRIRWYLLSMGSNENIHSIHFSGHVFTVRKKEEYKMALYNLYPGV

FETVEMLPSKAGIWRVECLIGEHLHAGMSTLFLVYSNKCQTPLGMASGHIRDFQITASGQYGQWAPKL

ARLHYSGSINAWSTKEPFSWIKVDLLAPMIIHGIKTQGARQKFSSLYISQFIIMYSLDGKKWQTYRGN

STGTLMVFFGNVDSSGIKHNIFNPPIIARYIRLHPTHYSIRSTLRMELMGCDLNSCSMPLGMESKAIS

DAQITASSYFTNMFATWSPSKARLHLQGRSNAWRPQVNNPKEWLQVDFQKTMKVTGVTTQGVKSLLTS

MYVKEFLISSSQDGHQWTLFFQNGKVKVFQGNQDSFTPVVNSLDPPLLTRYLRIHPQSWVHQIALRME

VLGCEAQDLYDKTHTCPPCPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKALPAPIEKTISKAKGQPREP

QVYTLPPSRDELTKNQVSLTCLVKGFYPSDIAVEWESNGQPENNYKTTPPVLDSDGSFFLYSKLTVDK

SRWQQGNVFSCSVMHEALHNHYTQKSLSLSPGK ii) Fc chain (20 amino acid heterologous signal peptide from mouse
IgK chain underlined) (SEQ ID NO: 4)

FC SIGNAL PEPTIDE: <u>-20 METDTLLLWVLLLWVPGSTG</u>

FC SEQUENCE:
DKTHTCPPCPAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFS

CSVMHEALHNHYTQKSLSLSPGK

B. Full-length FVIIIFc monomer hybrid (Full-length FVIIIFc monomer
dimer): created by coexpressing FVIIIFc and Fc chains.
Construct = HC-B-LC-Fc fusion. An Fc expression cassette is
cotransfected with full-length FVIII-Fc to generate the full-length
FVIIIFc monomer. For the FVIIIFc chain, the Fc sequence is shown in
bold; HC sequence is shown in double underline; B domain sequence
is shown, in italics. Signal peptides are underlined.
i) Full-length FVIIIFc chain (FVIII signal peptide underlined
(SEQ ID NO: 8)

FVIII SIGNAL PEPTIDE: <u>-19 MQIELSTCFFLCLLRFCFS</u>

FVIII MATURE SEQUENCE:
<u>ATRRYYLGAVELSWDYMQSDLGELPVDARFPPRVPKSFPFNTSVVYKKTLFVEFTDHLFNIAKPRPPW</u>

<u>MGLLGPTIQAEVYDTVVITLKNMASHPVSLHAVGVSYWKASEGAEYDDQTSQREKEDDKVFPGGSHTY</u>

<u>VWQVLKENGPMASDPLCLTYSYLSHVDLVKDLNSGLIGALLVCREGSLAKEKTQTLHKFILLFAVFDE</u>

<u>GKSWHSETKNSLMQDRDAASARAWPKMHTVNGYVNRSLPGLIGCHRKSVYWHVIGMGTTPEVHSIFLE</u>

<u>GHTFLVRNHRQASLEISPITFLTAQTLLMDLGQFLLFCHISSHQHDGMEAYVKVDSCPEEPQLRMKNN</u>

<u>EEAEDYDDDLTDSEMDVVRFDDDNSPSFIQIRSVAKKHPKTWVHYIAAEEEDWDYAPLVLAPDDRSYK</u>

<u>SQYLNNGPQRIGRKYKKVRFMAYTDETFKTREAIQHESGILGPLLYGEVGDTLLIIFKNQASRPYNIY</u>

<u>PHGITDVRPLYSRRLPKGVKHLKDFPILPGEIFKYKWTVTVEDGPTKSDPRCLTRYYSSFVNMERDLA</u>

<u>SGLIGPLLICYKESVDQRGNQIMSDKRNVILFSVFDENRSWYLTENIQRFLPNPAGVQLEDPEFQASN</u>

<u>IMHSINGYVFDSLQLSVCLHEVAYWYILSIGAQTDFLSVFFSGYTFKHKMVYEDTLTLFPFSGETVFM</u>

<u>SMENPGLWILGCHNSDFRNRGMTALLKVSSCDKNTGDYYEDSYEDISAYLLSKNNAIEPR</u>*SFSQNSRH*

*PSTRQKQFNATTIPENDIEKTDPWFAHRTPMPKIQNVSSSDLLMLLRQSPTPHGLSLSDLQEAKYETF*

TABLE 7-continued

Polypeptide Sequence: FVIII-Fc

*SDDPSPGAIDSNNSLSEMTHFRPQLHHSGDMVFTPESGLQLRLNEKLGTTAATELKKLDFKVSSTSNN*

*LISTIPSDNLAAGTDNTSSLGPPSMPVHYDSQLDTTLFGKKSSPLTESGGPLSLSEENNDSKLLESGL*

*MNSQESSWGKNVSSTESGRLFKGKRAHGPALLTKDNALFKVSISLLKTNKTSNNSATNRKTHIDGPSL*

*LIENSPSVWQNILESDTEFKKVTPLIHDRMLMDKNATALRLNHMSNKTTSSKNMEMVQQKKEGPIPPD*

*AQNPDMSFFKMLFLPESARWIQRTHGKNSLNSGQGPSPKQLVSLGPEKSVEGQNFLSEKNKVVGKGE*

*FTKDVGLKEMVFPSSRNLFLTNLDNLHENNTHNQEKKIQEEIEKKETLIQENVVLPQIHTVTGTKNFM*

*KNLFLLSTRQNVEGSYDGAYAPVLQDFRSLNDSTNRTKKHTAHFSKKGEEENLEGLGNQTKQIVEKYA*

*CTTRISPNTSQQNFVTQRSKRALKQFRLPLEETELEKRIIVDDTSTQWSKNMKHLTPSTLTQIDYNEK*

*EKGAITQSPLSDCLTRSHSIPQANRSPLPIAKVSSFPSIRPIYLTRVLFQDNSSHLPAASYRKKDSGV*

*QESSHFLQGAKKNNLSLAILTLEMTGDQREVGSLGTSATNSVTYKKVENTVLPKPDLPKTSGKVELLP*

*KVHIYQKDLFPTETSNGSPGHLDLVEGSLLQGTEGAIKWNEANRPGKVPFLRVATESSAKTPSKLLDP*

*LAWDNHYGTQIPKEEWKSQEKSPEKTAFKKKDTILSLNACESNHAIAAINEGQNKPEIEVTWAKQGRT*

*ERLCSQNPPVLKRHQREITRTTLQSDQEEIDYDDTISVEMKKEDFDIYDEDENQSPRSFQKKTRHYFI*

*AAVERLWDYGMSSSPHVLRNRAQSGSVPQFKKVVFQEFTDGSFTQPLYRGELNEHLGLLGPYIRAEVE*

*DNIMVTFRNQASRPYSFYSSLISYEEDQRQGAEPRKNFVKPNETKTYFWKVQHHMAPTKDEFDCKAWA*

*YFSDVDLEKDVHSGLIGPLLVCHTNTLNPAHGRQVTVQEFALFFTIFDETKSWYFTENMERNCRAPCN*

*IQMEDPTFKENYRFHAINGYIMDTLPGLVMAQDQRIRWYLLSMGSNENIHSIHFSGHVFTVRKKEEYK*

*MALYNLYPGVFETVEMLPSKAGIWRVECLIGEHLHAGMSTLFLVYSNKCQTPLGMASGHIRDFQITAS*

*GQYGQWAPKLARLHYSGSINAWSTKEPFSWIKVDLLAPMIIHGIKTQGARQKFSSLYISQFIIMYSLD*

*GKKWQTYRGNSTGTLMVFFGNVDSSGIKHNIFNPPIIARYIRLHPTHYSIRSTLRMELMGCDLNSCSM*

*PLGMESKAISDAQITASSYFTNMFATWSPSKARLHLQGRSNAWRPQVNNPKEWLQVDFQKTMKVTGVT*

*TQGVKSLLTSMYVKEFLISSSQDGHQWTLFFQNGKVKVFQGNQDSFTPVVNSLDPPLLTRYLRIHPQS*

*WVHQIALRMEVLGCEAQDLY*DKTHTCPPCPAPELLGGPSVFLFPPKPKDTLMISRTPEVTCVVVDVSH*

*EDPEVKFNWYVDGVEVHNAKTKPREEQYNSTYRVVSVLTVLHQDWLNGKEYKCKVSNKALPAPIEKTI*

*SKAKGQPREPQVYTLPPSRDELTKNQVSLTCLVKGFYPSDIAVEWESNGQPENNYKTTPPVLDSDGSF*

*LYSKLTVDKSRWQQGNVFSCSVMHEALHNHYTQKSLSLSPGK* ii) Fc chain (20 amino acid heterologous signal peptide from mouse
IgK chain underlined) (SEQ ID NO: 4)

<u>METDTLLLWVLLLWVPGSTG</u>

DKTHTCPPCPAPELLGGPSVFLFPPKPKDTLMISRTPEVTCVVVDVSHEDPEVKFNWYVDGVEVHNAK

TKPREEQYNSTYRVVSVLTVLHQDWLNGKEYKCKVSNKALPAPIEKTISKAKGQPREPQVYTLPPSRD

ELTKNQVSLTCLVKGFYPSDIAVEWESNGQPENNYKTTPPVLDSDGSFFLYSKLTVDKSRWQQGNVFS

CSVMHEALHNHYTQKSLSLSPGK

TABLE 8

Additional Sequences

>CTP peptide 1                                          SEQ ID NO: 9

DPRFQDSSSSKAPPPSLPSPSRLPGPSDTPIL

TABLE 8-continued

Additional Sequences

>CTP peptide 2
SEQ ID NO: 10
SSSSKAPPPSLPSPSRLPGPSDTPILPQ

>PAS peptide 1
SEQ ID NO: 11
ASPAAPAPASPAAPAPSAPA

>PAS peptide 2
SEQ ID NO: 12
AAPASPAPAAPSAPAPAAPS

>PAS peptide 3
SEQ ID NO: 13
APSSPSPSAPSSPSPSASPSS

>PAS peptide 4
SEQ ID NO: 14
APSSPSPSAPSSPSPASPS

>PAS peptide 5
SEQ ID NO: 15
SSPSAPSPSSPASPSPSSPA

>PAS peptide 6
SEQ ID NO: 16
AASPAAPSAPPAAASPAAPSAPPA

>PAS peptide 7
SEQ ID NO: 17
ASAAAPAAASAAASAPSAAA

>Albumin Binding Peptide Core Sequence
SEQ ID NO: 18
DICLPRWGCLW

>GFP protein sequence (Genbank ID AAG34521.1)
SEQ ID NO: 19
MSKGEELFTGVVPILVELDGDVNGHKFSVSGEGEGDATYGKLTLKFICTTGKLPVPWPTL

VTTFGYGVQCFARYPDHMKQHDFFKSAMPEGYVQERTIFFKDDGNYKTRAEVKFEGDTLV

NRIELKGIDFKEDGNILGHKLEYNYNSHNVYIMADKQKNGIKVNFKIRHNIEDGSVQLAD

HYQQNTPIGDGPVLLPDNHYLSTQSALSKDPNEKRDHMVLLEFVTAAGITHGMDELYKSR

TSGSPGLQEFDIKLIDTVDLESCN

>Example: Single-chain Human IgG1 Fc. (Fc sequences with
Gly/Ser linker underlined.)
SEQ ID NO: 20
DKTHTCPPCPAPELLGGPSVFLFPPKPKDTLMISRTPEVTCVVVDVSHEDPEVKFNWYVD

GVEVENAKTKPREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK<u>GGGGSGGGGSGGG</u>

<u>GSGGGGS</u>DKTHTCPPCPAPELLGGPSVFLFPRKPKDTLMISRTPEVTCVVVDVSHEDPEV

KFNWYVDGVEVHNAKTKPREEQYNSTYRVVgVLTVLHQDWLNGKEYKCKVSNKALPAPIE

KTISKAKGQPREPQVYTLPPSRDELTKNQVSLTQINKGFYPSDIAVEWESNGQPENNYKT

TPPVLDSDGSFELYSKLTVDKSRWQQGNVFSCSVMHEALPINHYTQKSLSLSPGK

>Mature human albumin protein sequence (derived from NCBI
Ref. Sequence NP_000468)
SEQ ID NO: 21
RGVFRRDAHKSEVAHRFKDLGEENFKALVLIAFAQYLQQCPFEDHVKLVNEVTEFAKTCV

ADESAENCDKSLHTLFGDKLCTVATLRETYGEMADCCAKQEPERNECFLQHKDDNPNLPR

LVRPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVSKL

TABLE 8-continued

Additional Sequences

VTDLTKVHTECCHGDLLECADDRADLAKYICENQDSISSKLKECCEKPLLEKSHCIAEVE

NDEMPADLPSLAADFVESKDVCKNYAEAKDVFLGMFLYEYARRHPDYSVVLLLRLAKTYE

TTLEKCCAAADPHECYAKVFDEFKPLVEEPQNLIKQNCELFEQLGEYKFQNALLVRYTKK

VPQVSTPTLVEVSRNLGKVGSKCCKHPEAKRMPCAEDYLSVVLNQLCVLHEKTPVSDRVT

KCCTESLVNRRPCFSALEVDETYVPKEFNAETFTFHADICTLSEKERQIKKQTALVELVK

HKPKATKEQLKAVMDDFAAFVEKCCKADDKETCFAEEGKKLVAASQAALGL

>Albumin binding peptide 1
SEQ ID NO: 22
RLIEDICLPRWGCLWEDD

>Albumin binding peptide 2
SEQ ID NO: 23
QRLMEDICLPRWGCLWEDDF

>Albumin binding peptide 3
SEQ ID NO: 24
QGLIGDICLPRWGCLWGDSVK

>Albumin binding peptide 4
SEQ ID NO: 25
GEWWEDICLPRWGCLWEEED

>Cysteine-containing peptide
SEQ ID NO: 26
GGGSGCGGGS

>Human LRP1 sequence (signal peptide and transmembrane
segment underlined; NCBI Reference Sequence: CAA32112)
SEQ ID NO: 27
<u>MLTPPLLLLLPLLSALVAAA</u>IDAPKTCSPKQFACRDQITCISKGWRCDGERDCPDGSDEA

PEICPQSKAQRCQPNEHNCLGTELCVPMSRLCNGVQDCMDGSDEGRHCRELQGNCSRLGC

QHHCVPTLDGPTCYCNSSFQLQADOKTCKDFDECSVYGTCSQLCTNTDGSFICGCVEGYL

LQPDNRSCKAKNEPVDRPPVLLIANSQNILATYLSGAQVSTITPTSTRQTTAMDFSYANE

TVCWVHVGDSAAQTQLKCARMPGLKGFVDEHTINISLSLHHVEQMAIDWLTGNFYFVDDI

DDRIFVCNRNGDTCVTLLDLELYAPKGIALDPAMGKVEFTDYGQIPKVERCDMDGQNRTK

LVDSKIVFPHGITLDLVSRLVYWADAYLDYIEVVDYEGKGRQTIIQGILIEHLYGLTVFE

NYLYATNSDNANAQQKTSVIRVNRFNSTEYQVVTRVDKGGALHIYHQRRQPRVRSHACEN

DQYGKPGGCSDICLLANSHKARTCRCRSGFSLGSDGKSCKKPEHELFLVYGKGRPGIIRG

MDMGAKVPDEHMIPIENLMNPRALDFHAETGFIYFADTTSYLIGROCIDGTERETILKDG

IHNVEGVAVDWMGDNLYWTDDGPKKTISVARLEKAAQTRKTLIEGKMTHPRAIVVDPLNG

WMYWTDWEEDPKDSRRGRLERAWMDGSHRDIFVTSKTVLWPNGLSLDIPAGRLYWVDAFY

DRIETILLNGTDRKIVYEGPELNHAFGLCHHONYLFWTEYRSGSVYRLERGVGGAPPTVT

LLRSERPPIFEIRMYDAQQQQVGTNKCRVNNGGCSSLCLATRGSRQCACAEDQVLDADGV

TCLANPSYVPPPQCQPGEFACANSRCIQERWKCDGDNDCLDNSDEAPALCHQHTCPSDRF

KCENNRCIPNRWLCDGDNDCGNSEDESNATCSARTCPPNQFSCASGRCIPISWTCDLDDD

CGDRSDESASCAYPTCFPLTQFTCNNGRCININWRCDNDNDCGDNSDEAGCSHSCSSTQF

KCNSGRCIPEHWTCDGDNDCGDYSDETHANCTNQATRPPGGCHTDEFQCRLDGLCIPLRW

RCDGDTDCMDSSDEKSCEGVTHVCDRSVKFGOKDSARCISKAWVCDGDNDCEDNSDEENC

ESLACRPPSHPCANNTSVCLPPDKLCDGNDDCGDGSDEGELCDQCSLNNGGCSHNCSVAP

GEGIVCSCPLGMELGPDNHTCQIQSYCAKHLKCSQKCDQNKFSVKCSCYEGWVLEPDGES

TABLE 8-continued

Additional Sequences

CRSLDPFKPFIIFSNRHEIRRIDLHKGDYSVLVPGLRNTIALDFHLSQSALYWTDVVEDK
IYRGKLLDNGALTSFEVVIQYGLATPEGLAVDWIAGNIYWVESNLDQIEVAKLDGTLRTT
LLAGDIEHPRAIALDPRDGILFWTDWDASLPRIEAASMSGAGRRTVHRETGSGGWPNGLT
VDYLEKRILWIDARSDAIYSARYDGSGHMEVLRGHEFLSHPFAVTLYGGEVYWTDWRTNT
LAKANKWTGHNVTVVQRTNTQPFDLQVYHPSRQPMAPNPCEANGGQGPCSHLCLINYNRT
VSCACPHLMKLHKDNTTCYEFKKFLLYARQMEIRGVDLDAPYYNYIISFTVPDIDNVTVL
DYDAREQRVYWSDVRTQAIKRAFINGTGVETVVSADLPNAHGLAVDWVSRNLFWTSYDTN
KKQINVARLDGSFKNAVVQGLEQPHGLVVHPLRGKLYWTDGDNISMANMDGSNRTLLFSG
QKGPVGLAIDFPESKLYWISSGNHTINRCNLDGSGLEVIDAMRSQLGKATALAIMGDKLW
WADQVSEKMGTCSKADGSGSVVLRNSTTLVMHMKVYDESIQLDHKGTWPCSVNNGDCSQL
CLPTSETTRSCMCTAGYSLRSGQQACEGVGSFLLYSVHEGIRGIPLDPNDKSDALVPVSG
TSLAVGIDFHAENDTIYWVDMGLSTISRAKRDQTWREDVVTNGIGRVEGIAVDWIAGNIY
WTDQGFDVIEVARLNGSFRYVVISQGLDKPRAITVHPEKGYLFWTEWGQYPRIERSRLDG
TERVVLVNVSISWPNGISVDYQDGKLYWCDARTDKIERIDLETGENREVVLSSNNMDMES
VSVFEDFIYWSDRTHANGSIKRGSKDNATDSVPLRTGIGVQLKDIKVENRDRQKGTNVCA
VANGGCQQLCLYRGRGQRACACAHGMLAEDGASCREYAGYLLYSERTILKSIHLSDERNL
NAPVQPFEDPEHMKNVIALAFDYRAGTSPGTPNRIFFSDIHFGNIQQINDDGSRRITIVE
NVGSVEGLAYHROWDTLYWTSYTTSTITRHTVDQTRPGAFERETVITMSGDDHPRAFVLD
ECQNLMFWTNWNEQHPSIMRAALSGANVLTLIEKDIRTPNGLAIDHRAEKLYFSDATLDK
IERCEYDGSHRYVILKSEPVHPFGLAVYGEHIFWTDWVRRAVQRANKHVGSNMKLLRVDI
PQQPMGIIAVANDTNSCELSPCRINNOGCQDLCLLTHQGHVNCSORGGRILQDDLTCRAV
NSSCRAQDEFECANGECINFSLTCDGVPHCKDKSDEKPSYCNSRRCKKTFRQCSNGRCVS
NMLWCNGADDCGDGSDEIPCNKTACGVGEFRCRDGTCIGNSSRCNQFVDCEDASDEMNCS
ATDCSSYFRLGVKGVLFQPCERTSLCYAPSWVCDGANDCGDYSDERDCPGVKRPROPLNY
FACPSGRCIPMSWTCDKEDDCEHGEDETHCNKFCSEAQFECQNHRCISKQWLCDGSDDCG
DGSDEAAHCEGKTCGPSSFSCPGTHVCVPERWLCDGDKDCADGADESIAAGCLYNSTCDD
REFMCQNRQCIPKHFVCDHDRDCADGSDESPECEYPTCGPSEFRCANGRCLSSRQWECDG
ENDCHDQSDEAPKNPECTSPEHKCNASSQFLCSSGRCVAEALLONGQDDCGDSSDERGCH
INECLSRKLSGCSQDCEDLKIGFKCRCRPGFRLKDDGRTCADVDECSTTFPCSQRCINTH
GSYKCLCVEGYAPRGGDPHSCKAVTDEEPFLIFANRYYLRKLNLDGSNYTLLKQGLNNAV
ALDFDYREQMTYWTDVTTQGSMIRRMHLNGSNVQVLHRTGLSNPDGLAVDWVGGNLYWCD
KGRDTIEVSKLNGAYRTVLVSSGLREPRALVVDVQNGYLYWTDWGDHSLIGRIGMDGSSR
SVIVDTKITWPNGLTLDYVTERIYWADAREDYIEFASLDGSNRHVVLSQDIPHIFALTLF
EDYVYWTDWETKSINRAHKTTGTNKTLLISTLHRPMDLHVFHALRQPDVPNHPCKVNNGG
CSNLCLLSPGGGHKCACPTNFYLGSDGRTCVSNCTASQFVCKNDKCIPFWWKCDTEDDCG
DHSDEPPDCPEFKGRPGQFQCSTGICTNPAFICDGDNDCQDNSDEANCDIHVCLPSQFKC
TNTNRCIPGIFRCNGQDNCGDGEDERDCPEVTCAPNQFQCSITKRCIPRVWVCDRDNDCV
DGSDEPANCTQMTCGVDEFRCKDSGRCIPARWKCDGEDDCGDGSDEPKEECDERTCEPYQ
FRCKNNROVPGRWQCDYDNDCGDNSDEESCTPRPCSESEFSCANGRCIAGRWKCDGDHDC

TABLE 8-continued

Additional Sequences

ADGSDEKDCTPRCDMDQFQCKSGHCIPLRWRODADADCMDGSDEEACGTGVRTCPLDEFQ
CNNTLCKPLAWKCDGEDDCGDNSDENPEECARFVCPPNRPFRCKNDRVCLWIGRQCDGTD
NCGDGTDEEDCEPPIAHTTHCKDKKEFLCRNQRCLSSSLRCNMFDDCGDGSDEEDCSIDP
KLTSCATNASICGDEARCVRTEKAAYCACRSGFHTVPGQPGCQDINECLREGTCSQLCNN
TKGGHLCSCARNFMKTHNTCKAEGSEYQVLYIADDNEIRELFPGHPHSAYEQAFQGDESV
RIDAMDVHVKAGRVYWTNWHTGTISYRSLPPAAPPTTSNRHRRQIDROVTHLNISOLKMP
RGIAIDWVAGNVYWTDSGRDVIEVAQMKGENRKTLISGMIDEPHAIVVDPLRGTMYWSDW
GNHPKIETAAMDGTLRETLVQDNIQWPTGLAVDYHNERLYWADAKLSVIGSIRLNGTDPI
VAADSKRGLSHPFSIDVFEDYIYGVTYINNRVFKIHKFGHSPLVNLTGGLSHASDVVLYH
QHKQPEVTNPCDRKKCEWLCLLSPSGPVCTCPNGKRLDNGTCVPVPSPTPPPDAPRPGTC
NLQCFNGGSCFLNARRQPKCRCQPRYTGDKCELDQCWEHCRNGGTCAASPSGMPTCRCPT
GFTGPKCTQQVCAGYCANNSTCTVNQGNQPQCRCLPGFLGDRCQYRQCSGYCENFGTCQM
AADGSRQCRCTAYFEGSRCEVNKCSRCLEGACVVNKQSGDVTCNCTDGRVAPSCLTCVGH
CSNGGSCTMNSKMMPECQCPPHMTGPRCEEHVFSQQQPGHIAS<u>ILIPLLLLLLLVLVAGV</u>
<u>VFWY</u>KRRVQGAKGFQHQRMTNGAMNVE1GNPTYKMYEGGEPDDVGGLLDADFALDPDKPT
NFTNPVYATLYMGGHGSRHSLASTDEKRELLGRGPEDEIGDPLA

>Biotin Acceptor Peptide (BAP)                              SEQ ID NO: 28
LNDIFEAQKIEWH >Lipoate Acceptor Peptide 2 (LAP2)                          SEQ ID NO: 29
GFEIDKVWYDLDA >HAPylation motif, n = 1 to 400                             SEQ ID NO: 30
(Gly4Ser)n >CTP                                                        SEQ ID NO: 31
DSSSSKAPPPSLPSPSRLPGPSDTPILPQ

---

What is claimed is:

1. A method of treating hemophilia B in a subject in need thereof, comprising administering a fixed dose of chimeric Factor IX (FIX) polypeptide to the subject,
   wherein the fixed dose is standard across all body weight,
   wherein the fixed dose is administered weekly at a dose between about 3,000 IU and about 4,000 IU, and
   wherein the chimeric FIX polypeptide comprises:
   (i) a first polypeptide chain comprising a FIX-Fc amino acid sequence having at least 60%, 70%, 80%, 90%, 95%, 96%, 97%, 98%, 99%, or 100% sequence identity to the amino acid sequence according to SEQ ID NO: 2, and
   (ii) a second polypeptide chain comprising an Fc amino acid sequence having at least 60%, 70%, 80%, 90%, 95%, 96%, 97%, 98%, 99%, or 100% sequence identity sequence identity to the amino acid sequence according to SEQ ID NO: 4.

2. The method of claim 1, wherein the administering reduces or ameliorates one or more symptoms of hemophilia B.

3. The method of claim 1, wherein a body weight effect on clearance ($\theta_{BW\_CL}$) of the chimeric FIX polypeptide is equal to or less than about 0.500.

4. The method of claim 1, wherein a body weight effect on the central volume of distribution ($\theta_{BW\_V1}$) of the chimeric FIX polypeptide is equal to or less than about 0.467.

5. The method of claim 1, wherein the fixed dose is administered intravenously.

6. The method of claim 1, wherein the the fixed dose amount is about 3,000 IU per dose and wherein the fixed dose is administered weekly.

7. The method of claim 1, wherein the the fixed dose amount is about 4,000 IU per dose and wherein the fixed dose is administered weekly.

8. The method of claim 1, wherein the chimeric FIX polypeptide comprises:
   (i) a first polypeptide chain comprising a FIX-Fc amino acid sequence according to SEQ ID NO: 2; and
   (ii) a second polypeptide chain comprising a Fc amino acid sequence according to SEQ ID NO: 4.

9. A method of treating hemophilia B in a subject in need thereof, comprising administering a fixed dose of a chimeric FIX polypeptide to the subject,
   wherein the fixed dose is standard across all body weight,
   wherein the fixed dose is administered every 10 days at a dose between about 6,000 IU and about 8,000 IU, and
   wherein the chimeric FIX polypeptide comprises:
   (i) a first polypeptide chain comprising a FIX-Fc amino acids sequence having at least 60%, 70%, 80%, 90%, 95%, 96%, 97%, 98%, 99%, or 100% sequence identity to the amino acid sequence according to SEQ ID NO: 2; and
   (ii) a second polypeptide chain comprising an Fc amino acid sequence having at least 60%, 70%, 80%, 90%, 95%, 96%, 97%, 98%, 99%, or 100% sequence identity sequence identity to the amino acid sequence according to SEQ ID NO: 4.

10. The method of claim 9, wherein the fixed dose is administered intravenously.

11. The method of claim 9, wherein the fixed dose is about 6,000 IU per dose and wherein the fixed dose is administered every 10 days. intravaneously.

12. The method of claim 9, wherein the fixed dose amount is about 7,500 IU per dose and wherein the fixed dose is administered every 10 days.

13. The method of claim 9, wherein the fixed dose amount is about 8,000 IU per dose and wherein the fixed dose is administered every 10 days.

14. The method of claim 9, wherein the chimeric FIX polypeptide comprises:
   (i) a first polypeptide chain comprising a FIX-Fc amino acid sequence according to SEQ ID NO: 2; and
   (ii) a second polypeptide chain comprising a Fc amino acid sequence according to SEQ ID NO: 4.

\* \* \* \* \*

SEQUENCE LISTING

```
<160> NUMBER OF SEQ ID NOS: 31

<210> SEQ ID NO 1
<211> LENGTH: 7583
<212> TYPE: DNA
<213> ORGANISM: Artificial Sequence
<220> FEATURE:
<223> OTHER INFORMATION: pSYN-FIX-030
<220> FEATURE:
<221> NAME/KEY: sig_peptide
<222> LOCATION: (690)..(777)
<223> OTHER INFORMATION: FIX exon 1, 1st amino acid propeptide
<220> FEATURE:
<221> NAME/KEY: Intron
<222> LOCATION: (778)..(1076)
<223> OTHER INFORMATION: FIX mini intron
<220> FEATURE:
<221> NAME/KEY: misc_feature
<222> LOCATION: (1077)..(1126)
<223> OTHER INFORMATION: FIX propeptide
<220> FEATURE:
<221> NAME/KEY: misc_feature
<222> LOCATION: (1127)..(2371)
```

<223> OTHER INFORMATION: mature FIX sequence
<220> FEATURE:
<221> NAME/KEY: misc_feature
<222> LOCATION: (2372)..(3052)
<223> OTHER INFORMATION: Fc region

<400> SEQUENCE: 1

```
gcgcgcgttg acattgatta ttgactagtt attaatagta atcaattacg gggtcattag      60
ttcatagccc atatatggag ttccgcgtta cataacttac ggtaaatggc ccgcctggct     120
gaccgcccaa cgaccccgc ccattgacgt caataatgac gtatgttccc atagtaacgc     180
caatagggac tttccattga cgtcaatggg tggagtattt acggtaaact gcccacttgg     240
cagtacatca agtgtatcat atgccaagta cgccccctat tgacgtcaat gacggtaaat     300
ggcccgcctg gcattatgcc cagtacatga ccttatggga ctttcctact tggcagtaca     360
tctacgtatt agtcatcgct attaccatgg tgatgcggtt ttggcagtac atcaatgggc     420
gtggatagcg gtttgactca cggggatttc caagtctcca ccccattgac gtcaatggga     480
gtttgttttg gcaccaaaat caacgggact ttccaaaatg tcgtaacaac tccgccccat     540
tgacgcaaat gggcggtagg cgtgtacggt gggaggtcta taagcagag ctctctggc     600 taactagaga acccactgct tactggctta tcgaaattaa tacgactcac tatagggaga     660
cccaagcttc gcgacgtacg gccgccacca tgcagcgcgt gaacatgatc atggcagaat     720
caccaggcct catcaccatc tgcctttag gatatctact cagtgctgaa tgtacaggtt     780
tgtttccttt tttaaaatac attgagtatg cttgcctttt agatatagaa atatctgatg     840
ctgtcttctt cactaaattt tgattacatg atttgacagc aatattgaag agtctaacag     900
ccagcacgca ggttggtaag tactgtggga acatcacaga ttttggctcc atgccctaaa     960
gagaaattgg ctttcagatt atttggatta aaaacaaaga ctttcttaag agatgtaaaa    1020
ttttcatgat gttttctttt ttgctaaaac taaagaatta ttcttttaca tttcagtttt    1080
tcttgatcat gaaaacgcca acaaaattct gaatcggcca aagagtata attcaggtaa    1140 attggaagag tttgttcaag ggaatctaga gagagaatgt atggaagaaa agtgtagttt    1200
tgaagaagca cgagaagttt ttgaaaacac tgaaagaaca actgaatttt ggaagcagta    1260
tgttgatgga gatcagtgtg agtccaatcc atgtttaaat ggcggcagtt gcaaggatga    1320
cattaattcc tatgaatgtt ggtgtccctt tggatttgaa ggaagaact gtgaattaga    1380 tgtaacatgt aacattaaga tggcagatg cgagcagttt tgtaaaaata gtgctgataa    1440
caaggtggtt tgctcctgta ctgagggata tcgacttgca gaaaaccaga agtcctgtga    1500
accagcagtg ccatttccat gtggaagagt ttctgtttca caacttcta agctcacccg    1560 tgctgagact gtttttcctg atgtggacta tgtaaattct actgaagctg aaaccattt    1620 ggataacatc actcaaagca cccaatcatt taatgacttc actcggggttg ttggtggaga    1680 agatgccaaa ccaggtcaat tcccttggca ggttgtttg aatggtaaag ttgatgcatt    1740
ctgtggaggc tctatcgtta atgaaaaatg gattgtaact gctgccact gtgttgaaac    1800 tggtgttaaa attacagttg tcgcaggtga acataatatt gaggagacag aacatacaga    1860
gcaaaagcga aatgtgattc gaattattcc tcaccacaac tacaatgcag ctattaataa    1920
gtacaaccat gacattgccc ttctggaact ggacgaaccc ttagtgctaa acagctacgt    1980
tacacctatt tgcattgctg acaaggaata cacgaacatc ttcctcaaat ttggatctgg    2040
ctatgtaagt ggctggggaa gagtcttcca caaagggaga tcagctttag tcttcagta    2100 ccttagagtt ccacttgttg accgagccac atgtcttcga tctacaaagt tcaccatcta    2160
```

```
taacaacatg ttctgtgctg gcttccatga aggaggtaga gattcatgtc aaggagatag    2220
tgggggaccc catgttactg aagtggaagg gaccagtttc ttaactggaa ttattagctg    2280
gggtgaagag tgtgcaatga aaggcaaata tggaatatat accaaggtgt cccggtatgt    2340
caactggatt aaggaaaaaa caaagctcac tgacaaaact cacacatgcc caccgtgccc    2400
agctccggaa ctcctgggcg gaccgtcagt cttcctcttc cccccaaaac ccaaggacac    2460
cctcatgatc tcccggaccc ctgaggtcac atgcgtggtg gtggacgtga gccacgaaga    2520
ccctgaggtc aagttcaact ggtacgtgga cggcgtggag gtgcataatg ccaagacaaa    2580
gccgcgggag gagcagtaca acagcacgta ccgtgtggtc agcgtcctca ccgtcctgca    2640
ccaggactgg ctgaatggca aggagtacaa gtgcaaggtc tccaacaaag ccctcccagc    2700
ccccatcgag aaaaccatct ccaaagccaa agggcagccc cgagaaccac aggtgtacac    2760
cctgccccca tcccgggatg agctgaccaa gaaccaggtc agcctgacct gcctggtcaa    2820
aggcttctat cccagcgaca tcgccgtgga gtgggagagc aatgggcagc cggagaacaa    2880
ctacaagacc acgcctcccg tgttggactc cgacggctcc ttcttcctct acagcaagct    2940
caccgtggac aagagcaggt ggcagcaggg gaacgtcttc tcatgctccg tgatgcatga    3000
ggctctgcac aaccactaca cgcagaagag cctctccctg tctccgggta aatgagaatt    3060
cagacatgat aagatacatt gatgagtttg gacaaaccac aactagaatg cagtgaaaaa    3120
aatgctttat ttgtgaaatt tgtgatgcta ttgctttatt tgtaaccatt ataagctgca    3180
ataaacaagt tggggtgggc gaagaactcc agcatgagat cccgcgctg gaggatcatc     3240 cagccggcgt cccggaaaac gattccgaag cccaaccttt catagaaggc ggcggtggaa    3300
tcgaaatctc gtagcacgtg tcagtcctgc tcctcggcca cgaagtgcac gcagttgccg    3360
gccgggtcgc gcagggcgaa ctcccgcccc cacggctgct cgccgatctc ggtcatggcc    3420
ggcccggagg cgtcccggaa gttcgtggac acgacctccg accactcggc gtacagctcg    3480
tccaggccgc gcacccacac ccaggccagg gtgttgtccg gcaccacctg gtcctggacc    3540
gcgctgatga cagggtcac gtcgtcccgg accacaccgg cgaagtcgtc ctccacgaag     3600
tcccgggaga cccgagccg tcggtccag aactcgaccg ctccggcgac gtcgcgcgcg     3660
gtgagcaccg gaacggcact ggtcaacttg gccatggttt agttcctcac cttgtcgtat    3720
tatactatgc cgatatacta tgccgatgat taattgtcaa cacgtgctga tcagatccga    3780
aaatggatat acaagctccc gggagctttt tgcaaaagcc taggcctcca aaaaagcctc    3840
ctcactactt ctggaatagc tcagaggcag aggcggcctc ggcctctgca taataaaaa    3900 aaattagtca gccatggggc ggagaatggg cggaactggg cggagttagg ggcgggatgg    3960
gcggagttag ggcgggact atggttctg actaattgag atgcatgctt tgcatacttc      4020
tgcctgctgg ggagcctggg actttccac acctggttgc tgactaattg agatgcatgc     4080
tttgcatact tctgcctgct ggggagcctg gggactttcc acaccctcgt cgagctagct    4140
tcgtgaggct ccggtgcccg tcagtgggca gagcgcacat cgcccacagt ccccgagaag    4200
ttggggggag gggtcggcaa ttgaaccggt gcctagagaa ggtggcgcgg ggtaaactgg    4260
gaaagtgatg tcgtgtactg gctccgcctt tttcccgagg gtgggggaga accgtatata    4320
agtgcagtag tcgccgtgaa cgttcttttt cgcaacgggt ttgccgccag aacacaggta    4380
agtgccgtgt gtggttcccg cgggcctggc ctctttacgg gttatggccc ttgcgtgcct    4440
tgaattactt ccacctggct ccagtacgtg attcttgatc ccgagctgga gccaggggcg    4500
```

| | |
|---|---|
| ggccttgcgc tttaggagcc ccttcgcctc gtgcttgagt tgaggcctgg cctgggcgct | 4560 |
| ggggccgccg cgtgcgaatc tggtggcacc ttcgcgcctg tctcgctgct ttcgataagt | 4620 |
| ctctagccat ttaaaatttt tgatgacctg ctgcgacgct ttttttctgg caagatagtc | 4680 |
| ttgtaaatgc gggccaggat ctgcacactg gtatttcggt ttttgggggcc gcgggcggcg | 4740 |
| acggggcccg tgcgtcccag cgcacatgtt cggcgaggcg gggcctgcga gcgcggccac | 4800 |
| cgagaatcgg acggggtag tctcaagctg gccggcctgc tctggtgcct ggcctcgcgc | 4860 |
| cgccgtgtat cgccccgccc tgggcggcaa ggctggcccg gtcggcacca gttgcgtgag | 4920 |
| cggaaagatg gccgcttccc ggccctgctc caggggctc aaaatggagg acgcggcgct | 4980 |
| cgggagagcg ggcgggtgag tcacccacac aaaggaaagg ggcctttccg tcctcagccg | 5040 |
| tcgcttcatg tgactccacg gagtaccggg cgccgtccag gcacctcgat tagttctgga | 5100 |
| gcttttggag tacgtcgtct ttaggttggg gggaggggtt ttatgcgatg gagtttcccc | 5160 |
| acactgagtg ggtggagact gaagttaggc cagcttggca cttgatgtaa ttctccttgg | 5220 |
| aatttgccct ttttgagttt ggatcttggt tcattctcaa gcctcagaca gtggttcaaa | 5280 |
| gtttttttct tccatttcag gtgtcgtgaa cacgtggtcg cggccgcgcc gccaccatgg | 5340 |
| agacagacac actcctgcta tgggtactgc tgctctgggt tccaggttcc actggtgaca | 5400 |
| aaactcacac atgcccaccg tgcccagcac ctgaactcct gggaggaccg tcagtcttcc | 5460 |
| tcttcccccc aaaacccaag gacaccctca tgatctcccg gacccctgag gtcacatgcg | 5520 |
| tggtggtgga cgtgagccac gaagaccctg aggtcaagtt caactggtac gtggacggcg | 5580 |
| tggaggtgca taatgccaag acaaagccgc gggaggagca gtacaacagc acgtaccgtg | 5640 |
| tggtcagcgt cctcaccgtc ctgcaccagg actggctgaa tggcaaggag tacaagtgca | 5700 |
| aggtctccaa caaagccctc ccagccccca tcgagaaaac catctccaaa gccaaagggc | 5760 |
| agccccgaga accacaggtg tacaccctgc cccatcccg cgatgagctg accaagaacc | 5820 |
| aggtcagcct gacctgcctg gtcaaaggct tctatcccag cgacatcgcc gtggagtggg | 5880 |
| agagcaatgg gcagccggag aacaactaca agaccacgcc tcccgtgttg gactccgacg | 5940 |
| gctccttctt cctctacagc aagctcaccg tggacaagag caggtggcag caggggaacg | 6000 |
| tcttctcatg ctccgtgatg catgaggctc tgcacaacca ctacacgcag aagagcctct | 6060 |
| ccctgtctcc gggtaaatga ctcgagagat ctggccggct gggcccgttt cgaaggtaag | 6120 |
| cctatcccta accctctcct cggtctcgat tctacgcgta ccggtcatca tcaccatcac | 6180 |
| cattgagttt aaacccgctg atcagcctcg actgtgcctt ctagttgcca gccatctgtt | 6240 |
| gtttgcccct ccccgtgcc ttccttgacc ctggaaggtg ccactcccac tgtcctttcc | 6300 |
| taataaaatg aggaaattgc atcgcattgt ctgagtaggt gtcattctat tctgggggt | 6360 |
| ggggtggggc aggacagcaa gggggaggat tgggaagaca atagcaggca tgctggggat | 6420 |
| gcggtgggct ctatggcttc tgaggcggaa agaaccagtg gcgtaatac ggttatccac | 6480 |
| agaatcaggg gataacgcag gaaagaacat gtgagcaaaa ggccagcaaa aggccaggaa | 6540 |
| ccgtaaaaag gccgcgttgc tggcgttttt ccataggctc cgcccccctg acgagcatca | 6600 |
| caaaaatcga cgctcaagtc agaggtggcg aaacccgaca ggactataaa gataccaggc | 6660 |
| gtttccccct agaagctccc tcgtgcgctc tcctgttccg accctgccgc ttaccggata | 6720 |
| cctgtccgcc tttctccctt cgggaagcgt ggcgctttct catagctcac gctgtaggta | 6780 |
| tctcagttcg gtgtaggtcg ttcgctccaa gctgggctgt gtgcacgaac cccccgttca | 6840 |
| gcccgaccgc tgcgccttat ccggtaacta tcgtcttgag tccaacccgg taagcacga | 6900 |

-continued

```
cttatcgcca ctggcagcag ccactggtaa caggattagc agagcgaggt atgtaggcgg    6960
tgctacagag ttcttgaagt ggtggcctaa ctacggctac actagaagaa cagtatttgg    7020
tatctgcgct ctgctgaagc cagttacctt cggaaaaaga gttggtagct cttgatccgg    7080
caaacaaacc accgctggta gcggtggttt ttttgtttgc aagcagcaga ttacgcgcag    7140
aaaaaaagga tctcaagaag atcctttgat cttttctacg gggtctgacg ctcagtggaa    7200
cgaaaactca cgttaaggga ttttggtcat gacattaacc tataaaaata ggcgtatcac    7260
gaggcccttt cgtctcgcgc gtttcggtga tgacggtgaa aacctctgac acatgcagct    7320
cccggagacg gtcacagctt gtctgtaagc ggatgccggg agcagacaag cccgtcaggg    7380
cgcgtcagcg ggtgttggcg ggtgtcgggg ctggcttaac tatgcggcat cagagcagat    7440
tgtactgaga gtgcaccata tatgcggtgt gaaataccgc acagatgcgt aaggagaaaa    7500
taccgcatca ggcgccattc gccattcagg ctgcgcaact gttgggaagg gcgatcggtg    7560
cgggcctctt cgctattacg cca                                           7583
```

<210> SEQ ID NO 2
<211> LENGTH: 688
<212> TYPE: PRT
<213> ORGANISM: Artificial Sequence
<220> FEATURE:
<223> OTHER INFORMATION: FIX-Fc chain
<220> FEATURE:
<221> NAME/KEY: SIGNAL
<222> LOCATION: (1)..(28)
<223> OTHER INFORMATION: FIX signal peptide
<220> FEATURE:
<221> NAME/KEY: PROPEP
<222> LOCATION: (29)..(46)
<223> OTHER INFORMATION: FIX propeptide

<400> SEQUENCE: 2

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190
```

-continued

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
        355                 360                 365

Leu Gln Tyr Leu Arg Val Pro Leu Val Asp Arg Ala Thr Cys Leu Arg
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr Asp Lys Thr
450                 455                 460

His Thr Cys Pro Pro Cys Pro Ala Pro Glu Leu Leu Gly Gly Pro Ser
465                 470                 475                 480

Val Phe Leu Phe Pro Pro Lys Pro Lys Asp Thr Leu Met Ile Ser Arg
                485                 490                 495

Thr Pro Glu Val Thr Cys Val Val Val Asp Val Ser His Glu Asp Pro
            500                 505                 510

Glu Val Lys Phe Asn Trp Tyr Val Asp Gly Val Glu Val His Asn Ala
        515                 520                 525

Lys Thr Lys Pro Arg Glu Glu Gln Tyr Asn Ser Thr Tyr Arg Val Val
    530                 535                 540

Ser Val Leu Thr Val Leu His Gln Asp Trp Leu Asn Gly Lys Glu Tyr
545                 550                 555                 560

Lys Cys Lys Val Ser Asn Lys Ala Leu Pro Ala Pro Ile Glu Lys Thr
                565                 570                 575

Ile Ser Lys Ala Lys Gly Gln Pro Arg Glu Pro Gln Val Tyr Thr Leu
            580                 585                 590

Pro Pro Ser Arg Asp Glu Leu Thr Lys Asn Gln Val Ser Leu Thr Cys
        595                 600                 605

Leu Val Lys Gly Phe Tyr Pro Ser Asp Ile Ala Val Glu Trp Glu Ser

Asn Gly Gln Pro Glu Asn Asn Tyr Lys Thr Thr Pro Pro Val Leu Asp
625                 630                 635                 640

Ser Asp Gly Ser Phe Phe Leu Tyr Ser Lys Leu Thr Val Asp Lys Ser
                645                 650                 655

Arg Trp Gln Gln Gly Asn Val Phe Ser Cys Ser Val Met His Glu Ala
            660                 665                 670

Leu His Asn His Tyr Thr Gln Lys Ser Leu Ser Leu Ser Pro Gly Lys
        675                 680                 685

<210> SEQ ID NO 3
<211> LENGTH: 741
<212> TYPE: DNA
<213> ORGANISM: Artificial Sequence
<220> FEATURE:
<223> OTHER INFORMATION: Fc cassette from pSYN-FIX-030
<220> FEATURE:
<221> NAME/KEY: sig_peptide
<222> LOCATION: (1)..(60)
<223> OTHER INFORMATION: mouse Igkappa signal peptide

<400> SEQUENCE: 3
atggagacag acacactcct gctatgggta ctgctgctct gggttccagg ttccactggt    60
gacaaaactc acacatgccc accgtgccca gcacctgaac tcctgggagg accgtcagtc   120
ttcctcttcc ccccaaaacc caaggacacc ctcatgatct cccggacccc tgaggtcaca   180
tgcgtggtgg tggacgtgag ccacgaagac cctgaggtca agttcaactg gtacgtggac   240
ggcgtggagg tgcataatgc caagacaaag ccgcgggagg agcagtacaa cagcacgtac   300
cgtgtggtca gcgtcctcac cgtcctgcac caggactggc tgaatggcaa ggagtacaag   360
tgcaaggtct ccaacaaagc cctcccagcc cccatcgaga aaaccatctc caaagccaaa   420
gggcagcccc gagaaccaca ggtgtacacc ctgcccccat cccgcgatga gctgaccaag   480
aaccaggtca gcctgacctg cctggtcaaa ggcttctatc ccagcgacat cgccgtggag   540
tgggagagca atgggcagcc ggagaacaac tacaagacca cgcctcccgt gttggactcc   600
gacggctcct tcttcctcta cagcaagctc accgtggaca agagcaggtg gcagcagggg   660
aacgtcttct catgctccgt gatgcatgag gctctgcaca accactacac gcagaagagc   720
ctctccctgt ctccgggtaa a                                             741

<210> SEQ ID NO 4
<211> LENGTH: 247
<212> TYPE: PRT
<213> ORGANISM: Artificial Sequence
<220> FEATURE:
<223> OTHER INFORMATION: Fc chain
<220> FEATURE:
<221> NAME/KEY: SIGNAL
<222> LOCATION: (1)..(20)
<223> OTHER INFORMATION: heterologous mouse Igkappa light chain signal
      peptide

<400> SEQUENCE: 4

Met Glu Thr Asp Thr Leu Leu Leu Trp Val Leu Leu Leu Trp Val Pro
1               5                   10                  15

Gly Ser Thr Gly Asp Lys Thr His Thr Cys Pro Pro Cys Pro Ala Pro
            20                  25                  30

Glu Leu Leu Gly Gly Pro Ser Val Phe Leu Phe Pro Pro Lys Pro Lys
        35                  40                  45

Asp Thr Leu Met Ile Ser Arg Thr Pro Glu Val Thr Cys Val Val Val

```
            50                  55                  60
Asp Val Ser His Glu Asp Pro Glu Val Lys Phe Asn Trp Tyr Val Asp
 65                  70                  75                  80

Gly Val Glu Val His Asn Ala Lys Thr Lys Pro Arg Glu Glu Gln Tyr
                 85                  90                  95

Asn Ser Thr Tyr Arg Val Val Ser Val Leu Thr Val Leu His Gln Asp
            100                 105                 110

Trp Leu Asn Gly Lys Glu Tyr Lys Cys Lys Val Ser Asn Lys Ala Leu
        115                 120                 125

Pro Ala Pro Ile Glu Lys Thr Ile Ser Lys Ala Lys Gly Gln Pro Arg
    130                 135                 140

Glu Pro Gln Val Tyr Thr Leu Pro Pro Ser Arg Asp Glu Leu Thr Lys
145                 150                 155                 160

Asn Gln Val Ser Leu Thr Cys Leu Val Lys Gly Phe Tyr Pro Ser Asp
                165                 170                 175

Ile Ala Val Glu Trp Glu Ser Asn Gly Gln Pro Glu Asn Asn Tyr Lys
            180                 185                 190

Thr Thr Pro Pro Val Leu Asp Ser Asp Gly Ser Phe Phe Leu Tyr Ser
        195                 200                 205

Lys Leu Thr Val Asp Lys Ser Arg Trp Gln Gln Gly Asn Val Phe Ser
    210                 215                 220

Cys Ser Val Met His Glu Ala Leu His Asn His Tyr Thr Gln Lys Ser
225                 230                 235                 240

Leu Ser Leu Ser Pro Gly Lys
            245

<210> SEQ ID NO 5
<211> LENGTH: 5052
<212> TYPE: DNA
<213> ORGANISM: Artificial Sequence
<220> FEATURE:
<223> OTHER INFORMATION: B-Domain Deleted FVIIIFc
<220> FEATURE:
<221> NAME/KEY: sig_peptide
<222> LOCATION: (1)..(57)
<223> OTHER INFORMATION: FVIII signal peptide
<220> FEATURE:
<221> NAME/KEY: misc_feature
<222> LOCATION: (4371)..(5052)
<223> OTHER INFORMATION: Fc region

<400> SEQUENCE: 5
atgcaaatag agctctccac ctgcttcttt ctgtgccttt tgcgattctg ctttagtgcc      60
accagaagat actacctggg tgcagtggaa ctgtcatggg actatatgca agtgatctc     120 ggtgagctgc ctgtggacgc aagatttcct cctagagtgc caaatctttt ccattcaac     180 acctcagtcg tgtacaaaaa gactctgttt gtagaattca cggatcacct tttcaacatc    240
gctaagccaa ggccaccctg gatgggtctg ctaggtccta ccatccaggc tgaggtttat    300
gatacagtgg tcattacact taagaacatg gcttcccatc ctgtcagtct tcatgctgtt    360
ggtgtatcct actggaaagc ttctgaggga gctgaatatg atgatcagac cagtcaaagg    420
gagaaagaag atgataaagt cttccctggt ggaagccata catatgtctg caggtcctg     480 aaagagaatg gtccaatggc ctctgaccca ctgtgcctta cctactcata tctttctcat    540
gtggacctgg taaaagactt gaattcaggc ctcattggag ccctactagt atgtagagaa    600
gggagtctgg ccaaggaaaa gacacagacc ttgcacaaat ttatactact ttttgctgta    660
tttgatgaag ggaaaagttg gcactcagaa acaaagaact ccttgatgca ggataggat    720
```

```
gctgcatctg ctcgggcctg gcctaaaatg cacacagtca atggttatgt aaacaggtct    780
ctgccaggtc tgattggatg ccacaggaaa tcagtctatt ggcatgtgat tggaatgggc    840
accactcctg aagtgcactc aatattcctc gaaggtcaca catttcttgt gaggaaccat    900
cgccaggcgt ccttggaaat ctcgccaata actttcctta ctgctcaaac actcttgatg    960
gaccttggac agtttctact gttttgtcat atctcttccc accaacatga tggcatggaa   1020
gcttatgtca agtagacag ctgtccagag aacccccaac tacgaatgaa aaataatgaa    1080
gaagcggaag actatgatga tgatcttact gattctgaaa tggatgtggt caggtttgat   1140
gatgacaact ctccttcctt tatccaaatt cgctcagttg ccaagaagca tcctaaaact   1200
tgggtacatt acattgctgc tgaagaggag gactgggact atgctcsctt agtcctcgcc   1260
cccgatgaca gaagttataa aagtcaatat ttgaacaatg gccctcagcg gattggtagg   1320
aagtacaaaa aagtccgatt tatggcatac acagatgaaa cctttaagac tcgtgaagct   1380
attcagcatg aatcaggaat cttgggacct ttactttatg gggaagttgg agacacactg   1440
ttgattatat ttaagaatca agcaagcaga ccatataaca tctaccctca cggaatcact   1500
gatgtccgtc ctttgtattc aaggagatta ccaaaaggtg taaaacattt gaaggatttt   1560
ccaattctgc aggagaaat attcaaatat aaatggacag tgactgtaga agatgggcca   1620
actaaatcag atcctcggtg cctgacccgc tattactcta gtttcgttaa tatggagaga   1680
gatctagctt caggactcat tggccctctc ctcatctgct acaaagaatc tgtagatcaa   1740
agaggaaacc agataatgtc agacaagagg aatgtcatcc tgttttctgt atttgatgag   1800
aaccgaagct ggtacctcac agagaatata caacgctttc tccccaatcc agctggagtg   1860
cagcttgagg atccagagtt ccaagcctcc aacatcatgc acagcatcaa tggctatgtt   1920
tttgatagtt tgcagttgtc agtttgtttg catgaggtgg catactggta cattctaagc   1980
attggagcac agactgactt cctttctgtc ttcttctctg gatatacctt caaacacaaa   2040
atggtctatg aagacacact caccctattc ccattctcag gagaaactgt cttcatgtcg   2100
atggaaaacc caggtctatg gattctgggg tgccacaact cagactttcg gaacagaggc   2160
atgaccgcct tactgaaggt ttctagttgt gacaagaaca ctggtgatta ttacgaggac   2220
agttatgaag atatttcagc atacttgctg agtaaaaaca atgccattga accaagaagc   2280
ttctctcaaa acccaccagt cttgaaacgc atcaacgggg aataactcg tactactctt   2340
cagtcagatc aagaggaaat tgactatgat gataccatat cagttgaaat gaagaaggaa   2400
gattttgaca tttatgatga ggatgaaaat cagagccccc gcagctttca aaagaaaaca   2460
cgacactatt ttattgctgc agtggagagg ctctgggatt atgggatgag tagctcccca   2520
catgttctaa gaaacagggc tcagagtggc agtgtccctc agttcaagaa agttgttttc   2580
caggaattta ctgatggctc ctttactcag cccttatacc gtggagaact aaatgaacat   2640
ttgggactcc tggggccata taagagcaa gaagttgaag ataatatcat ggtaactttc   2700
agaaatcagg cctctcgtcc ctattccttc tattctagcc ttatttctta tgaggaagat   2760
cagaggcaag gagcagaacc tagaaaaaac tttgtcaagc ctaatgaaac caaaacttac   2820
ttttggaaag tgcaacatca tatggcaccc actaaagatg agtttgactg caaagcctgg   2880
gcttatttct ctgatgttga cctggaaaaa gatgtgcact caggcctgat tggacccctt   2940
ctggtctgcc acactaacac actgaaccct gctcatggga caagtgac agtacaggaa    3000
tttgctctgt ttttcaccat ctttgatgag accaaaagct ggtacttcac tgaaaatatg   3060
```

```
gaaagaaact gcagggctcc ctgcaatatc cagatggaag atcccacttt taaagagaat   3120
tatcgcttcc atgcaatcaa tggctacata atggatacac tacctggctt agtaatggct   3180
caggatcaaa ggattcgatg gtatctgctc agcatgggca gcaatgaaaa catccattct   3240
attcatttca gtggacatgt gttcactgta cgaaaaaaag aggagtataa aatggcactg   3300
tacaatctct atccaggtgt ttttgagaca gtggaaatgt taccatccaa agctggaatt   3360
tggcgggtgg aatgccttat tggcgagcat ctacatgctg ggatgagcac acttttctg    3420 gtgtacagca ataagtgtca gactcccctg ggaatggctt ctggacacat tagagatttt   3480
cagattacag cttcaggaca atatggacag tgggccccaa agctggccag acttcattat   3540
tccggatcaa tcaatgcctg gagcaccaag gagcccttt cttggatcaa ggtggatctg   3600
ttggcaccaa tgattattca cggcatcaag acccagggtg cccgtcagaa gttctccagc   3660
ctctacatct ctcagtttat catcatgtat agtcttgatg ggaagaagtg gcagacttat   3720
cgaggaaatt ccactggaac cttaatggtc ttctttggca atgtggattc atctgggata   3780
aaacacaata ttttttaaccc tccaattatt gctcgataca ccgtttgca cccaactcat    3840 tatagcattc gcagcactct tcgcatggag ttgatgggct gtgatttaaa tagttgcagc   3900
atgccattgg gaatggagag taaagcaata tcagatgcac agattactgc ttcatcctac   3960
tttaccaata tgtttgccac ctggtctcct tcaaaagctc gacttcacct ccaagggagg   4020
agtaatgcct ggagacctca ggtgaataat ccaaaagagt ggctgcaagt ggacttccag   4080
aagacaatga agtcacagg agtaactact cagggagtaa aatctctgct taccagcatg    4140
tatgtgaagg agttcctcat ctccagcagt caagatggcc atcagtggac tctcttttt    4200 cagaatggca aagtaaaggt ttttcaggga aatcaagact ccttcacacc tgtggtgaac   4260
tctctagacc caccgttact gactcgctac cttcgaattc accccagag ttgggtgcac    4320 cagattgccc tgaggatgga ggttctgggc tgcgaggcac aggacctcta cgacaaaact   4380
cacacatgcc caccgtgccc agctccgaa ctcctgggcg gaccgtcagt cttcctcttc     4440 ccccccaaaac ccaaggacac cctcatgatc tcccggaccc ctgaggtcac atgcgtggtg   4500
gtggacgtga gccacgaaga ccctgaggtc aagttcaact ggtacgtgga cggcgtggag   4560
gtgcataatg ccaagacaaa gccgcgggag gagcagtaca acagcacgta ccgtgtggtc   4620
agcgtcctca ccgtcctgca ccaggactgg ctgaatggca aggagtacaa gtgcaaggtc   4680
tccaacaaag ccctcccagc ccccatcgag aaaaccatct ccaaagccaa agggcagccc   4740
cgagaaccac aggtgtacac cctgccccca tcccgggatg agctgaccaa gaaccaggtc   4800
agcctgacct gcctggtcaa aggcttctat cccagcgaca tcgccgtgga gtgggagagc   4860
aatgggcagc cggagaacaa ctacaagacc acgcctcccg tgttggactc cgacggctcc   4920
ttcttcctct acagcaagct caccgtggac aagagcaggt ggcagcaggg gaacgtcttc   4980
tcatgctccg tgatgcatga ggctctgcac aaccactaca cgcagaagag cctctccctg   5040
tctccgggta aa                                                        5052

<210> SEQ ID NO 6
<211> LENGTH: 1684
<212> TYPE: PRT
<213> ORGANISM: Artificial Sequence
<220> FEATURE:
<223> OTHER INFORMATION: B domain deleted FVIII-Fc chain
<220> FEATURE:
<221> NAME/KEY: SIGNAL
<222> LOCATION: (1)..(19)
<223> OTHER INFORMATION: FVIII signal peptide
```

```
<220> FEATURE:
<221> NAME/KEY: MISC_FEATURE
<222> LOCATION: (20)..(759)
<223> OTHER INFORMATION: HC sequence
<220> FEATURE:
<221> NAME/KEY: DOMAIN
<222> LOCATION: (760)..(773)
<223> OTHER INFORMATION: remaining B domain sequence
<220> FEATURE:
<221> NAME/KEY: MISC_FEATURE
<222> LOCATION: (1458)..(1684)
<223> OTHER INFORMATION: Fc sequence

<400> SEQUENCE: 6
```

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro

```
                340             345             350
Gln Leu Arg Met Lys Asn Asn Glu Glu Ala Glu Asp Tyr Asp Asp Asp
            355                 360                 365
Leu Thr Asp Ser Glu Met Asp Val Val Arg Phe Asp Asp Asn Ser
    370                 375                 380
Pro Ser Phe Ile Gln Ile Arg Ser Val Ala Lys Lys His Pro Lys Thr
385                 390                 395                 400
Trp Val His Tyr Ile Ala Ala Glu Glu Asp Trp Asp Tyr Ala Pro
                405                 410                 415
Leu Val Leu Ala Pro Asp Asp Arg Ser Tyr Lys Ser Gln Tyr Leu Asn
            420                 425                 430
Asn Gly Pro Gln Arg Ile Gly Arg Lys Tyr Lys Val Arg Phe Met
        435                 440                 445
Ala Tyr Thr Asp Glu Thr Phe Lys Thr Arg Glu Ala Ile Gln His Glu
    450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Pro Pro Val Leu
        755                 760                 765
```

```
Lys Arg His Gln Arg Glu Ile Thr Arg Thr Thr Leu Gln Ser Asp Gln
    770                 775                 780

Glu Glu Ile Asp Tyr Asp Thr Ile Ser Val Glu Met Lys Lys Glu
785                 790                 795                 800

Asp Phe Asp Ile Tyr Asp Glu Asp Glu Asn Gln Ser Pro Arg Ser Phe
                    805                 810                 815

Gln Lys Lys Thr Arg His Tyr Phe Ile Ala Ala Val Glu Arg Leu Trp
                820                 825                 830

Asp Tyr Gly Met Ser Ser Ser Pro His Val Leu Arg Asn Arg Ala Gln
                835                 840                 845

Ser Gly Ser Val Pro Gln Phe Lys Lys Val Val Phe Gln Glu Phe Thr
    850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
                885                 890                 895

Met Val Thr Phe Arg Asn Gln Ala Ser Arg Pro Tyr Ser Phe Tyr Ser
                900                 905                 910

Ser Leu Ile Ser Tyr Glu Glu Asp Gln Arg Gln Gly Ala Glu Pro Arg
    915                 920                 925

Lys Asn Phe Val Lys Pro Asn Glu Thr Lys Thr Tyr Phe Trp Lys Val
    930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
                965                 970                 975

Ile Gly Pro Leu Leu Val Cys His Thr Asn Thr Leu Asn Pro Ala His
                980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170
```

```
Lys Leu Ala Arg Leu His Tyr Ser Gly Ser Ile Asn Ala Trp Ser
1175                1180                1185

Thr Lys Glu Pro Phe Ser Trp Ile Lys Val Asp Leu Leu Ala Pro
1190                1195                1200

Met Ile Ile His Gly Ile Lys Thr Gln Gly Ala Arg Gln Lys Phe
1205                1210                1215

Ser Ser Leu Tyr Ile Ser Gln Phe Ile Ile Met Tyr Ser Leu Asp
1220                1225                1230

Gly Lys Lys Trp Gln Thr Tyr Arg Gly Asn Ser Thr Gly Thr Leu
1235                1240                1245

Met Val Phe Phe Gly Asn Val Asp Ser Ser Gly Ile Lys His Asn
1250                1255                1260

Ile Phe Asn Pro Pro Ile Ile Ala Arg Tyr Ile Arg Leu His Pro
1265                1270                1275

Thr His Tyr Ser Ile Arg Ser Thr Leu Arg Met Glu Leu Met Gly
1280                1285                1290

Cys Asp Leu Asn Ser Cys Ser Met Pro Leu Gly Met Glu Ser Lys
1295                1300                1305

Ala Ile Ser Asp Ala Gln Ile Thr Ala Ser Ser Tyr Phe Thr Asn
1310                1315                1320

Met Phe Ala Thr Trp Ser Pro Ser Lys Ala Arg Leu His Leu Gln
1325                1330                1335

Gly Arg Ser Asn Ala Trp Arg Pro Gln Val Asn Asn Pro Lys Glu
1340                1345                1350

Trp Leu Gln Val Asp Phe Gln Lys Thr Met Lys Val Thr Gly Val
1355                1360                1365

Thr Thr Gln Gly Val Lys Ser Leu Leu Thr Ser Met Tyr Val Lys
1370                1375                1380

Glu Phe Leu Ile Ser Ser Ser Gln Asp Gly His Gln Trp Thr Leu
1385                1390                1395

Phe Phe Gln Asn Gly Lys Val Lys Val Phe Gln Gly Asn Gln Asp
1400                1405                1410

Ser Phe Thr Pro Val Val Asn Ser Leu Asp Pro Pro Leu Leu Thr
1415                1420                1425

Arg Tyr Leu Arg Ile His Pro Gln Ser Trp Val His Gln Ile Ala
1430                1435                1440

Leu Arg Met Glu Val Leu Gly Cys Glu Ala Gln Asp Leu Tyr Asp
1445                1450                1455

Lys Thr His Thr Cys Pro Pro Cys Pro Ala Pro Glu Leu Leu Gly
1460                1465                1470

Gly Pro Ser Val Phe Leu Phe Pro Pro Lys Pro Lys Asp Thr Leu
1475                1480                1485

Met Ile Ser Arg Thr Pro Glu Val Thr Cys Val Val Val Asp Val
1490                1495                1500

Ser His Glu Asp Pro Glu Val Lys Phe Asn Trp Tyr Val Asp Gly
1505                1510                1515

Val Glu Val His Asn Ala Lys Thr Lys Pro Arg Glu Glu Gln Tyr
1520                1525                1530

Asn Ser Thr Tyr Arg Val Val Ser Val Leu Thr Val Leu His Gln
1535                1540                1545

Asp Trp Leu Asn Gly Lys Glu Tyr Lys Cys Lys Val Ser Asn Lys
1550                1555                1560

Ala Leu Pro Ala Pro Ile Glu Lys Thr Ile Ser Lys Ala Lys Gly
```

```
                 1565                1570                1575
Gln Pro Arg Glu Pro Gln Val Tyr Thr Leu Pro Pro Ser Arg Asp
    1580                1585                1590
Glu Leu Thr Lys Asn Gln Val Ser Leu Thr Cys Leu Val Lys Gly
    1595                1600                1605
Phe Tyr Pro Ser Asp Ile Ala Val Glu Trp Glu Ser Asn Gly Gln
    1610                1615                1620
Pro Glu Asn Asn Tyr Lys Thr Thr Pro Pro Val Leu Asp Ser Asp
    1625                1630                1635
Gly Ser Phe Phe Leu Tyr Ser Lys Leu Thr Val Asp Lys Ser Arg
    1640                1645                1650
Trp Gln Gln Gly Asn Val Phe Ser Cys Ser Val Met His Glu Ala
    1655                1660                1665
Leu His Asn His Tyr Thr Gln Lys Ser Leu Ser Leu Ser Pro Gly
    1670                1675                1680
Lys

<210> SEQ ID NO 7
<211> LENGTH: 7734
<212> TYPE: DNA
<213> ORGANISM: Artificial Sequence
<220> FEATURE:
<223> OTHER INFORMATION: Full-length FVIIIFc
<220> FEATURE:
<221> NAME/KEY: sig_peptide
<222> LOCATION: (1)..(57)
<223> OTHER INFORMATION: FVIII signal peptide
<220> FEATURE:
<221> NAME/KEY: misc_feature
<222> LOCATION: (7054)..(7734)
<223> OTHER INFORMATION: Fc region

<400> SEQUENCE: 7
atgcaaatag agctctccac ctgcttcttt ctgtgccttt tgcgattctg ctttagtgcc      60
accagaagat actacctggg tgcagtggaa ctgtcatggg actatatgca aagtgatctc     120
ggtgagctgc ctgtggacgc aagatttcct cctagagtgc aaaatcttt tccattcaac      180
acctcagtcg tgtacaaaaa gactctgttt gtagaattca cggatcacct tttcaacatc     240
gctaagccaa ggccaccctg gatgggtctg ctaggtccta ccatccaggc tgaggtttat     300
gatacagtgg tcattacact taagaacatg gcttcccatc ctgtcagtct tcatgctgtt     360
ggtgtatcct actggaaagc ttctgaggga gctgaatatg atgatcagac cagtcaaagg     420
gagaaagaag atgataaagt cttccctggt ggaagccata catatgtctg gcaggtcctg     480
aaagagaatg gtccaatggc ctctgaccca ctgtgcctta cctactcata tctttctcat     540
gtggacctgg taaagacttt gaattcaggc ctcattggag ccctactagt atgtagagaa     600
gggagtctgg ccaaggaaaa gacacagacc ttgcacaaat ttatactact ttttgctgta     660
tttgatgaag ggaaaagttg gcactcagaa acaaagaact ccttgatgca ggataggga      720
gctgcatctg ctcgggcctg gcctaaaatg cacacagtca atggttatgt aaacaggtct     780
ctgccaggtc tgattggatg ccacaggaaa tcagtctatt ggcatgtgat tggaatgggc     840
accactcctg aagtgcactc aatattcctc gaaggtcaca catttcttgt gaggaaccat     900
cgccaggcgt ccttggaaat tcgccaata actttcctta ctgctcaaac actcttgatg     960
gaccttggac agtttctact gttttgtcat atctcttccc accaacatga tggcatggaa    1020
gcttatgtca aagtagacag ctgtccagag gaaccccaac tacgaatgaa aaataatgaa    1080
```

```
gaagcggaag actatgatga tgatcttact gattctgaaa tggatgtggt caggtttgat    1140
gatgacaact ctccttcctt tatccaaatt cgctcagttg ccaagaagca tcctaaaact    1200
tgggtacatt acattgctgc tgaagaggag gactgggact atgctccctt agtcctcgcc    1260
cccgatgaca gaagttataa aagtcaatat ttgaacaatg ccctcagcg gattggtagg     1320 aagtacaaaa aagtccgatt tatggcatac acagatgaaa cctttaagac tcgtgaagct    1380
attcagcatg aatcaggaat cttgggacct ttactttatg gggaagttgg agacacactg    1440
ttgattatat ttaagaatca agcaagcaga ccatataaca tctaccctca cggaatcact    1500
gatgtccgtc ctttgtattc aaggagatta ccaaaaggtg taaaacattt gaaggatttt    1560
ccaattctgc caggagaaat attcaaatat aaatggacag tgactgtaga agatgggcca    1620
actaaatcag atcctcggtg cctgacccgc tattactcta gtttcgttaa tatggagaga    1680
gatctagctt caggactcat tggccctctc ctcatctgct acaaagaatc tgtagatcaa    1740
agaggaaacc agataatgtc agacaagagg aatgtcatcc tgttttctgt atttgatgag    1800
aaccgaagct ggtacctcac agagaatata caacgctttc tccccaatcc agctggagtg    1860
cagcttgagg atccagagtt ccaagcctcc aacatcatgc acagcatcaa tggctatgtt    1920
tttgatagtt tgcagttgtc agtttgtttg catgaggtgg catactggta cattctaagc    1980
attggagcac agactgactt cctttctgtc ttcttctctg gatataccct caaacacaaa    2040
atggtctatg aagacacact caccctattc ccattctcag gagaaactgt cttcatgtcg    2100
atggaaaacc caggtctatg gattctgggg tgccacaact cagactttcg gaacagaggc    2160
atgaccgcct tactgaaggt ttctagttgt gacaagaaca ctggtgatta ttacgaggac    2220
agttatgaag atatttcagc atacttgctg agtaaaaaca atgccattga accaagaagc    2280
ttctcccaga attcaagaca ccctagcact aggcaaaagc aatttaatgc caccacaatt    2340
ccagaaaatg acatagagaa gactgacccc tggtttgcac acagaacacc tatgcctaaa    2400
atacaaaatg tctcctctag tgatttgttg atgctcttgc gacagagtcc tactccacat    2460
gggctatcct tatctgatct ccaagaagcc aaatatgaga cttttctga tgatccatca    2520 cctggagcaa tagacagtaa taacagcctg tctgaaatga cacacttcag gccacagctc    2580
catcacagtg gggacatggt atttaccccct gagtcaggcc tccaattaag attaaatgag    2640
aaactgggga caactgcagc aacagagttg aagaaacttg atttcaaagt ttctagtaca    2700
tcaaataatc tgatttcaac aattccatca gacaatttgg cagcaggtac tgataataca    2760
agttccttag acccccaag tatgccagtt cattatgata gtcaattaga taccactcta    2820
tttggcaaaa agtcatctcc ccttactgag tctggtggac ctctgagctt gagtgaagaa    2880
aataatgatt caaagttgtt agaatcaggt ttaatgaata gccaagaaag ttcatgggga    2940
aaaaatgtat cgtcaacaga gagtggtagg ttatttaaag ggaaaagagc tcatggacct    3000
gctttgttga ctaaagataa tgccttattc aaagttagca tctctttgtt aaagacaaac    3060
aaaacttcca ataattcagc aactaataga aagactcaca ttgatggccc atcattatta    3120
attgagaata gtccatcagt ctggcaaaat atattagaaa gtgacactga gtttaaaaaa    3180
gtgacacctt tgattcatga cagaatgctt atggacaaaa atgctacagc tttgaggcta    3240
aatcatatgt caaataaaac tacttcatca aaaacatgg aaatggtcca acagaaaaaa    3300 gagggccca ttccaccaga tgcacaaaat ccagatatgt cgttctttaa gatgctattc    3360
ttgccagaat cagcaaggtg gatacaaagg actcatggaa agaactctct gaactctggg    3420
caaggcccca gtccaaagca attagtatcc ttaggaccag aaaaatctgt ggaaggtcag    3480
```

```
aatttcttgt ctgagaaaaa caaagtggta gtaggaaagg gtgaatttac aaaggacgta      3540
ggactcaaag agatggtttt tccaagcagc agaaacctat ttcttactaa cttggataat      3600
ttacatgaaa ataatacaca caatcaagaa aaaaaaattc aggaagaaat agaaagaag       3660 gaaacattaa tccaagagaa tgtagttttg cctcagatac atacagtgac tggcactaag      3720
aatttcatga agaacctttt cttactgagc actaggcaaa atgtagaagg ttcatatgac      3780
ggggcatatg ctccagtact tcaagatttt aggtcattaa atgattcaac aaatagaaca      3840
aagaaacaca cagctcattt ctcaaaaaaa ggggaggaag aaaacttgga aggcttggga      3900
aatcaaacca agcaaattgt agagaaatat gcatgcacca caaggatatc tcctaataca      3960
agccagcaga attttgtcac gcaacgtagt aagagagctt tgaaacaatt cagactccca      4020
ctagaagaaa cagaacttga aaaaggata attgtggatg acacctcaac ccagtggtcc       4080
aaaaacatga acatttgac cccgagcacc ctcacacaga tagactacaa tgagaaggag       4140
aaaggggcca ttactcagtc tcccttatca gattgcctta cgaggagtca tagcatccct      4200
caagcaaata gatctccatt acccattgca aaggtatcat catttccatc tattagacct      4260
atatatctga ccagggtcct attccaagac aactcttctc atcttccagc agcatcttat      4320
agaaagaaag attctggggt ccaagaaagc agtcatttct acaaggagc caaaaaaat       4380 aacctttctt tagccattct aaccttggag atgactggtg atcaaagaga ggttggctcc      4440
ctggggacaa gtgccacaaa ttcagtcaca tacaagaaag ttgagaacac tgttctcccg      4500
aaaccagact tgcccaaaac atctggcaaa gttgaattgc ttccaaaagt tcacatttat      4560
cagaaggacc tattccctac ggaaactagc aatgggtctc ctggccatct ggatctcgtg      4620
gaagggagcc ttcttcaggg aacagaggga gcgattaagt ggaatgaagc aaacagacct      4680
ggaaaagttc cctttctgag agtagcaaca gaaagctctg caaagactcc ctccaagcta      4740
ttggatcctc ttgcttggga taaccactat ggtactcaga taccaaaaga agagtggaaa     4800
tcccaagaga agtcaccaga aaaaacagct tttaagaaaa aggataccat tttgtccctg      4860
aacgcttgtg aaagcaatca tgcaatagca gcaataaatg agggacaaaa taagcccgaa      4920
atagaagtca cctgggcaaa gcaaggtagg actgaaaggc tgtgctctca aaacccacca      4980
gtcttgaaac gccatcaacg ggaaataact cgtactactc ttcagtcaga tcaagaggaa      5040
attgactatg atgataccat atcagttgaa atgaagaagg aagattttga catttatgat      5100
gaggatgaaa atcagagccc ccgcagcttt caaaagaaaa cacgacacta ttttattgct      5160
gcagtggaga ggctctggga ttatgggatg agtagctccc cacatgttct aagaaacagg      5220
gctcagagtg gcagtgtccc tcagttcaag aaagttgttt tccaggaatt tactgatggc      5280
tcctttactc agcccttata ccgtggagaa ctaaatgaac atttgggact cctgggcca       5340 tatataagag cagaagttga agataatatc atggtaactt tcagaaatca ggcctctcgt      5400
ccctattcct tctattctag cttatttct tatgaggaag atcagaggca aggagcagaa       5460
cctagaaaaa actttgtcaa gcctaatgaa accaaaactt acttttggaa agtgcaacat      5520
catatggcac ccactaaaga tgagtttgac tgcaaagcct gggcttattt ctctgatgtt      5580
gacctggaaa agatgtgca ctcaggcctg attggacccc ttctggtctg ccacactaac        5640
acactgaacc ctgctcatgg gagacaagtg acagtacagg aatttgctct gttttttcacc     5700 atctttgatg agaccaaaag ctggtacttc actgaaaata tggaaagaaa ctgcagggct      5760
ccctgcaata tccagatgga agatcccact tttaaagaga attatcgctt ccatgcaatc      5820
```

```
aatggctaca taatggatac actacctggc ttagtaatgg ctcaggatca aaggattcga   5880
tggtatctgc tcagcatggg cagcaatgaa acatccatt ctattcattt cagtggacat   5940
gtgttcactg tacgaaaaaa agaggagtat aaaatggcac tgtacaatct ctatccaggt   6000 gttttttgaga cagtggaaat gttaccatcc aaagctggaa tttggcgggt ggaatgcctt   6060
attggcgagc atctacatgc tgggatgagc acactttttc tggtgtacag caataagtgt   6120
cagactcccc tgggaatggc ttctggacac attagagatt ttcagattac agcttcagga   6180
caatatggac agtgggcccc aaagctggcc agacttcatt attccggatc aatcaatgcc   6240
tggagcacca aggagccctt ttcttggatc aaggtggatc tgttggcacc aatgattatt   6300
cacggcatca agacccaggg tgcccgtcag aagttctcca gcctctacat ctctcagttt   6360
atcatcatgt atagtcttga tgggaagaag tggcagactt atcgaggaaa ttccactgga   6420
accttaatgg tcttctttgg caatgtggat tcatctggga taaaacacaa tattttaac   6480 cctccaatta ttgctcgata catccgtttg cacccaactc attatagcat tcgcagcact   6540
cttcgcatgg agttgatggg ctgtgattta aatagttgca gcatgccatt gggaatggag   6600
agtaaagcaa tatcagatgc acagattact gcttcatcct actttaccaa tatgtttgcc   6660
acctggtctc cttcaaaagc tcgacttcac ctccaaggga ggagtaatgc ctggagacct   6720
caggtgaata tccaaaagaa gtggctgcaa gtggacttcc agaagacaat gaaagtcaca   6780
ggagtaacta ctcagggagt aaaatctctg cttaccagca tgtatgtgaa ggagttcctc   6840
atctccagca gtcaagatgg ccatcagtgg actctctttt ttcagaatgg caaagtaaag   6900 gttttttcagg gaaatcaaga ctccttcaca cctgtggtga actctctaga cccaccgtta   6960
ctgactcgct accttcgaat tcaccccag agttgggtgc accagattgc cctgaggatg   7020
gaggttctgg gctgcgaggc acaggacctc tacgacaaaa ctcacacatg cccaccgtgc   7080
ccagctccag aactcctggg cggaccgtca gtcttcctct tccccccaaa acccaaggac   7140
accctcatga tctcccggac ccctgaggtc acatgcgtgg tggtggacgt gagccacgaa   7200
gaccctgagg tcaagttcaa ctggtacgtg gacggcgtgg aggtgcataa tgccaagaca   7260
aagccgcggg aggagcagta caacagcacg taccgtgtgg tcagcgtcct caccgtcctg   7320
caccaggact ggctgaatgg caaggagtac aagtgcaagg tctccaacaa agccctccca   7380
gcccccatcg agaaaaccat ctccaaagcc aaagggcagc cccgagaacc acaggtgtac   7440
accctgcccc catcccggga tgagctgacc aagaaccagg tcagcctgac ctgcctggtc   7500
aaaggcttct atcccagcga catcgccgtg gagtgggaga gcaatgggca gccggagaac   7560
aactacaaga ccacgcctcc cgtgttggac tccgacggct ccttcttcct ctacagcaag   7620
ctcaccgtgg acaagagcag gtggcagcag gggaacgtct tctcatgctc cgtgatgcat   7680
gaggctctgc acaaccacta cacgcagaag agcctctccc tgtctccggg taaa       7734
```

<210> SEQ ID NO 8
<211> LENGTH: 2578
<212> TYPE: PRT
<213> ORGANISM: Artificial Sequence
<220> FEATURE:
<223> OTHER INFORMATION: Full-length FVIIIFc chain
<220> FEATURE:
<221> NAME/KEY: SIGNAL
<222> LOCATION: (1)..(19)
<223> OTHER INFORMATION: FVIII signal peptide
<220> FEATURE:
<221> NAME/KEY: MISC_FEATURE
<222> LOCATION: (20)..(759)
<223> OTHER INFORMATION: Hc sequence -continued

```
<220> FEATURE:
<221> NAME/KEY: DOMAIN
<222> LOCATION: (760)..(1667)
<223> OTHER INFORMATION: B domain sequence
<220> FEATURE:
<221> NAME/KEY: MISC_FEATURE
<222> LOCATION: (2352)..(2578)
<223> OTHER INFORMATION: Fc region

<400> SEQUENCE: 8

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365
```

-continued

```
Leu Thr Asp Ser Glu Met Asp Val Val Arg Phe Asp Asp Asn Ser
        370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                    405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
            435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
            515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
    610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
    690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
        755                 760                 765

Ser Thr Arg Gln Lys Gln Phe Asn Ala Thr Thr Ile Pro Glu Asn Asp
    770                 775                 780
```

```
Ile Glu Lys Thr Asp Pro Trp Phe Ala His Arg Thr Pro Met Pro Lys
785                 790                 795                 800

Ile Gln Asn Val Ser Ser Ser Asp Leu Leu Met Leu Leu Arg Gln Ser
            805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
        835                 840                 845

Ser Leu Ser Glu Met Thr His Phe Arg Pro Gln Leu His His Ser Gly
    850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
            900                 905                 910

Leu Ala Ala Gly Thr Asp Asn Thr Ser Ser Leu Gly Pro Pro Ser Met
        915                 920                 925

Pro Val His Tyr Asp Ser Gln Leu Asp Thr Thr Leu Phe Gly Lys Lys
    930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
        995                 1000                1005

Leu Phe Lys Val Ser Ile Ser Leu Leu Lys Thr Asn Lys Thr Ser
    1010                1015                1020

Asn Asn Ser Ala Thr Asn Arg Lys Thr His Ile Asp Gly Pro Ser
    1025                1030                1035

Leu Leu Ile Glu Asn Ser Pro Ser Val Trp Gln Asn Ile Leu Glu
    1040                1045                1050

Ser Asp Thr Glu Phe Lys Lys Val Thr Pro Leu Ile His Asp Arg
    1055                1060                1065

Met Leu Met Asp Lys Asn Ala Thr Ala Leu Arg Leu Asn His Met
    1070                1075                1080

Ser Asn Lys Thr Thr Ser Ser Lys Asn Met Glu Met Val Gln Gln
    1085                1090                1095

Lys Lys Glu Gly Pro Ile Pro Pro Asp Ala Gln Asn Pro Asp Met
    1100                1105                1110

Ser Phe Phe Lys Met Leu Phe Leu Pro Glu Ser Ala Arg Trp Ile
    1115                1120                1125

Gln Arg Thr His Gly Lys Asn Ser Leu Asn Ser Gly Gln Gly Pro
    1130                1135                1140

Ser Pro Lys Gln Leu Val Ser Leu Gly Pro Glu Lys Ser Val Glu
    1145                1150                1155

Gly Gln Asn Phe Leu Ser Glu Lys Asn Lys Val Val Val Gly Lys
    1160                1165                1170

Gly Glu Phe Thr Lys Asp Val Gly Leu Lys Glu Met Val Phe Pro
    1175                1180                1185

Ser Ser Arg Asn Leu Phe Leu Thr Asn Leu Asp Asn Leu His Glu
```

-continued

```
            1190                1195                1200
Asn Asn Thr His Asn Gln Glu Lys Lys Ile Gln Glu Glu Ile Glu
            1205                1210                1215
Lys Lys Glu Thr Leu Ile Gln Glu Asn Val Val Leu Pro Gln Ile
            1220                1225                1230
His Thr Val Thr Gly Thr Lys Asn Phe Met Lys Asn Leu Phe Leu
            1235                1240                1245
Leu Ser Thr Arg Gln Asn Val Glu Gly Ser Tyr Asp Gly Ala Tyr
            1250                1255                1260
Ala Pro Val Leu Gln Asp Phe Arg Ser Leu Asn Asp Ser Thr Asn
            1265                1270                1275
Arg Thr Lys Lys His Thr Ala His Phe Ser Lys Lys Gly Glu Glu
            1280                1285                1290
Glu Asn Leu Glu Gly Leu Gly Asn Gln Thr Lys Gln Ile Val Glu
            1295                1300                1305
Lys Tyr Ala Cys Thr Thr Arg Ile Ser Pro Asn Thr Ser Gln Gln
            1310                1315                1320
Asn Phe Val Thr Gln Arg Ser Lys Arg Ala Leu Lys Gln Phe Arg
            1325                1330                1335
Leu Pro Leu Glu Glu Thr Glu Leu Glu Lys Arg Ile Ile Val Asp
            1340                1345                1350
Asp Thr Ser Thr Gln Trp Ser Lys Asn Met Lys His Leu Thr Pro
            1355                1360                1365
Ser Thr Leu Thr Gln Ile Asp Tyr Asn Glu Lys Glu Lys Gly Ala
            1370                1375                1380
Ile Thr Gln Ser Pro Leu Ser Asp Cys Leu Thr Arg Ser His Ser
            1385                1390                1395
Ile Pro Gln Ala Asn Arg Ser Pro Leu Pro Ile Ala Lys Val Ser
            1400                1405                1410
Ser Phe Pro Ser Ile Arg Pro Ile Tyr Leu Thr Arg Val Leu Phe
            1415                1420                1425
Gln Asp Asn Ser Ser His Leu Pro Ala Ala Ser Tyr Arg Lys Lys
            1430                1435                1440
Asp Ser Gly Val Gln Glu Ser Ser His Phe Leu Gln Gly Ala Lys
            1445                1450                1455
Lys Asn Asn Leu Ser Leu Ala Ile Leu Thr Leu Glu Met Thr Gly
            1460                1465                1470
Asp Gln Arg Glu Val Gly Ser Leu Gly Thr Ser Ala Thr Asn Ser
            1475                1480                1485
Val Thr Tyr Lys Lys Val Glu Asn Thr Val Leu Pro Lys Pro Asp
            1490                1495                1500
Leu Pro Lys Thr Ser Gly Lys Val Glu Leu Leu Pro Lys Val His
            1505                1510                1515
Ile Tyr Gln Lys Asp Leu Phe Pro Thr Glu Thr Ser Asn Gly Ser
            1520                1525                1530
Pro Gly His Leu Asp Leu Val Glu Gly Ser Leu Leu Gln Gly Thr
            1535                1540                1545
Glu Gly Ala Ile Lys Trp Asn Glu Ala Asn Arg Pro Gly Lys Val
            1550                1555                1560
Pro Phe Leu Arg Val Ala Thr Glu Ser Ser Ala Lys Thr Pro Ser
            1565                1570                1575
Lys Leu Leu Asp Pro Leu Ala Trp Asp Asn His Tyr Gly Thr Gln
            1580                1585                1590
```

```
Ile Pro Lys Glu Glu Trp Lys Ser Gln Glu Lys Ser Pro Glu Lys
1595                1600                1605

Thr Ala Phe Lys Lys Lys Asp Thr Ile Leu Ser Leu Asn Ala Cys
1610                1615                1620

Glu Ser Asn His Ala Ile Ala Ile Asn Glu Gly Gln Asn Lys
1625                1630                1635

Pro Glu Ile Glu Val Thr Trp Ala Lys Gln Gly Arg Thr Glu Arg
1640                1645                1650

Leu Cys Ser Gln Asn Pro Pro Val Leu Lys Arg His Gln Arg Glu
1655                1660                1665

Ile Thr Arg Thr Thr Leu Gln Ser Asp Gln Glu Glu Ile Asp Tyr
1670                1675                1680

Asp Asp Thr Ile Ser Val Glu Met Lys Lys Glu Asp Phe Asp Ile
1685                1690                1695

Tyr Asp Glu Asp Glu Asn Gln Ser Pro Arg Ser Phe Gln Lys Lys
1700                1705                1710

Thr Arg His Tyr Phe Ile Ala Ala Val Glu Arg Leu Trp Asp Tyr
1715                1720                1725

Gly Met Ser Ser Ser Pro His Val Leu Arg Asn Arg Ala Gln Ser
1730                1735                1740

Gly Ser Val Pro Gln Phe Lys Lys Val Val Phe Gln Glu Phe Thr
1745                1750                1755

Asp Gly Ser Phe Thr Gln Pro Leu Tyr Arg Gly Glu Leu Asn Glu
1760                1765                1770

His Leu Gly Leu Leu Gly Pro Tyr Ile Arg Ala Glu Val Glu Asp
1775                1780                1785

Asn Ile Met Val Thr Phe Arg Asn Gln Ala Ser Arg Pro Tyr Ser
1790                1795                1800

Phe Tyr Ser Ser Leu Ile Ser Tyr Glu Glu Asp Gln Arg Gln Gly
1805                1810                1815

Ala Glu Pro Arg Lys Asn Phe Val Lys Pro Asn Glu Thr Lys Thr
1820                1825                1830

Tyr Phe Trp Lys Val Gln His His Met Ala Pro Thr Lys Asp Glu
1835                1840                1845

Phe Asp Cys Lys Ala Trp Ala Tyr Phe Ser Asp Val Asp Leu Glu
1850                1855                1860

Lys Asp Val His Ser Gly Leu Ile Gly Pro Leu Leu Val Cys His
1865                1870                1875

Thr Asn Thr Leu Asn Pro Ala His Gly Arg Gln Val Thr Val Gln
1880                1885                1890

Glu Phe Ala Leu Phe Phe Thr Ile Phe Asp Glu Thr Lys Ser Trp
1895                1900                1905

Tyr Phe Thr Glu Asn Met Glu Arg Asn Cys Arg Ala Pro Cys Asn
1910                1915                1920

Ile Gln Met Glu Asp Pro Thr Phe Lys Glu Asn Tyr Arg Phe His
1925                1930                1935

Ala Ile Asn Gly Tyr Ile Met Asp Thr Leu Pro Gly Leu Val Met
1940                1945                1950

Ala Gln Asp Gln Arg Ile Arg Trp Tyr Leu Leu Ser Met Gly Ser
1955                1960                1965

Asn Glu Asn Ile His Ser Ile His Phe Ser Gly His Val Phe Thr
1970                1975                1980
```

-continued

| | | | | | | | | | | | |
|---|---|---|---|---|---|---|---|---|---|---|---|
|Val|Arg|Lys|Lys|Glu|Glu|Tyr|Lys|Met|Ala|Leu|Tyr|
| |1985| | | |1990| | | |1995| | |
|Asn|Leu|Tyr| | | | | | | | | |

Pro Gly Val Phe Glu Thr Val Glu Met Leu Pro Ser Lys Ala Gly
   2000              2005              2010

Ile Trp Arg Val Glu Cys Leu Ile Gly Glu His Leu His Ala Gly
   2015              2020              2025

Met Ser Thr Leu Phe Leu Val Tyr Ser Asn Lys Cys Gln Thr Pro
   2030              2035              2040

Leu Gly Met Ala Ser Gly His Ile Arg Asp Phe Gln Ile Thr Ala
   2045              2050              2055

Ser Gly Gln Tyr Gly Gln Trp Ala Pro Lys Leu Ala Arg Leu His
   2060              2065              2070

Tyr Ser Gly Ser Ile Asn Ala Trp Ser Thr Lys Glu Pro Phe Ser
   2075              2080              2085

Trp Ile Lys Val Asp Leu Leu Ala Pro Met Ile Ile His Gly Ile
   2090              2095              2100

Lys Thr Gln Gly Ala Arg Gln Lys Phe Ser Ser Leu Tyr Ile Ser
   2105              2110              2115

Gln Phe Ile Ile Met Tyr Ser Leu Asp Gly Lys Lys Trp Gln Thr
   2120              2125              2130

Tyr Arg Gly Asn Ser Thr Gly Thr Leu Met Val Phe Phe Gly Asn
   2135              2140              2145

Val Asp Ser Ser Gly Ile Lys His Asn Ile Phe Asn Pro Pro Ile
   2150              2155              2160

Ile Ala Arg Tyr Ile Arg Leu His Pro Thr His Tyr Ser Ile Arg
   2165              2170              2175

Ser Thr Leu Arg Met Glu Leu Met Gly Cys Asp Leu Asn Ser Cys
   2180              2185              2190

Ser Met Pro Leu Gly Met Glu Ser Lys Ala Ile Ser Asp Ala Gln
   2195              2200              2205

Ile Thr Ala Ser Ser Tyr Phe Thr Asn Met Phe Ala Thr Trp Ser
   2210              2215              2220

Pro Ser Lys Ala Arg Leu His Leu Gln Gly Arg Ser Asn Ala Trp
   2225              2230              2235

Arg Pro Gln Val Asn Asn Pro Lys Glu Trp Leu Gln Val Asp Phe
   2240              2245              2250

Gln Lys Thr Met Lys Val Thr Gly Val Thr Thr Gln Gly Val Lys
   2255              2260              2265

Ser Leu Leu Thr Ser Met Tyr Val Lys Glu Phe Leu Ile Ser Ser
   2270              2275              2280

Ser Gln Asp Gly His Gln Trp Thr Leu Phe Phe Gln Asn Gly Lys
   2285              2290              2295

Val Lys Val Phe Gln Gly Asn Gln Asp Ser Phe Thr Pro Val Val
   2300              2305              2310

Asn Ser Leu Asp Pro Pro Leu Leu Thr Arg Tyr Leu Arg Ile His
   2315              2320              2325

Pro Gln Ser Trp Val His Gln Ile Ala Leu Arg Met Glu Val Leu
   2330              2335              2340

Gly Cys Glu Ala Gln Asp Leu Tyr Asp Lys Thr His Thr Cys Pro
   2345              2350              2355

Pro Cys Pro Ala Pro Glu Leu Leu Gly Gly Pro Ser Val Phe Leu
   2360              2365              2370

Phe Pro Pro Lys Pro Lys Asp Thr Leu Met Ile Ser Arg Thr Pro

```
                2375                2380                2385

Glu Val Thr Cys Val Val Asp Val Ser His Glu Asp Pro Glu
        2390                2395                2400

Val Lys Phe Asn Trp Tyr Val Asp Gly Val Glu Val His Asn Ala
        2405                2410                2415

Lys Thr Lys Pro Arg Glu Glu Gln Tyr Asn Ser Thr Tyr Arg Val
        2420                2425                2430

Val Ser Val Leu Thr Val Leu His Gln Asp Trp Leu Asn Gly Lys
        2435                2440                2445

Glu Tyr Lys Cys Lys Val Ser Asn Lys Ala Leu Pro Ala Pro Ile
        2450                2455                2460

Glu Lys Thr Ile Ser Lys Ala Lys Gly Gln Pro Arg Glu Pro Gln
        2465                2470                2475

Val Tyr Thr Leu Pro Pro Ser Arg Asp Glu Leu Thr Lys Asn Gln
        2480                2485                2490

Val Ser Leu Thr Cys Leu Val Lys Gly Phe Tyr Pro Ser Asp Ile
        2495                2500                2505

Ala Val Glu Trp Glu Ser Asn Gly Gln Pro Glu Asn Asn Tyr Lys
        2510                2515                2520

Thr Thr Pro Pro Val Leu Asp Ser Asp Gly Ser Phe Phe Leu Tyr
        2525                2530                2535

Ser Lys Leu Thr Val Asp Lys Ser Arg Trp Gln Gln Gly Asn Val
        2540                2545                2550

Phe Ser Cys Ser Val Met His Glu Ala Leu His Asn His Tyr Thr
        2555                2560                2565

Gln Lys Ser Leu Ser Leu Ser Pro Gly Lys
        2570                2575

<210> SEQ ID NO 9
<211> LENGTH: 32
<212> TYPE: PRT
<213> ORGANISM: Homo sapiens
<220> FEATURE:
<221> NAME/KEY: MISC_FEATURE
<223> OTHER INFORMATION: CTP peptide 1

<400> SEQUENCE: 9

Asp Pro Arg Phe Gln Asp Ser Ser Ser Lys Ala Pro Pro Ser
1               5                   10                  15

Leu Pro Ser Pro Ser Arg Leu Pro Gly Pro Ser Asp Thr Pro Ile Leu
            20                  25                  30

<210> SEQ ID NO 10
<211> LENGTH: 28
<212> TYPE: PRT
<213> ORGANISM: Homo sapiens
<220> FEATURE:
<221> NAME/KEY: MISC_FEATURE
<223> OTHER INFORMATION: CTP peptide 2

<400> SEQUENCE: 10

Ser Ser Ser Ser Lys Ala Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 11
<211> LENGTH: 20
<212> TYPE: PRT
```

```
<213> ORGANISM: Artificial Sequence
<220> FEATURE:
<223> OTHER INFORMATION: PAS peptide 1

<400> SEQUENCE: 11

Ala Ser Pro Ala Ala Pro Ala Pro Ala Ser Pro Ala Ala Pro Ala Pro
1               5                   10                  15

Ser Ala Pro Ala
            20

<210> SEQ ID NO 12
<211> LENGTH: 20
<212> TYPE: PRT
<213> ORGANISM: Artificial Sequence
<220> FEATURE:
<223> OTHER INFORMATION: PAS peptide 2

<400> SEQUENCE: 12

Ala Ala Pro Ala Ser Pro Ala Pro Ala Ala Pro Ser Ala Pro Ala Pro
1               5                   10                  15

Ala Ala Pro Ser
            20

<210> SEQ ID NO 13
<211> LENGTH: 20
<212> TYPE: PRT
<213> ORGANISM: Artificial Sequence
<220> FEATURE:
<223> OTHER INFORMATION: PAS peptide 3

<400> SEQUENCE: 13

Ala Pro Ser Ser Pro Ser Pro Ser Ala Pro Ser Ser Pro Ser Pro Ala
1               5                   10                  15

Ser Pro Ser Ser
            20

<210> SEQ ID NO 14
<211> LENGTH: 19
<212> TYPE: PRT
<213> ORGANISM: Artificial Sequence
<220> FEATURE:
<223> OTHER INFORMATION: PAS peptide 4

<400> SEQUENCE: 14

Ala Pro Ser Ser Pro Ser Pro Ser Ala Pro Ser Ser Pro Ser Pro Ala
1               5                   10                  15

Ser Pro Ser

<210> SEQ ID NO 15
<211> LENGTH: 20
<212> TYPE: PRT
<213> ORGANISM: Artificial Sequence
<220> FEATURE:
<223> OTHER INFORMATION: PAS peptide 5

<400> SEQUENCE: 15

Ser Ser Pro Ser Ala Pro Ser Pro Ser Ser Pro Ala Ser Pro Ser Pro
1               5                   10                  15

Ser Ser Pro Ala
            20

<210> SEQ ID NO 16
<211> LENGTH: 24
<212> TYPE: PRT
```

```
<213> ORGANISM: Artificial Sequence
<220> FEATURE:
<223> OTHER INFORMATION: PAS peptide 6

<400> SEQUENCE: 16

Ala Ala Ser Pro Ala Ala Pro Ser Ala Pro Pro Ala Ala Ala Ser Pro
1               5                   10                  15

Ala Ala Pro Ser Ala Pro Pro Ala
            20

<210> SEQ ID NO 17
<211> LENGTH: 20
<212> TYPE: PRT
<213> ORGANISM: Artificial Sequence
<220> FEATURE:
<223> OTHER INFORMATION: PAS peptide 7

<400> SEQUENCE: 17

Ala Ser Ala Ala Ala Pro Ala Ala Ser Ala Ala Ala Ser Ala Pro
1               5                   10                  15

Ser Ala Ala Ala
            20

<210> SEQ ID NO 18
<211> LENGTH: 11
<212> TYPE: PRT
<213> ORGANISM: Artificial Sequence
<220> FEATURE:
<223> OTHER INFORMATION: Albumin Binding Peptide Core Sequence

<400> SEQUENCE: 18

Asp Ile Cys Leu Pro Arg Trp Gly Cys Leu Trp
1               5                   10

<210> SEQ ID NO 19
<211> LENGTH: 264
<212> TYPE: PRT
<213> ORGANISM: Artificial Sequence
<220> FEATURE:
<223> OTHER INFORMATION: GFP protein

<400> SEQUENCE: 19

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Gly Tyr Gly Val Gln Cys Phe Ala Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
```

```
                    145                 150                 155                 160

Ile Lys Val Asn Phe Lys Ile Arg His Asn Ile Glu Asp Gly Ser Val
                        165                 170                 175

Gln Leu Ala Asp His Tyr Gln Gln Asn Thr Pro Ile Gly Asp Gly Pro
                        180                 185                 190

Val Leu Leu Pro Asp Asn His Tyr Leu Ser Thr Gln Ser Ala Leu Ser
                        195                 200                 205

Lys Asp Pro Asn Glu Lys Arg Asp His Met Val Leu Leu Glu Phe Val
                    210                 215                 220

Thr Ala Ala Gly Ile Thr His Gly Met Asp Glu Leu Tyr Lys Ser Arg
        225                 230                 235                 240

Thr Ser Gly Ser Pro Gly Leu Gln Glu Phe Asp Ile Lys Leu Ile Asp
                        245                 250                 255

Thr Val Asp Leu Glu Ser Cys Asn
                        260

<210> SEQ ID NO 20
<211> LENGTH: 474
<212> TYPE: PRT
<213> ORGANISM: Artificial Sequence
<220> FEATURE:
<223> OTHER INFORMATION: Single-chain Human IgG1 Fc
<220> FEATURE:
<221> NAME/KEY: MISC_FEATURE
<222> LOCATION: (228)..(247)
<223> OTHER INFORMATION: Gly/Ser linker

<400> SEQUENCE: 20

Asp Lys Thr His Thr Cys Pro Pro Cys Pro Ala Pro Glu Leu Leu Gly
        1               5                   10                  15

Gly Pro Ser Val Phe Leu Phe Pro Pro Lys Pro Lys Asp Thr Leu Met
                        20                  25                  30

Ile Ser Arg Thr Pro Glu Val Thr Cys Val Val Val Asp Val Ser His
                        35                  40                  45

Glu Asp Pro Glu Val Lys Phe Asn Trp Tyr Val Asp Gly Val Glu Val
                    50                  55                  60

His Asn Ala Lys Thr Lys Pro Arg Glu Glu Gln Tyr Asn Ser Thr Tyr
        65                  70                  75                  80

Arg Val Val Ser Val Leu Thr Val Leu His Gln Asp Trp Leu Asn Gly
                        85                  90                  95

Lys Glu Tyr Lys Cys Lys Val Ser Asn Lys Ala Leu Pro Ala Pro Ile
                        100                 105                 110

Glu Lys Thr Ile Ser Lys Ala Lys Gly Gln Pro Arg Glu Pro Gln Val
                        115                 120                 125

Tyr Thr Leu Pro Pro Ser Arg Asp Glu Leu Thr Lys Asn Gln Val Ser
                    130                 135                 140

Leu Thr Cys Leu Val Lys Gly Phe Tyr Pro Ser Asp Ile Ala Val Glu
        145                 150                 155                 160

Trp Glu Ser Asn Gly Gln Pro Glu Asn Asn Tyr Lys Thr Thr Pro Pro
                        165                 170                 175

Val Leu Asp Ser Asp Gly Ser Phe Phe Leu Tyr Ser Lys Leu Thr Val
                        180                 185                 190

Asp Lys Ser Arg Trp Gln Gln Gly Asn Val Phe Ser Cys Ser Val Met
                        195                 200                 205

His Glu Ala Leu His Asn His Tyr Thr Gln Lys Ser Leu Ser Leu Ser
                    210                 215                 220
```

Pro Gly Lys Gly Gly Gly Ser Gly Gly Gly Ser Gly Gly Gly
225                 230                 235                 240

Gly Ser Gly Gly Gly Ser Asp Lys Thr His Thr Cys Pro Pro Cys
            245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
            325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
            405                 410                 415

Asn Tyr Lys Thr Thr Pro Pro Val Leu Asp Ser Asp Gly Ser Phe Phe
            420                 425                 430

Leu Tyr Ser Lys Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470

<210> SEQ ID NO 21
<211> LENGTH: 591
<212> TYPE: PRT
<213> ORGANISM: Homo sapiens
<220> FEATURE:
<221> NAME/KEY: MISC_FEATURE
<223> OTHER INFORMATION: Mature human albumin protein sequence

<400> SEQUENCE: 21

Arg Gly Val Phe Arg Arg Asp Ala His Lys Ser Glu Val Ala His Arg
1               5                   10                  15

Phe Lys Asp Leu Gly Glu Glu Asn Phe Lys Ala Leu Val Leu Ile Ala
            20                  25                  30

Phe Ala Gln Tyr Leu Gln Gln Cys Pro Phe Glu Asp His Val Lys Leu
        35                  40                  45

Val Asn Glu Val Thr Glu Phe Ala Lys Thr Cys Val Ala Asp Glu Ser
    50                  55                  60

Ala Glu Asn Cys Asp Lys Ser Leu His Thr Leu Phe Gly Asp Lys Leu
65                  70                  75                  80

Cys Thr Val Ala Thr Leu Arg Glu Thr Tyr Gly Glu Met Ala Asp Cys
                85                  90                  95

Cys Ala Lys Gln Glu Pro Glu Arg Asn Glu Cys Phe Leu Gln His Lys
            100                 105                 110

```
Asp Asp Asn Pro Asn Leu Pro Arg Leu Val Arg Pro Glu Val Asp Val
        115                 120                 125

Met Cys Thr Ala Phe His Asp Asn Glu Glu Thr Phe Leu Lys Lys Tyr
    130                 135                 140

Leu Tyr Glu Ile Ala Arg Arg His Pro Tyr Phe Tyr Ala Pro Glu Leu
145                 150                 155                 160

Leu Phe Phe Ala Lys Arg Tyr Lys Ala Ala Phe Thr Glu Cys Cys Gln
            165                 170                 175

Ala Ala Asp Lys Ala Ala Cys Leu Leu Pro Lys Leu Asp Glu Leu Arg
            180                 185                 190

Asp Glu Gly Lys Ala Ser Ser Ala Lys Gln Arg Leu Lys Cys Ala Ser
            195                 200                 205

Leu Gln Lys Phe Gly Glu Arg Ala Phe Lys Ala Trp Ala Val Ala Arg
            210                 215                 220

Leu Ser Gln Arg Phe Pro Lys Ala Glu Phe Ala Glu Val Ser Lys Leu
225                 230                 235                 240

Val Thr Asp Leu Thr Lys Val His Thr Glu Cys Cys His Gly Asp Leu
            245                 250                 255

Leu Glu Cys Ala Asp Asp Arg Ala Asp Leu Ala Lys Tyr Ile Cys Glu
            260                 265                 270

Asn Gln Asp Ser Ile Ser Ser Lys Leu Lys Glu Cys Cys Glu Lys Pro
            275                 280                 285

Leu Leu Glu Lys Ser His Cys Ile Ala Glu Val Glu Asn Asp Glu Met
            290                 295                 300

Pro Ala Asp Leu Pro Ser Leu Ala Ala Asp Phe Val Glu Ser Lys Asp
305                 310                 315                 320

Val Cys Lys Asn Tyr Ala Glu Ala Lys Asp Val Phe Leu Gly Met Phe
            325                 330                 335

Leu Tyr Glu Tyr Ala Arg Arg His Pro Asp Tyr Ser Val Val Leu Leu
            340                 345                 350

Leu Arg Leu Ala Lys Thr Tyr Glu Thr Thr Leu Glu Lys Cys Cys Ala
            355                 360                 365

Ala Ala Asp Pro His Glu Cys Tyr Ala Lys Val Phe Asp Glu Phe Lys
            370                 375                 380

Pro Leu Val Glu Glu Pro Gln Asn Leu Ile Lys Gln Asn Cys Glu Leu
385                 390                 395                 400

Phe Glu Gln Leu Gly Glu Tyr Lys Phe Gln Asn Ala Leu Leu Val Arg
            405                 410                 415

Tyr Thr Lys Lys Val Pro Gln Val Ser Thr Pro Thr Leu Val Glu Val
            420                 425                 430

Ser Arg Asn Leu Gly Lys Val Gly Ser Lys Cys Cys Lys His Pro Glu
            435                 440                 445

Ala Lys Arg Met Pro Cys Ala Glu Asp Tyr Leu Ser Val Val Leu Asn
450                 455                 460

Gln Leu Cys Val Leu His Glu Lys Thr Pro Val Ser Asp Arg Val Thr
465                 470                 475                 480

Lys Cys Cys Thr Glu Ser Leu Val Asn Arg Arg Pro Cys Phe Ser Ala
            485                 490                 495

Leu Glu Val Asp Glu Thr Tyr Val Pro Lys Glu Phe Asn Ala Glu Thr
            500                 505                 510

Phe Thr Phe His Ala Asp Ile Cys Thr Leu Ser Glu Lys Glu Arg Gln
            515                 520                 525
```

```
Ile Lys Lys Gln Thr Ala Leu Val Glu Leu Val Lys His Lys Pro Lys
    530                 535                 540
Ala Thr Lys Glu Gln Leu Lys Ala Val Met Asp Asp Phe Ala Ala Phe
545                 550                 555                 560
Val Glu Lys Cys Cys Lys Ala Asp Asp Lys Glu Thr Cys Phe Ala Glu
                565                 570                 575
Glu Gly Lys Lys Leu Val Ala Ala Ser Gln Ala Ala Leu Gly Leu
            580                 585                 590

<210> SEQ ID NO 22
<211> LENGTH: 18
<212> TYPE: PRT
<213> ORGANISM: Artificial Sequence
<220> FEATURE:
<223> OTHER INFORMATION: Albumin binding peptide 1

<400> SEQUENCE: 22

Arg Leu Ile Glu Asp Ile Cys Leu Pro Arg Trp Gly Cys Leu Trp Glu
1               5                   10                  15
Asp Asp

<210> SEQ ID NO 23
<211> LENGTH: 20
<212> TYPE: PRT
<213> ORGANISM: Artificial Sequence
<220> FEATURE:
<223> OTHER INFORMATION: Albumin binding peptide 2

<400> SEQUENCE: 23

Gln Arg Leu Met Glu Asp Ile Cys Leu Pro Arg Trp Gly Cys Leu Trp
1               5                   10                  15
Glu Asp Asp Phe
            20

<210> SEQ ID NO 24
<211> LENGTH: 21
<212> TYPE: PRT
<213> ORGANISM: Artificial Sequence
<220> FEATURE:
<223> OTHER INFORMATION: Albumin binding peptide 3

<400> SEQUENCE: 24

Gln Gly Leu Ile Gly Asp Ile Cys Leu Pro Arg Trp Gly Cys Leu Trp
1               5                   10                  15
Gly Asp Ser Val Lys
            20

<210> SEQ ID NO 25
<211> LENGTH: 20
<212> TYPE: PRT
<213> ORGANISM: Artificial Sequence
<220> FEATURE:
<223> OTHER INFORMATION: Albumin binding peptide 4

<400> SEQUENCE: 25

Gly Glu Trp Trp Glu Asp Ile Cys Leu Pro Arg Trp Gly Cys Leu Trp
1               5                   10                  15
Glu Glu Glu Asp
            20

<210> SEQ ID NO 26
<211> LENGTH: 10
<212> TYPE: PRT
```

```
<213> ORGANISM: Artificial Sequence
<220> FEATURE:
<223> OTHER INFORMATION: Cysteine-containing peptide

<400> SEQUENCE: 26

Gly Gly Gly Ser Gly Cys Gly Gly Gly Ser
1               5                   10

<210> SEQ ID NO 27
<211> LENGTH: 4544
<212> TYPE: PRT
<213> ORGANISM: Homo sapiens
<220> FEATURE:
<221> NAME/KEY: MISC_FEATURE
<223> OTHER INFORMATION: Human LRP1
<220> FEATURE:
<221> NAME/KEY: SIGNAL
<222> LOCATION: (1)..(19)
<223> OTHER INFORMATION: signal peptide
<220> FEATURE:
<221> NAME/KEY: TRANSMEM
<222> LOCATION: (4424)..(4444)
<223> OTHER INFORMATION: transmembrane segment

<400> SEQUENCE: 27

Met Leu Thr Pro Pro Leu Leu Leu Leu Leu Pro Leu Leu Ser Ala Leu
1               5                   10                  15

Val Ala Ala Ala Ile Asp Ala Pro Lys Thr Cys Ser Pro Lys Gln Phe
            20                  25                  30

Ala Cys Arg Asp Gln Ile Thr Cys Ile Ser Lys Gly Trp Arg Cys Asp
        35                  40                  45

Gly Glu Arg Asp Cys Pro Asp Gly Ser Asp Glu Ala Pro Glu Ile Cys
    50                  55                  60

Pro Gln Ser Lys Ala Gln Arg Cys Gln Pro Asn Glu His Asn Cys Leu
65                  70                  75                  80

Gly Thr Glu Leu Cys Val Pro Met Ser Arg Leu Cys Asn Gly Val Gln
                85                  90                  95

Asp Cys Met Asp Gly Ser Asp Glu Gly Pro His Cys Arg Glu Leu Gln
            100                 105                 110

Gly Asn Cys Ser Arg Leu Gly Cys Gln His His Cys Val Pro Thr Leu
        115                 120                 125

Asp Gly Pro Thr Cys Tyr Cys Asn Ser Ser Phe Gln Leu Gln Ala Asp
    130                 135                 140

Gly Lys Thr Cys Lys Asp Phe Asp Glu Cys Ser Val Tyr Gly Thr Cys
145                 150                 155                 160

Ser Gln Leu Cys Thr Asn Thr Asp Gly Ser Phe Ile Cys Gly Cys Val
                165                 170                 175

Glu Gly Tyr Leu Leu Gln Pro Asp Asn Arg Ser Cys Lys Ala Lys Asn
            180                 185                 190

Glu Pro Val Asp Arg Pro Pro Val Leu Leu Ile Ala Asn Ser Gln Asn
        195                 200                 205

Ile Leu Ala Thr Tyr Leu Ser Gly Ala Gln Val Ser Thr Ile Thr Pro
    210                 215                 220

Thr Ser Thr Arg Gln Thr Thr Ala Met Asp Phe Ser Tyr Ala Asn Glu
225                 230                 235                 240

Thr Val Cys Trp Val His Val Gly Asp Ser Ala Ala Gln Thr Gln Leu
                245                 250                 255

Lys Cys Ala Arg Met Pro Gly Leu Lys Gly Phe Val Asp Glu His Thr
            260                 265                 270
```

```
Ile Asn Ile Ser Leu Ser Leu His His Val Glu Gln Met Ala Ile Asp
            275                 280                 285

Trp Leu Thr Gly Asn Phe Tyr Phe Val Asp Asp Ile Asp Asp Arg Ile
        290                 295                 300

Phe Val Cys Asn Arg Asn Gly Asp Thr Cys Val Thr Leu Leu Asp Leu
305                 310                 315                 320

Glu Leu Tyr Asn Pro Lys Gly Ile Ala Leu Asp Pro Ala Met Gly Lys
                325                 330                 335

Val Phe Phe Thr Asp Tyr Gly Gln Ile Pro Lys Val Glu Arg Cys Asp
            340                 345                 350

Met Asp Gly Gln Asn Arg Thr Lys Leu Val Asp Ser Lys Ile Val Phe
        355                 360                 365

Pro His Gly Ile Thr Leu Asp Leu Val Ser Arg Leu Val Tyr Trp Ala
    370                 375                 380

Asp Ala Tyr Leu Asp Tyr Ile Glu Val Val Asp Tyr Glu Gly Lys Gly
385                 390                 395                 400

Arg Gln Thr Ile Ile Gln Gly Ile Leu Ile Glu His Leu Tyr Gly Leu
                405                 410                 415

Thr Val Phe Glu Asn Tyr Leu Tyr Ala Thr Asn Ser Asp Asn Ala Asn
            420                 425                 430

Ala Gln Gln Lys Thr Ser Val Ile Arg Val Asn Arg Phe Asn Ser Thr
        435                 440                 445

Glu Tyr Gln Val Val Thr Arg Val Asp Lys Gly Gly Ala Leu His Ile
    450                 455                 460

Tyr His Gln Arg Gln Pro Arg Val Arg Ser His Ala Cys Glu Asn
465                 470                 475                 480

Asp Gln Tyr Gly Lys Pro Gly Gly Cys Ser Asp Ile Cys Leu Leu Ala
                485                 490                 495

Asn Ser His Lys Ala Arg Thr Cys Arg Cys Arg Ser Gly Phe Ser Leu
            500                 505                 510

Gly Ser Asp Gly Lys Ser Cys Lys Lys Pro Glu His Glu Leu Phe Leu
        515                 520                 525

Val Tyr Gly Lys Gly Arg Pro Gly Ile Ile Arg Gly Met Asp Met Gly
    530                 535                 540

Ala Lys Val Pro Asp Glu His Met Ile Pro Ile Glu Asn Leu Met Asn
545                 550                 555                 560

Pro Arg Ala Leu Asp Phe His Ala Glu Thr Gly Phe Ile Tyr Phe Ala
                565                 570                 575

Asp Thr Thr Ser Tyr Leu Ile Gly Arg Gln Lys Ile Asp Gly Thr Glu
            580                 585                 590

Arg Glu Thr Ile Leu Lys Asp Gly Ile His Asn Val Glu Gly Val Ala
        595                 600                 605

Val Asp Trp Met Gly Asp Asn Leu Tyr Trp Thr Asp Asp Gly Pro Lys
    610                 615                 620

Lys Thr Ile Ser Val Ala Arg Leu Glu Lys Ala Gln Thr Arg Lys
625                 630                 635                 640

Thr Leu Ile Glu Gly Lys Met Thr His Pro Arg Ala Ile Val Val Asp
                645                 650                 655

Pro Leu Asn Gly Trp Met Tyr Trp Thr Asp Trp Glu Glu Asp Pro Lys
            660                 665                 670

Asp Ser Arg Arg Gly Arg Leu Glu Arg Ala Trp Met Asp Gly Ser His
        675                 680                 685

Arg Asp Ile Phe Val Thr Ser Lys Thr Val Leu Trp Pro Asn Gly Leu
```

```
                690             695              700
Ser Leu Asp Ile Pro Ala Gly Arg Leu Tyr Trp Val Asp Ala Phe Tyr
705             710              715              720

Asp Arg Ile Glu Thr Ile Leu Leu Asn Gly Thr Asp Arg Lys Ile Val
                725              730              735

Tyr Glu Gly Pro Glu Leu Asn His Ala Phe Gly Leu Cys His His Gly
                740              745              750

Asn Tyr Leu Phe Trp Thr Glu Tyr Arg Ser Gly Ser Val Tyr Arg Leu
            755              760              765

Glu Arg Gly Val Gly Gly Ala Pro Pro Thr Val Thr Leu Leu Arg Ser
        770              775              780

Glu Arg Pro Pro Ile Phe Glu Ile Arg Met Tyr Asp Ala Gln Gln Gln
785              790              795              800

Gln Val Gly Thr Asn Lys Cys Arg Val Asn Asn Gly Gly Cys Ser Ser
                805              810              815

Leu Cys Leu Ala Thr Pro Gly Ser Arg Gln Cys Ala Cys Ala Glu Asp
                820              825              830

Gln Val Leu Asp Ala Asp Gly Val Thr Cys Leu Ala Asn Pro Ser Tyr
            835              840              845

Val Pro Pro Pro Gln Cys Gln Pro Gly Glu Phe Ala Cys Ala Asn Ser
850              855              860

Arg Cys Ile Gln Glu Arg Trp Lys Cys Asp Gly Asp Asn Asp Cys Leu
865              870              875              880

Asp Asn Ser Asp Glu Ala Pro Ala Leu Cys His Gln His Thr Cys Pro
                885              890              895

Ser Asp Arg Phe Lys Cys Glu Asn Asn Arg Cys Ile Pro Asn Arg Trp
            900              905              910

Leu Cys Asp Gly Asp Asn Asp Cys Gly Asn Ser Glu Asp Glu Ser Asn
            915              920              925

Ala Thr Cys Ser Ala Arg Thr Cys Pro Pro Asn Gln Phe Ser Cys Ala
        930              935              940

Ser Gly Arg Cys Ile Pro Ile Ser Trp Thr Cys Asp Leu Asp Asp Asp
945              950              955              960

Cys Gly Asp Arg Ser Asp Glu Ser Ala Ser Cys Ala Tyr Pro Thr Cys
                965              970              975

Phe Pro Leu Thr Gln Phe Thr Cys Asn Asn Gly Arg Cys Ile Asn Ile
            980              985              990

Asn Trp Arg Cys Asp Asn Asp Asn Asp Cys Gly Asp Asn Ser Asp Glu
        995              1000              1005

Ala Gly Cys Ser His Ser Cys Ser Ser Thr Gln Phe Lys Cys Asn
    1010             1015             1020

Ser Gly Arg Cys Ile Pro Glu His Trp Thr Cys Asp Gly Asp Asn
    1025             1030             1035

Asp Cys Gly Asp Tyr Ser Asp Glu Thr His Ala Asn Cys Thr Asn
    1040             1045             1050

Gln Ala Thr Arg Pro Pro Gly Gly Cys His Thr Asp Glu Phe Gln
    1055             1060             1065

Cys Arg Leu Asp Gly Leu Cys Ile Pro Leu Arg Trp Arg Cys Asp
    1070             1075             1080

Gly Asp Thr Asp Cys Met Asp Ser Ser Asp Glu Lys Ser Cys Glu
    1085             1090             1095

Gly Val Thr His Val Cys Asp Pro Ser Val Lys Phe Gly Cys Lys
    1100             1105             1110
```

```
Asp Ser Ala Arg Cys Ile Ser Lys Ala Trp Val Cys Asp Gly Asp
    1115                1120                1125

Asn Asp Cys Glu Asp Asn Ser Asp Glu Glu Asn Cys Glu Ser Leu
    1130                1135                1140

Ala Cys Arg Pro Pro Ser His Pro Cys Ala Asn Asn Thr Ser Val
    1145                1150                1155

Cys Leu Pro Pro Asp Lys Leu Cys Asp Gly Asn Asp Asp Cys Gly
    1160                1165                1170

Asp Gly Ser Asp Glu Gly Glu Leu Cys Asp Gln Cys Ser Leu Asn
    1175                1180                1185

Asn Gly Gly Cys Ser His Asn Cys Ser Val Ala Pro Gly Glu Gly
    1190                1195                1200

Ile Val Cys Ser Cys Pro Leu Gly Met Glu Leu Gly Pro Asp Asn
    1205                1210                1215

His Thr Cys Gln Ile Gln Ser Tyr Cys Ala Lys His Leu Lys Cys
    1220                1225                1230

Ser Gln Lys Cys Asp Gln Asn Lys Phe Ser Val Lys Cys Ser Cys
    1235                1240                1245

Tyr Glu Gly Trp Val Leu Glu Pro Asp Gly Glu Ser Cys Arg Ser
    1250                1255                1260

Leu Asp Pro Phe Lys Pro Phe Ile Ile Phe Ser Asn Arg His Glu
    1265                1270                1275

Ile Arg Arg Ile Asp Leu His Lys Gly Asp Tyr Ser Val Leu Val
    1280                1285                1290

Pro Gly Leu Arg Asn Thr Ile Ala Leu Asp Phe His Leu Ser Gln
    1295                1300                1305

Ser Ala Leu Tyr Trp Thr Asp Val Val Glu Asp Lys Ile Tyr Arg
    1310                1315                1320

Gly Lys Leu Leu Asp Asn Gly Ala Leu Thr Ser Phe Glu Val Val
    1325                1330                1335

Ile Gln Tyr Gly Leu Ala Thr Pro Glu Gly Leu Ala Val Asp Trp
    1340                1345                1350

Ile Ala Gly Asn Ile Tyr Trp Val Glu Ser Asn Leu Asp Gln Ile
    1355                1360                1365

Glu Val Ala Lys Leu Asp Gly Thr Leu Arg Thr Leu Leu Ala
    1370                1375                1380

Gly Asp Ile Glu His Pro Arg Ala Ile Ala Leu Asp Pro Arg Asp
    1385                1390                1395

Gly Ile Leu Phe Trp Thr Asp Trp Asp Ala Ser Leu Pro Arg Ile
    1400                1405                1410

Glu Ala Ala Ser Met Ser Gly Ala Gly Arg Arg Thr Val His Arg
    1415                1420                1425

Glu Thr Gly Ser Gly Gly Trp Pro Asn Gly Leu Thr Val Asp Tyr
    1430                1435                1440

Leu Glu Lys Arg Ile Leu Trp Ile Asp Ala Arg Ser Asp Ala Ile
    1445                1450                1455

Tyr Ser Ala Arg Tyr Asp Gly Ser Gly His Met Glu Val Leu Arg
    1460                1465                1470

Gly His Glu Phe Leu Ser His Pro Phe Ala Val Thr Leu Tyr Gly
    1475                1480                1485

Gly Glu Val Tyr Trp Thr Asp Trp Arg Thr Asn Thr Leu Ala Lys
    1490                1495                1500
```

```
Ala Asn Lys Trp Thr Gly His Asn Val Thr Val Val Gln Arg Thr
1505                    1510                1515

Asn Thr Gln Pro Phe Asp Leu Gln Val Tyr His Pro Ser Arg Gln
1520                    1525                1530

Pro Met Ala Pro Asn Pro Cys Glu Ala Asn Gly Gly Gln Gly Pro
1535                    1540                1545

Cys Ser His Leu Cys Leu Ile Asn Tyr Asn Arg Thr Val Ser Cys
1550                    1555                1560

Ala Cys Pro His Leu Met Lys Leu His Lys Asp Asn Thr Thr Cys
1565                    1570                1575

Tyr Glu Phe Lys Lys Phe Leu Leu Tyr Ala Arg Gln Met Glu Ile
1580                    1585                1590

Arg Gly Val Asp Leu Asp Ala Pro Tyr Tyr Asn Tyr Ile Ile Ser
1595                    1600                1605

Phe Thr Val Pro Asp Ile Asp Asn Val Thr Val Leu Asp Tyr Asp
1610                    1615                1620

Ala Arg Glu Gln Arg Val Tyr Trp Ser Asp Val Arg Thr Gln Ala
1625                    1630                1635

Ile Lys Arg Ala Phe Ile Asn Gly Thr Gly Val Glu Thr Val Val
1640                    1645                1650

Ser Ala Asp Leu Pro Asn Ala His Gly Leu Ala Val Asp Trp Val
1655                    1660                1665

Ser Arg Asn Leu Phe Trp Thr Ser Tyr Asp Thr Asn Lys Lys Gln
1670                    1675                1680

Ile Asn Val Ala Arg Leu Asp Gly Ser Phe Lys Asn Ala Val Val
1685                    1690                1695

Gln Gly Leu Glu Gln Pro His Gly Leu Val Val His Pro Leu Arg
1700                    1705                1710

Gly Lys Leu Tyr Trp Thr Asp Gly Asp Asn Ile Ser Met Ala Asn
1715                    1720                1725

Met Asp Gly Ser Asn Arg Thr Leu Leu Phe Ser Gly Gln Lys Gly
1730                    1735                1740

Pro Val Gly Leu Ala Ile Asp Phe Pro Glu Ser Lys Leu Tyr Trp
1745                    1750                1755

Ile Ser Ser Gly Asn His Thr Ile Asn Arg Cys Asn Leu Asp Gly
1760                    1765                1770

Ser Gly Leu Glu Val Ile Asp Ala Met Arg Ser Gln Leu Gly Lys
1775                    1780                1785

Ala Thr Ala Leu Ala Ile Met Gly Asp Lys Leu Trp Trp Ala Asp
1790                    1795                1800

Gln Val Ser Glu Lys Met Gly Thr Cys Ser Lys Ala Asp Gly Ser
1805                    1810                1815

Gly Ser Val Val Leu Arg Asn Ser Thr Thr Leu Val Met His Met
1820                    1825                1830

Lys Val Tyr Asp Glu Ser Ile Gln Leu Asp His Lys Gly Thr Asn
1835                    1840                1845

Pro Cys Ser Val Asn Asn Gly Asp Cys Ser Gln Leu Cys Leu Pro
1850                    1855                1860

Thr Ser Glu Thr Thr Arg Ser Cys Met Cys Thr Ala Gly Tyr Ser
1865                    1870                1875

Leu Arg Ser Gly Gln Gln Ala Cys Glu Gly Val Gly Ser Phe Leu
1880                    1885                1890

Leu Tyr Ser Val His Glu Gly Ile Arg Gly Ile Pro Leu Asp Pro
```

```
              1895                1900                1905
Asn Asp Lys Ser Asp Ala Leu Val Pro Val Ser Gly Thr Ser Leu
    1910                1915                1920

Ala Val Gly Ile Asp Phe His Ala Glu Asn Asp Thr Ile Tyr Trp
    1925                1930                1935

Val Asp Met Gly Leu Ser Thr Ile Ser Arg Ala Lys Arg Asp Gln
    1940                1945                1950

Thr Trp Arg Glu Asp Val Val Thr Asn Gly Ile Gly Arg Val Glu
    1955                1960                1965

Gly Ile Ala Val Asp Trp Ile Ala Gly Asn Ile Tyr Trp Thr Asp
    1970                1975                1980

Gln Gly Phe Asp Val Ile Glu Val Ala Arg Leu Asn Gly Ser Phe
    1985                1990                1995

Arg Tyr Val Val Ile Ser Gln Gly Leu Asp Lys Pro Arg Ala Ile
    2000                2005                2010

Thr Val His Pro Glu Lys Gly Tyr Leu Phe Trp Thr Glu Trp Gly
    2015                2020                2025

Gln Tyr Pro Arg Ile Glu Arg Ser Arg Leu Asp Gly Thr Glu Arg
    2030                2035                2040

Val Val Leu Val Asn Val Ser Ile Ser Trp Pro Asn Gly Ile Ser
    2045                2050                2055

Val Asp Tyr Gln Asp Gly Lys Leu Tyr Trp Cys Asp Ala Arg Thr
    2060                2065                2070

Asp Lys Ile Glu Arg Ile Asp Leu Glu Thr Gly Glu Asn Arg Glu
    2075                2080                2085

Val Val Leu Ser Ser Asn Asn Met Asp Met Phe Ser Val Ser Val
    2090                2095                2100

Phe Glu Asp Phe Ile Tyr Trp Ser Asp Arg Thr His Ala Asn Gly
    2105                2110                2115

Ser Ile Lys Arg Gly Ser Lys Asp Asn Ala Thr Asp Ser Val Pro
    2120                2125                2130

Leu Arg Thr Gly Ile Gly Val Gln Leu Lys Asp Ile Lys Val Phe
    2135                2140                2145

Asn Arg Asp Arg Gln Lys Gly Thr Asn Val Cys Ala Val Ala Asn
    2150                2155                2160

Gly Gly Cys Gln Gln Leu Cys Leu Tyr Arg Gly Arg Gly Gln Arg
    2165                2170                2175

Ala Cys Ala Cys Ala His Gly Met Leu Ala Glu Asp Gly Ala Ser
    2180                2185                2190

Cys Arg Glu Tyr Ala Gly Tyr Leu Leu Tyr Ser Glu Arg Thr Ile
    2195                2200                2205

Leu Lys Ser Ile His Leu Ser Asp Glu Arg Asn Leu Asn Ala Pro
    2210                2215                2220

Val Gln Pro Phe Glu Asp Pro Glu His Met Lys Asn Val Ile Ala
    2225                2230                2235

Leu Ala Phe Asp Tyr Arg Ala Gly Thr Ser Pro Gly Thr Pro Asn
    2240                2245                2250

Arg Ile Phe Phe Ser Asp Ile His Phe Gly Asn Ile Gln Gln Ile
    2255                2260                2265

Asn Asp Asp Gly Ser Arg Arg Ile Thr Ile Val Glu Asn Val Gly
    2270                2275                2280

Ser Val Glu Gly Leu Ala Tyr His Arg Gly Trp Asp Thr Leu Tyr
    2285                2290                2295
```

-continued

```
Trp Thr Ser Tyr Thr Thr Ser Thr Ile Thr Arg His Thr Val Asp
    2300                2305                2310

Gln Thr Arg Pro Gly Ala Phe Glu Arg Glu Thr Val Ile Thr Met
    2315                2320                2325

Ser Gly Asp Asp His Pro Arg Ala Phe Val Leu Asp Glu Cys Gln
    2330                2335                2340

Asn Leu Met Phe Trp Thr Asn Trp Asn Glu Gln His Pro Ser Ile
    2345                2350                2355

Met Arg Ala Ala Leu Ser Gly Ala Asn Val Leu Thr Leu Ile Glu
    2360                2365                2370

Lys Asp Ile Arg Thr Pro Asn Gly Leu Ala Ile Asp His Arg Ala
    2375                2380                2385

Glu Lys Leu Tyr Phe Ser Asp Ala Thr Leu Asp Lys Ile Glu Arg
    2390                2395                2400

Cys Glu Tyr Asp Gly Ser His Arg Tyr Val Ile Leu Lys Ser Glu
    2405                2410                2415

Pro Val His Pro Phe Gly Leu Ala Val Tyr Gly Glu His Ile Phe
    2420                2425                2430

Trp Thr Asp Trp Val Arg Arg Ala Val Gln Arg Ala Asn Lys His
    2435                2440                2445

Val Gly Ser Asn Met Lys Leu Leu Arg Val Asp Ile Pro Gln Gln
    2450                2455                2460

Pro Met Gly Ile Ile Ala Val Ala Asn Asp Thr Asn Ser Cys Glu
    2465                2470                2475

Leu Ser Pro Cys Arg Ile Asn Asn Gly Gly Cys Gln Asp Leu Cys
    2480                2485                2490

Leu Leu Thr His Gln Gly His Val Asn Cys Ser Cys Arg Gly Gly
    2495                2500                2505

Arg Ile Leu Gln Asp Asp Leu Thr Cys Arg Ala Val Asn Ser Ser
    2510                2515                2520

Cys Arg Ala Gln Asp Glu Phe Glu Cys Ala Asn Gly Glu Cys Ile
    2525                2530                2535

Asn Phe Ser Leu Thr Cys Asp Gly Val Pro His Cys Lys Asp Lys
    2540                2545                2550

Ser Asp Glu Lys Pro Ser Tyr Cys Asn Ser Arg Arg Cys Lys Lys
    2555                2560                2565

Thr Phe Arg Gln Cys Ser Asn Gly Arg Cys Val Ser Asn Met Leu
    2570                2575                2580

Trp Cys Asn Gly Ala Asp Asp Cys Gly Asp Gly Ser Asp Glu Ile
    2585                2590                2595

Pro Cys Asn Lys Thr Ala Cys Gly Val Gly Glu Phe Arg Cys Arg
    2600                2605                2610

Asp Gly Thr Cys Ile Gly Asn Ser Ser Arg Cys Asn Gln Phe Val
    2615                2620                2625

Asp Cys Glu Asp Ala Ser Asp Glu Met Asn Cys Ser Ala Thr Asp
    2630                2635                2640

Cys Ser Ser Tyr Phe Arg Leu Gly Val Lys Gly Val Leu Phe Gln
    2645                2650                2655

Pro Cys Glu Arg Thr Ser Leu Cys Tyr Ala Pro Ser Trp Val Cys
    2660                2665                2670

Asp Gly Ala Asn Asp Cys Gly Asp Tyr Ser Asp Glu Arg Asp Cys
    2675                2680                2685
```

```
Pro Gly Val Lys Arg Pro Arg Cys Pro Leu Asn Tyr Phe Ala Cys
    2690            2695            2700

Pro Ser Gly Arg Cys Ile Pro Met Ser Trp Thr Cys Asp Lys Glu
    2705            2710            2715

Asp Asp Cys Glu His Gly Glu Asp Glu Thr His Cys Asn Lys Phe
    2720            2725            2730

Cys Ser Glu Ala Gln Phe Glu Cys Gln Asn His Arg Cys Ile Ser
    2735            2740            2745

Lys Gln Trp Leu Cys Asp Gly Ser Asp Cys Gly Asp Gly Ser
    2750            2755            2760

Asp Glu Ala Ala His Cys Glu Gly Lys Thr Cys Gly Pro Ser Ser
    2765            2770            2775

Phe Ser Cys Pro Gly Thr His Val Cys Val Pro Glu Arg Trp Leu
    2780            2785            2790

Cys Asp Gly Asp Lys Asp Cys Ala Asp Gly Ala Asp Glu Ser Ile
    2795            2800            2805

Ala Ala Gly Cys Leu Tyr Asn Ser Thr Cys Asp Asp Arg Glu Phe
    2810            2815            2820

Met Cys Gln Asn Arg Gln Cys Ile Pro Lys His Phe Val Cys Asp
    2825            2830            2835

His Asp Arg Asp Cys Ala Asp Gly Ser Asp Glu Ser Pro Glu Cys
    2840            2845            2850

Glu Tyr Pro Thr Cys Gly Pro Ser Glu Phe Arg Cys Ala Asn Gly
    2855            2860            2865

Arg Cys Leu Ser Ser Arg Gln Trp Glu Cys Asp Gly Glu Asn Asp
    2870            2875            2880

Cys His Asp Gln Ser Asp Glu Ala Pro Lys Asn Pro His Cys Thr
    2885            2890            2895

Ser Pro Glu His Lys Cys Asn Ala Ser Ser Gln Phe Leu Cys Ser
    2900            2905            2910

Ser Gly Arg Cys Val Ala Glu Ala Leu Leu Cys Asn Gly Gln Asp
    2915            2920            2925

Asp Cys Gly Asp Ser Ser Asp Glu Arg Gly Cys His Ile Asn Glu
    2930            2935            2940

Cys Leu Ser Arg Lys Leu Ser Gly Cys Ser Gln Asp Cys Glu Asp
    2945            2950            2955

Leu Lys Ile Gly Phe Lys Cys Arg Cys Arg Pro Gly Phe Arg Leu
    2960            2965            2970

Lys Asp Asp Gly Arg Thr Cys Ala Asp Val Asp Glu Cys Ser Thr
    2975            2980            2985

Thr Phe Pro Cys Ser Gln Arg Cys Ile Asn Thr His Gly Ser Tyr
    2990            2995            3000

Lys Cys Leu Cys Val Glu Gly Tyr Ala Pro Arg Gly Gly Asp Pro
    3005            3010            3015

His Ser Cys Lys Ala Val Thr Asp Glu Glu Pro Phe Leu Ile Phe
    3020            3025            3030

Ala Asn Arg Tyr Tyr Leu Arg Lys Leu Asn Leu Asp Gly Ser Asn
    3035            3040            3045

Tyr Thr Leu Leu Lys Gln Gly Leu Asn Asn Ala Val Ala Leu Asp
    3050            3055            3060

Phe Asp Tyr Arg Glu Gln Met Ile Tyr Trp Thr Asp Val Thr Thr
    3065            3070            3075

Gln Gly Ser Met Ile Arg Arg Met His Leu Asn Gly Ser Asn Val
```

```
                3080                3085                3090
Gln Val Leu His Arg Thr Gly Leu Ser Asn Pro Asp Gly Leu Ala
    3095                3100                3105

Val Asp Trp Val Gly Gly Asn Leu Tyr Trp Cys Asp Lys Gly Arg
    3110                3115                3120

Asp Thr Ile Glu Val Ser Lys Leu Asn Gly Ala Tyr Arg Thr Val
    3125                3130                3135

Leu Val Ser Ser Gly Leu Arg Glu Pro Arg Ala Leu Val Val Asp
    3140                3145                3150

Val Gln Asn Gly Tyr Leu Tyr Trp Thr Asp Trp Gly Asp His Ser
    3155                3160                3165

Leu Ile Gly Arg Ile Gly Met Asp Gly Ser Ser Arg Ser Val Ile
    3170                3175                3180

Val Asp Thr Lys Ile Thr Trp Pro Asn Gly Leu Thr Leu Asp Tyr
    3185                3190                3195

Val Thr Glu Arg Ile Tyr Trp Ala Asp Ala Arg Glu Asp Tyr Ile
    3200                3205                3210

Glu Phe Ala Ser Leu Asp Gly Ser Asn Arg His Val Val Leu Ser
    3215                3220                3225

Gln Asp Ile Pro His Ile Phe Ala Leu Thr Leu Phe Glu Asp Tyr
    3230                3235                3240

Val Tyr Trp Thr Asp Trp Glu Thr Lys Ser Ile Asn Arg Ala His
    3245                3250                3255

Lys Thr Thr Gly Thr Asn Lys Thr Leu Leu Ile Ser Thr Leu His
    3260                3265                3270

Arg Pro Met Asp Leu His Val Phe His Ala Leu Arg Gln Pro Asp
    3275                3280                3285

Val Pro Asn His Pro Cys Lys Val Asn Asn Gly Gly Cys Ser Asn
    3290                3295                3300

Leu Cys Leu Leu Ser Pro Gly Gly Gly His Lys Cys Ala Cys Pro
    3305                3310                3315

Thr Asn Phe Tyr Leu Gly Ser Asp Gly Arg Thr Cys Val Ser Asn
    3320                3325                3330

Cys Thr Ala Ser Gln Phe Val Cys Lys Asn Asp Lys Cys Ile Pro
    3335                3340                3345

Phe Trp Trp Lys Cys Asp Thr Glu Asp Asp Cys Gly Asp His Ser
    3350                3355                3360

Asp Glu Pro Pro Asp Cys Pro Glu Phe Lys Cys Arg Pro Gly Gln
    3365                3370                3375

Phe Gln Cys Ser Thr Gly Ile Cys Thr Asn Pro Ala Phe Ile Cys
    3380                3385                3390

Asp Gly Asp Asn Asp Cys Gln Asp Asn Ser Asp Glu Ala Asn Cys
    3395                3400                3405

Asp Ile His Val Cys Leu Pro Ser Gln Phe Lys Cys Thr Asn Thr
    3410                3415                3420

Asn Arg Cys Ile Pro Gly Ile Phe Arg Cys Asn Gly Gln Asp Asn
    3425                3430                3435

Cys Gly Asp Gly Glu Asp Glu Arg Asp Cys Pro Glu Val Thr Cys
    3440                3445                3450

Ala Pro Asn Gln Phe Gln Cys Ser Ile Thr Lys Arg Cys Ile Pro
    3455                3460                3465

Arg Val Trp Val Cys Asp Arg Asp Asn Asp Cys Val Asp Gly Ser
    3470                3475                3480
```

-continued

Asp Glu Pro Ala Asn Cys Thr Gln Met Thr Cys Gly Val Asp Glu
3485             3490                 3495

Phe Arg Cys Lys Asp Ser Gly Arg Cys Ile Pro Ala Arg Trp Lys
3500             3505                 3510

Cys Asp Gly Glu Asp Cys Gly Asp Gly Ser Asp Glu Pro Lys
3515             3520                 3525

Glu Glu Cys Asp Glu Arg Thr Cys Glu Pro Tyr Gln Phe Arg Cys
3530             3535                 3540

Lys Asn Asn Arg Cys Val Pro Gly Arg Trp Gln Cys Asp Tyr Asp
3545             3550                 3555

Asn Asp Cys Gly Asp Asn Ser Asp Glu Glu Ser Cys Thr Pro Arg
3560             3565                 3570

Pro Cys Ser Glu Ser Glu Phe Ser Cys Ala Asn Gly Arg Cys Ile
3575             3580                 3585

Ala Gly Arg Trp Lys Cys Asp Gly Asp His Asp Cys Ala Asp Gly
3590             3595                 3600

Ser Asp Glu Lys Asp Cys Thr Pro Arg Cys Asp Met Asp Gln Phe
3605             3610                 3615

Gln Cys Lys Ser Gly His Cys Ile Pro Leu Arg Trp Arg Cys Asp
3620             3625                 3630

Ala Asp Ala Asp Cys Met Asp Gly Ser Asp Glu Glu Ala Cys Gly
3635             3640                 3645

Thr Gly Val Arg Thr Cys Pro Leu Asp Glu Phe Gln Cys Asn Asn
3650             3655                 3660

Thr Leu Cys Lys Pro Leu Ala Trp Lys Cys Asp Gly Glu Asp Asp
3665             3670                 3675

Cys Gly Asp Asn Ser Asp Glu Asn Pro Glu Glu Cys Ala Arg Phe
3680             3685                 3690

Val Cys Pro Pro Asn Arg Pro Phe Arg Cys Lys Asn Asp Arg Val
3695             3700                 3705

Cys Leu Trp Ile Gly Arg Gln Cys Asp Gly Thr Asp Asn Cys Gly
3710             3715                 3720

Asp Gly Thr Asp Glu Glu Asp Cys Glu Pro Pro Thr Ala His Thr
3725             3730                 3735

Thr His Cys Lys Asp Lys Lys Glu Phe Leu Cys Arg Asn Gln Arg
3740             3745                 3750

Cys Leu Ser Ser Ser Leu Arg Cys Asn Met Phe Asp Asp Cys Gly
3755             3760                 3765

Asp Gly Ser Asp Glu Glu Asp Cys Ser Ile Asp Pro Lys Leu Thr
3770             3775                 3780

Ser Cys Ala Thr Asn Ala Ser Ile Cys Gly Asp Glu Ala Arg Cys
3785             3790                 3795

Val Arg Thr Glu Lys Ala Ala Tyr Cys Ala Cys Arg Ser Gly Phe
3800             3805                 3810

His Thr Val Pro Gly Gln Pro Gly Cys Gln Asp Ile Asn Glu Cys
3815             3820                 3825

Leu Arg Phe Gly Thr Cys Ser Gln Leu Cys Asn Asn Thr Lys Gly
3830             3835                 3840

Gly His Leu Cys Ser Cys Ala Arg Asn Phe Met Lys Thr His Asn
3845             3850                 3855

Thr Cys Lys Ala Glu Gly Ser Glu Tyr Gln Val Leu Tyr Ile Ala
3860             3865                 3870

```
Asp Asp Asn Glu Ile Arg Ser Leu Phe Pro Gly His Pro His Ser
3875                3880                3885

Ala Tyr Glu Gln Ala Phe Gln Gly Asp Glu Ser Val Arg Ile Asp
3890                3895                3900

Ala Met Asp Val His Val Lys Ala Gly Arg Val Tyr Trp Thr Asn
3905                3910                3915

Trp His Thr Gly Thr Ile Ser Tyr Arg Ser Leu Pro Pro Ala Ala
3920                3925                3930

Pro Pro Thr Thr Ser Asn Arg His Arg Arg Gln Ile Asp Arg Gly
3935                3940                3945

Val Thr His Leu Asn Ile Ser Gly Leu Lys Met Pro Arg Gly Ile
3950                3955                3960

Ala Ile Asp Trp Val Ala Gly Asn Val Tyr Trp Thr Asp Ser Gly
3965                3970                3975

Arg Asp Val Ile Glu Val Ala Gln Met Lys Gly Glu Asn Arg Lys
3980                3985                3990

Thr Leu Ile Ser Gly Met Ile Asp Glu Pro His Ala Ile Val Val
3995                4000                4005

Asp Pro Leu Arg Gly Thr Met Tyr Trp Ser Asp Trp Gly Asn His
4010                4015                4020

Pro Lys Ile Glu Thr Ala Ala Met Asp Gly Thr Leu Arg Glu Thr
4025                4030                4035

Leu Val Gln Asp Asn Ile Gln Trp Pro Thr Gly Leu Ala Val Asp
4040                4045                4050

Tyr His Asn Glu Arg Leu Tyr Trp Ala Asp Ala Lys Leu Ser Val
4055                4060                4065

Ile Gly Ser Ile Arg Leu Asn Gly Thr Asp Pro Ile Val Ala Ala
4070                4075                4080

Asp Ser Lys Arg Gly Leu Ser His Pro Phe Ser Ile Asp Val Phe
4085                4090                4095

Glu Asp Tyr Ile Tyr Gly Val Thr Tyr Ile Asn Asn Arg Val Phe
4100                4105                4110

Lys Ile His Lys Phe Gly His Ser Pro Leu Val Asn Leu Thr Gly
4115                4120                4125

Gly Leu Ser His Ala Ser Asp Val Val Leu Tyr His Gln His Lys
4130                4135                4140

Gln Pro Glu Val Thr Asn Pro Cys Asp Arg Lys Lys Cys Glu Trp
4145                4150                4155

Leu Cys Leu Leu Ser Pro Ser Gly Pro Val Cys Thr Cys Pro Asn
4160                4165                4170

Gly Lys Arg Leu Asp Asn Gly Thr Cys Val Pro Val Pro Ser Pro
4175                4180                4185

Thr Pro Pro Pro Asp Ala Pro Arg Pro Gly Thr Cys Asn Leu Gln
4190                4195                4200

Cys Phe Asn Gly Gly Ser Cys Phe Leu Asn Ala Arg Arg Gln Pro
4205                4210                4215

Lys Cys Arg Cys Gln Pro Arg Tyr Thr Gly Asp Lys Cys Glu Leu
4220                4225                4230

Asp Gln Cys Trp Glu His Cys Arg Asn Gly Gly Thr Cys Ala Ala
4235                4240                4245

Ser Pro Ser Gly Met Pro Thr Cys Arg Cys Pro Thr Gly Phe Thr
4250                4255                4260

Gly Pro Lys Cys Thr Gln Gln Val Cys Ala Gly Tyr Cys Ala Asn
```

```
                4265                4270                4275
Asn Ser Thr Cys Thr Val Asn Gln Gly Asn Gln Pro Gln Cys Arg
        4280                4285                4290

Cys Leu Pro Gly Phe Leu Gly Asp Arg Cys Gln Tyr Arg Gln Cys
        4295                4300                4305

Ser Gly Tyr Cys Glu Asn Phe Gly Thr Cys Gln Met Ala Ala Asp
        4310                4315                4320

Gly Ser Arg Gln Cys Arg Cys Thr Ala Tyr Phe Glu Gly Ser Arg
        4325                4330                4335

Cys Glu Val Asn Lys Cys Ser Arg Cys Leu Glu Gly Ala Cys Val
        4340                4345                4350

Val Asn Lys Gln Ser Gly Asp Val Thr Cys Asn Cys Thr Asp Gly
        4355                4360                4365

Arg Val Ala Pro Ser Cys Leu Thr Cys Val Gly His Cys Ser Asn
        4370                4375                4380

Gly Gly Ser Cys Thr Met Asn Ser Lys Met Met Pro Glu Cys Gln
        4385                4390                4395

Cys Pro Pro His Met Thr Gly Pro Arg Cys Glu Glu His Val Phe
        4400                4405                4410

Ser Gln Gln Gln Pro Gly His Ile Ala Ser Ile Leu Ile Pro Leu
        4415                4420                4425

Leu Leu Leu Leu Leu Leu Val Leu Val Ala Gly Val Val Phe Trp
        4430                4435                4440

Tyr Lys Arg Arg Val Gln Gly Ala Lys Gly Phe Gln His Gln Arg
        4445                4450                4455

Met Thr Asn Gly Ala Met Asn Val Glu Ile Gly Asn Pro Thr Tyr
        4460                4465                4470

Lys Met Tyr Glu Gly Gly Glu Pro Asp Asp Val Gly Gly Leu Leu
        4475                4480                4485

Asp Ala Asp Phe Ala Leu Asp Pro Asp Lys Pro Thr Asn Phe Thr
        4490                4495                4500

Asn Pro Val Tyr Ala Thr Leu Tyr Met Gly Gly His Gly Ser Arg
        4505                4510                4515

His Ser Leu Ala Ser Thr Asp Glu Lys Arg Glu Leu Leu Gly Arg
        4520                4525                4530

Gly Pro Glu Asp Glu Ile Gly Asp Pro Leu Ala
        4535                4540

<210> SEQ ID NO 28
<211> LENGTH: 13
<212> TYPE: PRT
<213> ORGANISM: Artificial Sequence
<220> FEATURE:
<223> OTHER INFORMATION: Biotin Acceptor Peptide (BAP)

<400> SEQUENCE: 28

Leu Asn Asp Ile Phe Glu Ala Gln Lys Ile Glu Trp His
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Lipoate Acceptor Peptide 2 (LAP2)

<400> SEQUENCE: 29
```

```
Gly Phe Glu Ile Asp Lys Val Trp Tyr Asp Leu Asp Ala
1               5                   10

<210> SEQ ID NO 30
<211> LENGTH: 5
<212> TYPE: PRT
<213> ORGANISM: Artificial Sequence
<220> FEATURE:
<223> OTHER INFORMATION: HAPylation motif
<220> FEATURE:
<221> NAME/KEY: REPEAT
<222> LOCATION: (1)..(5)
<223> OTHER INFORMATION: can be repeated up to 400 times

<400> SEQUENCE: 30

Gly Gly Gly Gly Ser
1               5

<210> SEQ ID NO 31
<211> LENGTH: 29
<212> TYPE: PRT
<213> ORGANISM: Artificial Sequence
<220> FEATURE:
<223> OTHER INFORMATION: CTP

<400> SEQUENCE: 31

Asp Ser Ser Ser Ser Lys Ala Pro Pro Pro Ser Leu Pro Ser Pro Ser
1               5                   10                  15

Arg Leu Pro Gly Pro Ser Asp Thr Pro Ile Leu Pro Gln
            20                  25
```